(12) United States Patent
Hoelzemann et al.

(10) Patent No.: US 9,617,266 B2
(45) Date of Patent: Apr. 11, 2017

(54) IMIDAZOPYRIMIDINE DERIVATIVES

(71) Applicant: Merck Patent GmbH, Darmstadt (DE)

(72) Inventors: Guenter Hoelzemann, Seeheim-Jugenheim (DE); Dieter Dorsch, Ober-Ramstadt (DE); Ansgar Wegener, Heusenstamm (DE); Oliver Poeschke, Wiesbaden (DE); Michael Busch, Darmstadt (DE); Jeyaprakashnarayanan Seenisamy, Bangalore (IN)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/772,430

(22) PCT Filed: Feb. 11, 2014

(86) PCT No.: PCT/EP2014/000371
§ 371 (c)(1),
(2) Date: Sep. 3, 2015

(87) PCT Pub. No.: WO2014/135245
PCT Pub. Date: Sep. 12, 2014

(65) Prior Publication Data
US 2016/0002242 A1 Jan. 7, 2016

(30) Foreign Application Priority Data
Mar. 5, 2013 (EP) ...................................... 13001111

(51) Int. Cl.
*A61K 31/52* (2006.01)
*C07D 473/32* (2006.01)

(52) U.S. Cl.
CPC ............ *C07D 473/32* (2013.01); *A61K 31/52* (2013.01)

(58) Field of Classification Search
None
See application file for complete search history.

(56) References Cited

U.S. PATENT DOCUMENTS

| 7,723,340 B2 | 5/2010 | Albers et al. |
| 2006/0287344 A1 | 12/2006 | Albers et al. |
| 2009/0312320 A1 | 12/2009 | Albers et al. |

FOREIGN PATENT DOCUMENTS

| WO | 2006076595 A1 | 7/2006 |
| WO | 2011106168 A1 | 9/2011 |

OTHER PUBLICATIONS

Byrn, Stephen. Solid-State Chemistry of Drugs, 2nd Ed. (1999), Ch. 11 Hydrates and Solvates, 233-247.*
Morissette, Sherry. Adv. Drug Delivery Rev. (2004), 56, 275-300.*
Rouhi, A. Maureen. Chem. & Eng. News, (2003), 81(8), 32-35.*
Devi, Latha. PLOS ONE 8(10) (2013) 1-8.*
Ravishankar, Buvana. PNAS 112(34) (2015) 10774-10779.*
Auto-immune Diseases: MedlinePlus. (2014). Web: <https://www.nlm.nih.gov/medlineplus/autoimmunediseases.html>.*
UCSF Medical Center:Neurological Disorders. (2016). Web: <https://www.ucsfhealth.org/conditions/neurological_disorders/>.*
Infections: MedlinePlus. (2016). Web: < https://www.nlm.nih.gov/medlineplus/infections.html>.*
WebMD. Inherited Metabolic Disorders: Types, Causes, Symptoms and Treatments. (2014). Web: <http://www.webmd.com/a-to-z-guides/inherited-metabolic-disorder-types-and-treatments?page=2>.*
MedicineNet.com. (2004). Web< http://www.medterms.com>.*
WebMD:Multiple Sclerosis (MS)—Prevention. (2016). Web < http://www.webmd.com/multiple-sclerosis/tc/multiple-sclerosis-ms-prevention>.*
WebMD:Understanding Alzheimer's Disease—Prevention. (2016). Web < http://www.webmd.com/alzheimers/guide/understanding-alzheimers-disease-prevention>.*
WebMD:Epstein-Barr Virus (EBV) (2016). Web: < http://www.webmd.com/a-to-z-guides/epstein-barr-virus?page=2>.*
International Search Report from PCT Application No. PCT/EP2014/000371 dated Mar. 25, 2014.

* cited by examiner

*Primary Examiner* — Golam M M Shameem
*Assistant Examiner* — Laura Daniel
(74) *Attorney, Agent, or Firm* — Millen White Zelano and Branigan, PC; John Sopp; Anthony Zelano

(57) ABSTRACT

Compounds of the formula I

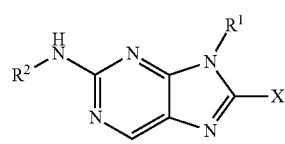

in which X, $R^1$ and $R^2$ have the meanings indicated in Claim 1,
are inhibitors of GCN2, and can be employed, inter alia, for the treatment of cancer.

11 Claims, No Drawings

IMIDAZOPYRIMIDINE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by protein kinases, in particular immune-modulatory or stress response kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control, immune modulation, stress response and angiogenesis, in which protein kinases play a pivotal role are cellular processes associated with numerous disease conditions such as but not limited to cancer, inflammatory diseases, neurodegenerative diseases, chronic infections, abnormal angiogenesis and diseases related thereto, atherosclerosis, macular degeneration, diabetes, obesity, and pain.

Compounds of formula I inhibit the stress response eIF2 kinase EIF2AK4 called general control nonderepressible 2 (GCN2).

Many strategies of cancer treatment of solid tumors focus on the surgically removal of the tumor mass as far as possible and the subsequent eradication of any residual tumor cells by radiotherapy and chemotherapy with cytotoxic agents or inhibitors that target cancer cell pathways more specifically. However, the success of such approach is limited and often does not persist. This is mainly due to the narrow therapeutic window for such cytotoxic agents (specificity and side effects) and to the capability of cancer calls to adapt to the selective pressure applied by cytotoxic or other inhibitory agents. The survival of a small number of tumor (stem) cells that acquired resistance to the initial treatment can be sufficient to seed the regrowth of a tumor. These relapses are in most cases more difficult to treat compared to that of the initial tumors. As a consequence the more successful targeting of tumor cells may require targeting multiple survival and escape mechanism of tumor cells in parallel (Muller & Prendegast 2007).

Development of malignancies is accompanied by a major roll up of the cellular physiology. During this process several qualities are acquired by the cancer cells that are basis for immortalization or insensitivity to growth inhibitory signals. In addition the tumor cells also modify the interaction with the microenvironment and beyond. The latter area includes the strategies of tumor cells to escape from the immunological surveillance (Muller & Prendegast 2007). The immune surveillance limits malignant growth but also provides a selective pressure triggering the evolution of mechanisms for evading the immune response as reviewed by [Dunn et al. 2004]. Essentially it has been frequently observed that ablation of T cell immunity is sufficient to increase tumor incidence [Shankaran et al. 2001] and it is believed that immune escape is affecting tumor dormancy versus progression, promoting invasion and metastasis and negatively impacts on therapeutic response.

Several mechanistic studies discovered that immune escape has an important interface with metabolic alterations within the tumor microenvironment. Here important roles in mediating immune tolerance to antigens have been associated to the catabolism of the essential amino acids tryptophan and arginine, carried out by the enzymes indoleamine 2,3-dioxygenase (IDO) and arginase I (ARG), respectively (Bronte and Zanovello, 2005; Muller et al., 2005b; Muller and Prendergast, 2007; Munn and Mellor, 2007; Popovic et al., 2007).

IDO is a single-chain oxidoreductase that catalyzes the degradation of tryptophan to kynurenine. IDO is not responsible for catabolizing excess dietary tryptophan but to modulate tryptophan level in a local environment. Elevations in tryptophan catabolism in cancer patients manifest in significantly altered serum concentration of tryptophan or catabolites and this was correlated to IDO which is commonly elevated in tumors and draining lymph nodes. According to several publications IDO over-expression is associated with poor prognosis in cancer [Okamoto et al 2005; Brandacher et al, 2006]. T cells appear to be preferentially sensitive to IDO activation, such that when starved for tryptophan they cannot divide and as a result cannot become activated by an antigen presented to them. Munn and Mellor and their colleagues, revealed that IDO modulates immunity by suppressing T-cell activation and by creating peripheral tolerance to tumor antigens (Mellor and Munn, 2004). These mechanism encompass the subversion of immune cells recruited by the tumor cell to its immediate microenvironment or to the tumor-draining lymph nodes Here the tumor antigens that were scavenged by antigen-presenting cells are cross-presented to the adaptive immune system. In addition to being directly tolerogenic, mature DCs have the capacity to expand regulatory Tcells (Tregs) [Moser 2003].

Beside tryptophan catabolism the conversion of arginine is increased in a tumor-conditioned microenvironment, and numerous reports indicate a role for the activation of arginases during tumor growth and development. In tumorinfiltrating myeloid cells, arginine is converted by arginase I (ARG1), arginase II (ARG2) to urea and ornithine and oxidized by the inducible form of nitric oxide synthase (NOS2) to citrulline and nitric oxide (NO).

Increased ARG activity is frequently observed in patients with colon, breast, lung, and prostate cancer [Cederbaum 2004] correlating with the over-expression of ARG and NOS found in prostate cancers [Keskinege et al. 2001, Aaltoma et al. 2001, Wang et al. 2003]. It was shown that ARG activity in infiltrating macrophages impairs antigen-specific T cell responses and the expression of the CD3 receptor. Moreover the cumulative activity of ARG and NOS in tumor associated myeloid cells can generate inhibitory signals to antigen-specific T lymphocytes that eventually lead to apoptosis [Bronte 2003 a; 2003b].

Both, the IDO and the ARG related mechanism merge at the point of sensing the depleted concentration of the respective amino acid concentration. During amino acid deprivation, the eIF2 kinase EIF2AK4 called general control nonderepressible 2 (GCN2) is interacting with the intracellular accumulating deacylated tRNA. As a consequence the GCN2 is assumed to change from an auto-inhibited to an active conformation and further activate by autophosphorylation. Then the only known substrate protein eIF2a becomes phosphorylated and as a consequence the complex for translation initiation is inhibited [Harding et al. 2000,]. This diminishes the general Cap-dependent translation initiation and by this the corresponding protein production. On the other hand this induces the specific expression of stress related target genes mainly by cap-independent initiation via the activating transcription factor 4 (ATF4). By expressing the respective stress response proteins, e.g. enzymes in the in amino acid metabolism, the cell tries to compensate the particular cell stress [Wek et al. 2006]. If the stress persists, the same pathway will switch to promoting cell death via transcription of the pro-apoptotic transcription factor, CCAAT/enhancer-binding protein homologous protein (CHOP) [Oyadomari 2004]. It was shown that tryptophan starvation triggers a GCN2-dependent stress signaling pathway. In T cells altering eIF2aphosphorylation and translational initiation leading to a cell growth arrest (Munn et al. 2005). Sharma, et al. [2007] published on the direct IDO-induced and GCN2-dependent activation of mature Tregs. Analogously Fallarino et al [2006] found a GCN2-dependent conversion of CD4+CD25− cells to CD25+FoxP3+ Tregs producing IL-10 and TGFβ. Rodriguez et al. [2007] identified that activation of the GCN2 pathway via tryptophan or arginine depletion in combination with TCR signaling leads to CD3ζ chain down regulation, cell cycle arrest and anergy.

Importantly the GCN2 pathway is not only important for the tumoral immune escape but also plays an active role in modulating tumor survival directly. Ye et al [2010] found that the aforementioned transcription factor ATF4 is overexpressed inhuman solid tumors, suggesting an important function in tumour progression. Amino acid and glucose deprivation are typical stresses found in solid tumours and activated the GCN2 pathway to up-regulate ATF4 target genes involved in amino acid synthesis and transport. GCN2 activation/overexpression and increased phospho-eIF2a were observed in human and mouse tumors compared with normal tissues and abrogation of ATF4 or GCN2 expression significantly inhibited tumor growth in vivo. It was concluded that the GCN2-eIF2a-ATF4 pathway is critical for maintaining metabolic homeostasis in tumor cells.

Over all the present biology makes an interference with the ARG/IDO pathway attractive for braking up the tumoral immune escape by adaptive mechanism. The interference of GCN2 function is here of particular interest as it is a merging point of the two pathways, the IDO and ARG, as well as it provides additional opportunities to impede with the tumor metabolism directly.

Several pathway inhibitors are already considered as immune modulators. These inhibitors address mainly the enzymatic function of the IDO or ARG proteins (Muller and Scherle, 2006). The application of the arginase inhibitor, N-hydroxy-nor-L-Arg blocks growth of s.c. 3LL lung carcinoma in mice [Rodriguez 2004]. The NO-donating aspirins like NCX 4016 (2-(acetyloxy)-benzoic acid 3-(nitrooxymethyl)phenyl ester) have been reported to interfere with the inhibitory enzymatic activities of myeloid cells. Orally administered NO aspirin normalized the immune status of tumor-bearing hosts, increased the number and function of tumor-antigen-specific T lymphocytes, and enhanced the preventive and therapeutic effectiveness of the antitumor immunity elicited by cancer vaccination (DeSanto 2005).

The substrate analogue 1 methyl-tryptophan (1MT) and related molecules have been used widely to target IDO in the cancer context and other settings. Studies by Friberg et al. (2002) and Uyttenhove et al. (2003) demonstrated that 1MT can limit the growth of tumors over-expressing IDO. However 1MT was unable to elicit tumor regression in several tumor models, suggesting only modest antitumor efficacy when IDO inhibition was applied as a monotherapy. In contrast, the combinatory treatment with 1MT and a variety of cytotoxic chemotherapeutic agents elicited regression of established MMTV-neu/HER2 tumors, which responded poorly to any single-agent therapy [Muller et al 2005a].

Immunodepletion of CD4+ or CD8+ T cells from the mice before treatment abolished the combinatorial efficacy observed in this model, confirming the expectation that 1MT acted indirectly through activation of T cell-mediated antitumor immunity. Important evidence that IDO targeting is essential to 1MT action was provided by the demonstration that 1MT lacks antitumor activity in mice that are genetically deficient for IDO [Hou et al., 2007]

The inhibition of GCN2 would enable to combine the two pathway branches of amino acid starvation induced immunoediting and would reduce the options for the tumor to circumvent the inhibition of either branch. Moreover, as detailed above, the GCN2 inhibition provides the opportunity for interfering with the tumor metabolism at the same time what may enhance the efficacy of a monotherapy or a combination therapy with other anticancer approaches.

As mentioned above, the eIF2 kinase GCN2 is activated by interacting with deacylated tRNA that is accumulating as direct consequence of nutritional deprivation stress. Other cellular stress factors like UV irridation, redox stress or proteasome inhibition can induce GCN2 activation indirectly [Wek et al 2006]. In all known cases eIF2a becomes phosphorylated and this induces the specific expression of stress related target genes mainly by cap-independent initiation via the activating transcription factor 4 (ATF4). Mitsuda et al (2007) showed that presenilin-1 is induced by activating transcription factor 4 (ATF4), regulated by GCN2. Accumulation of amyloid-β (Aβ), which is generated from amyloid precursor protein by γ-secretase, in cerebral cortex is common and critical incident in Alzheimer disease.

Specifically, presenilin is an essential for γ-secretase activity. Ohata et al. (2010) describe a role of GCN2-eIF2α-ATF4 signaling in the regulation of γ-secretase activity in autophagy impaired cells: The impairment of the autophagy-lysosomal system may cause amino acid imbalance in the cell because autophagy is required for maintenance of amino acid level. The autophagy-lysosomal system is discussed as a vital modulator of γ-secretase activity through GCN2, leading to Aβ accumulation in autophagy deterioration, which may be a possible therapeutic target for reducing Aβ production. γ-Secretase plays an important role in the development of Alzheimer disease (AD). γ-Secretase activity is enriched in autophagic vacuoles and it augments amyloid-β (Aβ) synthesis.

Senile plaques are primarily composed of β-amyloid peptides (Aβ) derived from amyloid precursor protein (APP) that has undergone proteolytic processing by β-secretase (BACE-1) and γ-secretase. O'Connor et al. (2008) found that BACE-1 levels are translationally increased by phosphorylation of eIF2α.

Inhibition of GCN2 under such disease conditions that promote activation of γ-secretase or induction of BACE-1 with consequence of accumulation of Aβ and plaque formation in the brain would provide a valuable avenue to temper or even stop the progression of neurodegenerative diseases.

It was described that persistent, not acute, parasite or viral infections are associated to the establishment of immune privileged conditions of even immune competent host towards the infectious organism or particles. This has been associated to the local induction of IDO expression. Makala et al (J Infect Dis. 2011 Mar. 1; 203(5):715-25) show that cutaneous *Leishmania major* infection stimulated expression of the immune regulatory enzyme indoleamine 2,3 dioxygenase (IDO) in local lymph nodes. Induced IDO attenuated the T cell stimulatory functions of dendritic cells and suppressed local T cell responses to exogenous and nominal parasite antigens. IDO ablation reduced local inflammation and parasite burdens, as did pharmacologic inhibition of IDO in mice with established infections. de Souza Sales (*Clin Exp Immunol.* 2011 August; 165(2):251-63) corroborated the role of indoleamine 2,3-dioxygenase in lepromatous leprosy immunosuppression. Boasso et al (*Blood,* 2007 Apr. 15; 109(8):3351-9) found that HIV inhibits CD4+ T-cell proliferation by inducing indoleamine 2,3-dioxygenase in plasmacytoid dendritic cells and that in vitro inhibition of IDO results in increased CD4(+) T-cell proliferative response in PBMCs from HIV-infected patients Inhibitor drugs of the IDO/GCN2 pathway could be used to enhance host immunity to chronic and persistent infections.

LITERATURE

1. Aaltoma, S. H., P. K. Lipponen, and V. M. Kosma. 2001. Inducible nitric oxide synthase (iNOS) expression and its prognostic value in prostate cancer. Anticancer Res. 21:3101-3106.
2. Brandacher, G.; Perathoner, A.; Ladurner, R.; Schneeberger, S.; Obrist, P.; Winkler, C.; Werner, E. R.; Werner-Felmayer, G.; Weiss, H. G.; Gobel, G.; Margreiter, R.; Konigsrainer, A.; Fuchs, D.; Amberger, A. Prognostic value of indoleamine 2,3-dioxygenase expression in colorectal cancer: effect on tumorinfiltrating T cells. Clin. Cancer Res. 2006, 12, 1144-1151.
3. Bronte V, Zanovello P. (2005). Regulation of immune responses by L-arginine metabolism. Nat Rev Immunol 5: 641-654.
4. Bronte, V., P. Serafini, C. De Santo, I. Marigo, V. Tosello, A. Mazzoni, D. M. Segal, C. Staib, M. Lowel, G. Sutter, et al. 2003a. IL-4-induced arginase 1 suppresses alloreactive T cells in tumor-bearing mice. J. Immunol. 170: 270-278.
5. Bronte, V., P. Serafini, A. Mazzoni, D. M. Segal, and P. Zanovello. 2003b. L-arginine metabolism in myeloid cells controls T-lymphocyte functions. Trends Immunol. 24:302-306
6. Carmela De Santo, Paolo Serafini, Ilaria Marigo, Luigi Dolcetti, Manlio Bolla, § Piero Del Soldato, Cecilia Melani, Cristiana Guiducci, Mario P. Colombo, Manuela lezzi, Piero Musiani, Paola Zanovello, and Vincenzo Bronte. Nitroaspirin corrects immune dysfunction in tumor-bearing hosts and promotes tumor eradication by cancer vaccination. Proc Natl Acad Sci USA. 2005 Mar. 15; 102(11): 4185-4190
7. Cederbaum, S. D., H. Yu, W. W. Grody, R. M. Kern, P. Yoo, and R. K. Iyer. 2004. Arginases I and II: do their functions overlap? Mol. Genet. Metab. 81:S38-44.
8. T. O'Connor, K. R. Sadleir, E. Maus, R. A. Velliquette, J. Zhao, S. L. Cole, W. A. Eimer, B. Hitt, L. A. Bembinster, S. Lammich, S. F. Lichtenthaler, S. S. Hebert, S. B. De, C. Haass, D. A. Bennett, R. Vassar, Phosphorylation of the translation initiation factor eIF2alpha increases BACE1 levels and promotes amyloidogenesis. Neuron, 60 (2008), pp. 988-1009
9. Dey, M., Cao, C., Sicheri, F. and T. E. Dever. Conserved Intermolecular Salt Bridge Required for Activation of Protein Kinases PKR, GCN2, and PERK. JBC 282(9): 6653, 2007.
10. Dunn, G. P.; Old, L. J.; Schreiber, R. D. The immunobiology of cancer immunosurveillance and immunoediting. Immunity 2004, 21, 137-148.
11. Fallarino, F. U. Grohmann, S. You, B. C. et al. The combined effects fo tryptophan starvation and tryptophan catabolites down-regulate T cell receptor zeta-chain and induce a regulatory phenotype in naïve T cells. J. Immunol. 176:6752, 2006.
12. Friberg M, Jennings R, Alsarraj M, Dessureault S, Cantor A, Extermann M et al. (2002). Indoleamine 2,3-dioxygenase contributes to tumor cell evasion of T cell-mediated rejection. Int. J Cancer 101: 151-155
13. Harding H P, Novoa I, Zhang Y, Zeng H, Wek R, Schapira M, Ron D. Regulated translation initiation controls stress-induced gene expression in mammalian cells. Mol Cell. 2000 November; 6(5):1099-108.
14. Hou D Y, Muller A J, Sharma M D, DuHadaway J, Banerjee T, Johnson M et al. (2007). Inhibition of indoleamine 2,3-dioxygenase in dendritic cells by stereoisomers of 1-methyl-tryptophan correlates with antitumor responses. Cancer Res 67: 792-801.
15. Keskinege, A., S. Elgun, and E. Yilmaz. 2001. Possible implications of arginase and diamine oxidase in prostatic carcinoma. Cancer Detect. Prev. 25:76-79.
16. Mellor A L, Munn D H. (2004). IDO expression by dendritic cells: tolerance and tryptophan catabolism. Nat Rev Immunol 4: 762-774.
17. Mitsuda T, Hayakawa Y, Itoh M, Ohta K, Nakagawa T. ATF4 regulates gamma-secretase activity during amino acid imbalance, Biochem Biophys Res Commun. 2007 Jan. 19; 352(3):722-7.
18. Moser, M. Dendritic cells in immunity and tolerance-do they display opposite functions? Immunity 2003, 19, 5-8.
19. Muller, A. J. and P. A. Scherle. Targeting the mechanisms of tumoral immune tolerance with small-molecule inhibitors. Nat. Rev. Cancer. 6:613, 2006.
20. Muller A J, Prendergast G C. (2007). Indoleamine 2,3-dioxygenase in immune suppression and cancer. Curr Cancer Drug Targets 7: 31-40.
21. Muller A J, DuHadaway J B, Sutanto-Ward E, Donover P S, Prendergast G C. (2005a). Inhibition of indoleamine 2,3-dioxygenase, an immunomodulatory target of the tumor suppressor gene Bin1, potentiates cancer chemotherapy. Nature Med 11: 312-319.
22. Muller A J, Malachowski W P, Prendergast G C. (2005b). Indoleamine 2,3-dioxygenase in cancer: targeting pathological immune tolerance with small-molecule inhibitors. Expert Opin Ther Targets 9: 831-849.
23. Munn, D. H., M. D. Sharma, B. Baban, H. P. Harding, Y. Zhang, D. Ron, A. L. Mellor. GCN2 kinase in T cells mediates proliferative arrest and anergy induction in response to indoleamine 2,3-dioxygenase. Immunity. 22:633, 2005
24. Ohta K, Mizuno A, Ueda M, Li S, Suzuki Y, Hida Y, Hayakawa-Yano Y, Itoh M, Ohta E, Kobori M, Nakagawa T. Autophagy impairment stimulates PS1 expression and gamma-secretase activity. Autophagy. 2010; 6(3):345-52
25. Okamoto, A.; Nikaido, T.; Ochiai, K.; Takakura, S.; Saito, M.; Aoki, Y.; Ishii, N.; Yanaihara, N.; Yamada, K.; Takikawa, O.; Kawaguchi, R.; Isonishi, S.; Tanaka, T.; Urashima, M. Indoleamine 2,3-dioxygenase serves as a marker of poor prognosis in gene expression profiles of serous ovarian cancer cells. Clin. Cancer Res. 2005, 11, 6030-6039.
26. Oyadomari S, Mori M. Roles of CHOP/GADD153 in endoplasmic reticulum stress. Cell Death Differ. 2004 April; 11(4):381-9.
27. G C Prendergast, Immune escape as a fundamental trait of cancer: focus on IDO. Oncogene (2008) 27, 3889-3900
28. Popovic P J, Zeh III H J, Ochoa J B. (2007). Arginine and immunity. J Nutr 137: 1681S-1686 S.

29. Rodriguez, P. C., D. G. Quiceno, J. Zabaleta, B. Ortiz, A. H. Zea, M. B. Piazuelo, A. Delgado, P. Correa, J. Brayer, E. M. Sotomayor, S. Antonia, J. B. Ochoa, and A. C. Ochoa. Arginase I Production in the Tumor Microenvironment by Mature Myeloid Cells Inhibits T-Cell Receptor Expression and Antigen-Specific T-Cell Responses. Canc. Res. 64:5839, 2004
30. Rodriguez, P. C., D. G. Quiceno, and A. C. Ochoa. L-arginine availability regulates T-lymphocyte cell-cycle progressión. Blood. 109:1568, 2007.
31. Shankaran, V.; Ikeda, H.; Bruce, A. T.; White, J. M.; Swanson, P. E.; Old, L. J.; Schreiber, R. D. IFNgamma and lymphocytes prevent primary tumour development and shape tumour immunogenicity. Nature 2001, 410, 1107-1111.
32. Sharma, M. D., B. Baban, P. Chandler, D-Y. Hou, N. Singh, H. Yagita, M. Azuma, B. R. Blazar, A. L. Mellor, and D. H. Munn. Plasmacytoid dendritic cells from mouse tumor-draining lymph nodes directly activate mature Tregs via indoleamine 2,3-dioxygenase. J. Clin. Invest. 117:2570, 2007.
33. Uyttenhove C, Pilotte L, Theate I, Stroobant V, Colau D, Parmentier N et al. (2003). Evidence for a tumoral immune resistance mechanism based on tryptophan degradation by indoleamine 2,3-dioxygenase. Nat Med 9: 1269-1274
34. Wang, J., M. Torbenson, Q. Wang, J. Y. Ro, and M. Becich. 2003. Expression of inducible nitric oxide synthase in paired neoplastic and non-neoplastic primary prostate cell cultures and prostatectomy specimen. Urol. Oncol. 21:117-122.
35. Wek R C, Jiang H Y, Anthony T G. Coping with stress: eIF2 kinases and translational control. Biochem Soc Trans. 2006 February; 34 (Pt 1):7-11.
36. Ye J, Kumanova M, Hart L S, Sloane K, Zhang H, De Panis D N, Bobrovnikova-Marjon E, Diehl J A, Ron D, Koumenis C. The GCN2-ATF4 pathway is critical for tumour cell survival and proliferation in response to nutrient deprivation. EMBO J. 2010 Jun. 16; 29(12): 2082-96.

In particular, the present invention relates to compounds and to the use of compounds in which the inhibition, regulation and/or modulation of signal transduction by GCN2 plays a role.

The synthesis of small compounds which specifically inhibit, regulate and/or modulate signal transduction by immune-modulatory or stress response kinases in particular GCN2, is therefore desirable and an aim of the present invention.

Moreover, aim of this invention is the synthesis of new compounds for the prevention and treatment of neoplastic malignancies including, but without being limited to, solid tumor cancers, cancers of the lymphatic or blood system, of neurodegenerative diseases and chronic infections.

It has been found that the compounds according to the invention and salts thereof have very valuable pharmacological properties while being well tolerated.

The compounds of the formula I can furthermore be used for the isolation and investigation of the activity or expression of GCN2. In addition, they are particularly suitable for use in diagnostic methods for diseases in connection with unregulated or disturbed GCN2 activity.

Compounds of formula I can also inhibit tyrosine kinases FMS (CSF1R), GSK3α, GSK3β, FLT3 or FLT4 or combinations of these kinases, preferentially in addition to inhibitory activity towards GCN2.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, Blood 100, 1532-1542 (2002); Stirewalt et al., Nat. Rev. Cancer, 3, 650-665 (2003). Activating mutations in FLT3 mutations have been associated with a poor prognosis (Malempati et al., Blood, 104, 11 (2004). FLT3 inhibitors are being developed and some have shown promising clinical effects against AML (Levis et al Int. J. Hematol, 52, 100-107 (2005).

It has been reported that some of small-molecule FLT3 inhibitors are effective in inducing apoptosis in cell lines with FLT3-activating mutations and prolonging survival of mice that express mutant FLT3 in their bone marrow cells (Levis et al, Blood, 99, 3885-3891 (2002); Kelly et al, Cancer Cell, 1, 421-432 (2002); Weisberg et al, Cancer Cell, 1, 433-443 (2002); Yee et al, Blood, 100, 2941-2949 (2002).

US patent application 20090054358 describes Flt3 inhibitors for immune suppression and in particular for the treatment of immune related disorders like organ rejection, bone marrow transplant rejection, non-myeloablative bone marrow transplant rejection, ankylosing spondylitis, arthritis, aplastic anemia, Behcet's disease, type 1 diabetes mellitus, graft-versus-host disease, Graves' disease, autoimmune hemolytic anemia, Wegener's granulomatosis, hyper IgE syndrome, idiopathic thrombocytopenia purpura, rheumatoid arthritis, Crohn's disease, multiple sclerosis, Myasthenia gravis, psoriasis, and lupus, among other autoimmune diseases. Flt3 Inhibitors might also be used to treat neurological disorder as neurodegenerative disease, for example a disease caused by axonal degeneration. Neurodegenerative diseases include, for example, multiple sclerosis; demyelinating core disorders, such as multiple sclerosis, acute transverse myelitis without being limited thereto.

Scott et al (Bioorg. Med Chem Let. (2008) 18 (17) p 4794) describe CSF-1R inhibitors for the treatment of cancer. CSF-1R is a member of the class III receptor tyrosine kinases. Colony stimulatory factor 1 (CSF-1), also known as macrophage/monocyte colony stimulatory factor (M-CSF), binds to CSF-1R, resulting in dimerization, autophosphorylation, and activation of signal transduction.) CSF-1/CSF-1R signaling is essential for normal monocyte development. In cancer, pro-tumorigenic macrophages have been identified and linked to poor prognosis in breast, ovarian, and prostate cancers. Elevated levels of CSF-1 and CSF-1R have been reported in several tumor types, including breast, ovarian, and endometrial cancers, and have also been linked to invasion and metastasis. Inhibition of CSF-1R activity could therefore have multiple effects on the tumor through reduction in the levels of tumor-associated macrophages (TAMs) and have direct effects on the tumor itself (C. E. Lewis, J. W. Pollard, Cancer Res., 66 (2006), p. 605; I. Bingle, N. et al., J. Pathol., 196 (2002), p. 254; B. M. Kacinski, Ann. Med., 27 (1995), p. 79; E. Garwood et al. J Clin Oncol 26: 2008).

Su J L et al. (Cancer Cell. 2006 March; 9(3):209-23) report that the VEGF-C/Flt-4 axis promotes invasion and metastasis of cancer cells. Flt-4, a VEGF receptor, is activated by its specific ligand, VEGF-C. The resultant signaling pathway promotes angiogenesis and/or lymphangiogenesis. VEGF-C/Flt-4 axis enhances cancer cell mobility and invasiveness and contributes to the promotion of cancer cell metastasis. Examination of tumor tissues from various types of cancers revealed high levels of Flt-4 and VEGF-C expression that correlated closely with clinical metastasis and patient survival. Inhibition of Flt-4 kinase could reduce the invasive capacity in different types of cancer Combining the inhibitory specificity towards GCN2 with that towards FMS (CSF1R), FLT3 or FLT4 or combinations of these kinases can be of particular advantages for the treatment of neoplastic malignancies at different disease stages. It could combine the effects of stimulating the immune response towards cancer/tumor cells, to reduce the levels of tumor-associated macrophages as well as the invasive capacity of cancers for metastasis formation. In a further aspect the combination of inhibitory activities on GCN2 particularly with inhibition of FLT3 could be advantageous for the treatment of neurodegenerative disorders as it could synergize suppressive effects on inflammatory processes with the modulation of protein deposites generation in the brain. In another aspect the combination of inhibitory activities on GCN2 particularly with inhibition of FLT3 could provide advantages for modulating the immune response to treat immune related disorders and inflammatory or autoimmune diseases.

In a further embodiment the present invention specifically relates to compounds of the formula I which inhibit, regulate and/or modulate signal transduction by GCN2, FMS (CSF1R), GSK3α, GSK3β, FLT3 or FLT4 or combinations of these kinases, to compositions which comprise these compounds, and to processes for the use thereof for the treatment of diseases and complaints that are -induced or modulated by GCN2, FMS (CSF1R), GSK3α, GSK3β, FLT3 or FLT4 or combinations of these kinases.

Further aim of this invention is the synthesis of new compounds for the prevention and treatment of neoplastic malignancies including, but without being limited to, solid tumor cancers, cancers of the lymphatic or blood system, of neurodegenerative diseases, immune related disorders like arthritis, psoriasis, lupus, multiple sclerosis or other autoimmune diseases as well as chronic infections.

The compounds of the formula I can furthermore be used for the isolation and investigation of the activity or expression of GCN2, GSK3α, GSK3β, FMS (CSF1R), FLT3 or FLT4. In addition, they are particularly suitable for use in diagnostic methods for diseases in connection with unregulated or disturbed GCN2, FMS (CSF1R), GSK3α, GSK3β, FLT3 or FLT4 activity. The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

PRIOR ART

Other bicyclic aromatic heterocycles are described in WO 2005/012307 A1, WO 2006/045828 and in WO 2006/075023 A2.

Aminopurines are described in WO 2006/076595 A1.

SUMMARY OF THE INVENTION

The invention relates to compounds of the formula I

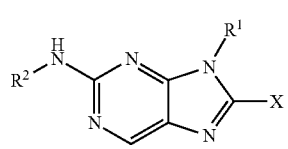

in which
X denotes H, $CH_3$ or $NH_2$,
$R^1$ denotes Ar or Het,
$R^2$ denotes pyrazolyl, pyrrolidinyl or cyclopentyl, each of which is unsubstituted or monosubstituted by A, Hal, $[C(R^3)_2]_pOR^3$, $O[C(R^3)_2]_pOR^3$, $[C(R^3)_2]_pN(R^3)_2$, $[C(R^3)_2]_pAr$, $[C(R^3)_2]_pHet^1$, CN, $[C(R^3)_2]_pCOOR^3$, Cyc, $CO[C(R^3)_2]_pN(R^3)_2$, $CO[C(R^3)_2]_pHet^1$, $NR^3COA$, $NR^3SO_2A$, $SO_2N(R^3)_2$, $S(O)_nA$, $COHet^1$, $O[C(R^3)_2]_mN(R^3)_2$, $O[C(R^3)_2]_pHet^1$, NHCOOA, $NHCON(R^3)_2$, $NHCOO[C(R^3)_2]_mN(R^3)_2$, $NHCOO[C(R^3)_2]_pHet^1$, $NHCONH[C(R^3)_2]_mN(R^3)_2$, $NHCONH[C(R^3)_2]_pHet^1$, $OCONH[C(R^3)_2]_mN(R^3)_2$, $OCONH[C(R^3)_2]_pHet^1$ or $C(O)R^3$,
$R^3$ denotes H or unbranched or branched alkyl with 1-4 C-atoms,
Ar denotes phenyl, which is unsubstituted or mono-, di- or trisubstituted by Hal, A, $[C(R^3)_2]_pOR^3$, $O[C(R^3)_2]_pOR^3$, $[C(R^3)_2]_pN(R^3)_2$, $O[C(R^3)_2]_pN(R^3)_2$, $[C(R^3)_2]_pHet^1$, $NO_2$, CN, $[C(R^3)_2]_pCOOR^3$, $O[C(R^3)_2]_pCOOR^3$, $CONH_2$, CONA, $CONA_2$, $NR^3COA$, $NR^3SO_2A$, $SO_2N(R^3)_2$, $S(O)_nA$, $COHet^1$, $O[C(R^3)_2]_pHet^1$, NHCOOA, $NHCON(R^3)_2$, $NHCOO[C(R^3)_2]_mN(R^3)_2$, $NHCOO[C(R^3)_2]_pHet^1$, $NHCONH[C(R^3)_2]_mN(R^3)_2$, $NHCONH[C(R^3)_2]_pHet^1$, $OCONH[C(R^3)_2]_mN(R^3)_2$, $OCONH[C(R^3)_2]_pHet^1$, $S(O)_nHet^1$, CHO and/or COA,
Het denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, pyrazinyl, indolyl, isoindolyl, indolinyl, benzimidazolyl, indazolyl, quinolyl, isoquinolyl, benzoxazolyl, 1,3-benzodioxolyl, benzothiophenyl, benzofuranyl, imidazopyridyl, dihydroindolyl, quinoxalinyl, benzo[1,2,5]thiadiazolyl or furo[3,2-b]pyridyl, each of which is unsubstituted or mono- or disubstituted by Hal, A, $[C(R^3)_2]_pOR^3$, $O[C(R^3)_2]_pOR^3$, $[C(R^3)_2]_pN(R^3)_2$, $O[C(R^3)_2]_pN(R^3)_2$, $[C(R^3)_2]_pHet^1$, $NO_2$, CN, $[C(R^3)_2]_pCOOR^3$, $O[C(R^3)_2]_pCOOR^3$, $CON(R^3)_2$, $NR^3COA$, $NR^3SO_2A$, $SO_2N(R^3)_2$, $S(O)_nA$, $COHet^1$, $O[C(R^3)_2]_pHet^1$, NHCOOA, $NHCON(R^3)_2$, $NHCOO[C(R^3)_2]_mN(R^3)_2$, $NHCOO[C(R^3)_2]_pHet^1$, $NHCONH[C(R^3)_2]_mN(R^3)_2$, $NHCONH[C(R^3)_2]_pHet^1$, $OCONH[C(R^3)_2]_mN(R^3)_2$, $OCONH[C(R^3)_2]_pHet^1$, $S(O)_nHet^1$, CHO, COA, =S and/or =O,
$Het^1$ denotes pyrazolyl, pyridyl, pyrazinyl, indolyl, dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, [1,3]dioxolanyl, tetrahydropyranyl or piperazinyl, each of which is unsubstituted or mono- or disubstituted by Hal, A, $[C(R^3)_2]_pOR^3$, $O[C(R^3)_2]_pOR^3$, $[C(R^3)_2]_pN(R^3)_2$, $[C(R^3)_2]_pHet^2$, $NO_2$, CN, $[C(R^3)_2]_pCOOR^3$, $O[C(R^3)_2]_pCOOR^3$, $CON(R^3)_2$, $NR^3COA$, $NR^3SO_2A$, $SO_2N(R^3)_2$, $S(O)_nA$, $COHet^2$, $O[C(R^3)_2]_mN(R^3)_2$, $O[C(R^3)_2]_pHet^2$, NHCOOA, $NHCON(R^3)_2$, $NHCOO[C(R^3)_2]_mN(R^3)_2$, $NHCOO[C(R^3)_2]_pHet^2$, $NHCONH[C(R^3)_2]_mN(R^3)_2$, $NHCONH[C(R^3)_2]_pHet^2$, $OCONH[C(R^3)_2]_mN(R^3)_2$, $OCONH[C(R^3)_2]_pHet^2$, $S(O)_nHet^2$, CHO, COA, =S and/or =O,
$Het^2$ denotes pyrrolidinyl, azetidinyl, azoxetanyl, tetrahydroimidazolyl, tetrahydropyrazolyl, tetrahydrofuranyl, piperidinyl, morpholinyl, tetrahydropyranyl or piperazinyl, each of which is unsubstituted or mono- or disubstituted by Hal, A, OA, CN, COOA, $CONH_2$, $S(O)_nA$, $S(O)_nAr$, COA and/or =O,
Cyc denotes cycloalkyl with 3-7 C-atoms, which is unsubstituted or monosubstituted by $NH_2$, A denotes unbranched or branched alkyl with 1-6 C-atoms, wherein one or two non-adjacent CH- and/or $CH_2$-groups may be replaced by N-, O- and/or S-atoms and wherein 1-7H-atoms may be replaced by F or Cl,
Hal denotes F, Cl, Br or I,
n denotes 0, 1 or 2,
m denotes 1, 2 or 3,
p denotes 0, 1, 2, 3 or 4,
and pharmaceutically usable solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds.

The invention also relates to the solvates of the salts of the compounds of formula I, e.g. the mono- or dihydrate of the hydrochloride.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alcoholates.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically usable salts, solvates, tautomers and stereoisomers thereof, characterised in that
a) wherein in formula I X denotes H,
a compound of the formula II

in which $R^1$ and $R^2$ have the meanings indicated in Claim 1, is reacted with trimethyl- or triethylorthoformate
or
b) wherein in formula I X denotes $NH_2$,
a compound of the formula II is reacted with CN—Br
and/or
a base or acid of the formula I is converted into one of its salts.

Above and below, the radicals $R^1$ and $R^2$ have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A denotes e.g. $CH_2OCH_3$, $CH_2CH_2OH$, $OCH_2CH_2NH_2$, $CH_2NHCH_3$ or $NHCH_2CH_3$.

Cycloalkyl with 3-7 C-atoms preferably denotes cyclopropyl, cyclobutyl, cyclopentyl, cyclohexyl or cycloheptyl.
$R^1$ preferably denotes Ar.
$R^2$ preferably denotes pyrazolyl, pyrrolidinyl or cyclopentyl, each of which is unsubstituted or monosubstituted by A, $[C(R^3)_2]_pAr$, $[C(R^3)_2]_pHet^1$, Cyc, $[C(R^3)_2]_pOR^3$, $CO[C(R^3)_2]_pN(R^3)_2$ or $CO[C(R^3)_2]_pHet^1$.
$R^3$ preferably denotes H or alkyl having 1, 2, 3 or 4 C atoms, particularly preferably H or methyl.
Ar denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonyl-phenyl, o-, m- or p-(N,N-dimethylamino)phenyl, o-, m- or p-(N,N-dimethyl-aminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylamino-phenyl, 2,3-diaminophenyl, 2,3,4-, 2,3,5-, 2,3,6-, 2,4,6- or 3,4,5-tri-chlorophenyl, 2,4,6-trimethoxyphenyl, 2-hydroxy-3,5-dichlorophenyl, p-iodo-phenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, which is unsubstituted or mono-, di- or trisubstituted by Hal, A, $[C(R^3)_2]_pOR^3$, $O[C(R^3)_2]_pOR^3$, $[C(R^3)_2]_pHet^1$, $CONH_2$, CONA and/or $CONA_2$.

Het preferably denotes pyrazolyl, pyridyl, indolyl, isoindolyl, indolinyl, quinolyl or isoquinolyl, each of which is unsubstituted or mono- or disubstituted by A and/or =O.

Furthermore, Het preferably denotes pyrazolyl, pyridyl, indolyl, isoindolyl, quinolyl or isoquinolyl, each of which is unsubstituted or mono- or disubstituted by A, or Het denotes indolinyl, which is unsubstituted or mono- or disubstituted by A and/or =O.

$Het^1$ preferably denotes pyrazolyl, pyridyl, pyrrolidinyl, piperidinyl, morpholinyl, tetrahydropyranyl or piperazinyl, each of which is unsubstituted or mono- or disubstituted by A and/or $[C(R^3)_2]_pHet^2$, $Het^2$ preferably denotes pyrrolidinyl, azetidinyl, azoxetanyl, tetrahydroimidazolyl, tetrahydropyrazolyl, tetrahydrofuranyl, piperidinyl, morpholinyl, tetrahydropyranyl or piperazinyl, each of which is unsubstituted or mono- or disubstituted by A.

$Het^2$ furthermore preferably denotes pyrrolidinyl, piperidinyl, morpholinyl or piperazinyl, each of which is unsubstituted or monosubstituted by A.

$Het^2$ very particularly preferably denotes piperidinyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Id, which conform to the formula I and in which the radicals not designated in greater detail have the meaning indicated for the formula I, but in which in Ia $R^2$ denotes pyrazolyl, pyrrolidinyl or cyclopentyl, each of which is unsubstituted or monosubstituted by A, $[C(R^3)_2]_p Ar$, $[C(R^3)_2]_p Het^1$, Cyc, $[C(R^3)_2]_p OR^3$, $CO[C(R^3)_2]_p N(R^3)_2$ or $CO[C(R^3)_2]_p Het^1$;

in Ib Ar denotes phenyl, which is unsubstituted or mono-, di- or trisubstituted by Hal, A, $[C(R^3)_2]_p OR^3$, $O[C(R^3)_2]_p OR^3$, $[C(R^3)_2]_p Het^1$, $CONH_2$, CONA and/or $CONA_2$;

in Ic Het denotes pyrazolyl, pyridyl, indolyl, isoindolyl, indolinyl, quinolyl or isoquinolyl, each of which is unsubstituted or mono- or disubstituted by A and/or $=O$;

in Ic $Het^1$ denotes pyrazolyl, pyridyl, pyrrolidinyl, piperidinyl, morpholinyl, tetrahydropyranyl or piperazinyl, each of which is unsubstituted or mono- or disubstituted by A and/or $[C(R^3)_2]_p Het^2$;

in Id $R^1$ denotes Ar or Het,

X denotes H, $CH_3$ or $NH_2$, $R^2$ denotes pyrazolyl, pyrrolidinyl or cyclopentyl, each of which is unsubstituted or monosubstituted by A, $[C(R^3)_2]_p Ar$, $[C(R^3)_2]_p Het^1$, Cyc, $[C(R^3)_2]_p OR^3$, $CO[C(R^3)_2]_p N(R^3)_2$ or $CO[C(R^3)_2]_p Het^1$, $R^3$ denotes H or unbranched or branched alkyl with 1-4 C-atoms, Ar denotes phenyl, which is unsubstituted or mono-, di- or trisubstituted by Hal, A, $[C(R^3)_2]_p OR^3$, $O[C(R^3)_2]_p OR^3$, $[C(R^3)_2]_p Het^1$, $CONH_2$, CONA and/or $CONA_2$, Het denotes pyrazolyl, pyridyl, indolyl, isoindolyl, indolinyl, quinolyl or isoquinolyl, each of which is unsubstituted or mono- or disubstituted by A and/or $=O$, $Het^1$ denotes pyrazolyl, pyridyl, pyrrolidinyl, piperidinyl, morpholinyl, tetrahydropyranyl or piperazinyl, each of which is unsubstituted or mono- or disubstituted by A and/or $[C(R^3)_2]_p Het^2$, $Het^2$ denotes pyrrolidinyl, piperidinyl, morpholinyl or piperazinyl, each of which is unsubstituted or monosubstituted by A, A denotes unbranched or branched alkyl with 1-6 C-atoms, wherein one or two non-adjacent CH- and/or $CH_2$-groups may be replaced by N-, O- and/or S-atoms and wherein 1-7H-atoms may be replaced by F or Cl, Hal denotes F, Cl, Br or I, n denotes 0, 1 or 2, m denotes 1, 2 or 3, p denotes 0, 1, 2, 3 or 4 and pharmaceutically acceptable salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise Use can also be made here of variants known per se which are not mentioned here in greater detail.

The starting compounds of the formulae II are generally known. If they are novel, however, they can be prepared by methods known per se.

Compounds of the formula I can preferably be obtained by reacting a compound of the formula II with trimethyl- or triethylorthoformate or with CN—Br.

The reaction is generally carried out under conditions known to the skilled artisan and which are known and suitable for the this reaction.

Depending on the conditions used, the reaction time is between a few minutes and 14 days, the reaction temperature is between about 0° and 140°, normally between 20° and 120°, in particular between about 80° and about 110°. Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitril and water.

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an $NH_2$ group.

Preference is furthermore given to starting materials which carry a hydroxylprotecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphor-sulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, gluco-heptanoate, gluconate, glutamate, glycerophosphate, hemisuccinate, hemi-sulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Exam-pies of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incor-po-ra-tion of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodi-ment of the present invention. An isotope-labelled compound of the formula I can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many com-pounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improve-ment in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, solvates, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds of the formula I and salts, solvates, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxy-ethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt, solvate, tautomer and stereoisomer thereof can be determined as the fraction of the effective amount of the compound according to the invention per se. It can be assumed that similar doses are suitable for the treatment of other conditions mentioned above.

The disclosed compounds of the formula I can be administered in combination with other known therapeutic agents including agents for the treatment of RA (rheumatoid arthritis). As used here, the term "agents for the treatment of RA" relates to any agent which is administered to a patient with RA for the purposes of treating the RA.

The medicaments below are preferably, but not exclusively, combined with the compounds of the formula I:
1. NSAIDs (non-steroidal anti-inflammatory drugs) and analgesics
2. Glucocorticoids (low oral doses)
3. Conventional disease-modifying antirheumatic drugs (DMARDs)
   Methotrexate
   Leflunomide
   Sulfasalazine
   Hydroxycloroquine
   Azathioprine
   Ciclosporin
   Minocycline
   Gold
4. Biologic response modifiers (BRMs)-->target molecules/ immune cells involved in the inflammatory process, and include the following agents:
   TNF inhibitors
      etanercept (Enbrel)
      infliximab (Remicade)
      adalimumab (Humira)
   B-cell-directed therapy
      rituximab (Rituxan)
   T-cell/B-cell coactivation signal inhibitor
      abatacept (Orencia)
   IL-1 receptor antagonist
      anakinra (Kineret)

| | MECHANISM OF ACTION |
|---|---|
| Golimumab | Fully humanized monoclonal antibody to TNF |
| Certolizumab pegol | Anti-TNF agent with just the Fab portion attached to the polyethylene glycol |
| Tocilizumab | Humanized monoclonal anti-IL-6 antibody that binds to the soluble and membrane-expresses IL-6 receptor |
| Ocrelizumab | Humanized-second generation anti-CD20 antibody that depletes B cells |
| Ofatumumab | Human monoclonal anti-CD20 IgG1 antibody |
| Denosumab | Fully humanized monoclonal antibody that binds to and inhibits the receptor activator for nuclear factor-kB ligand |
| TRU-015 | New class of CD20-directed protein therapeutics |
| Oral small molecules (JAK, Syk, MAP kinase inhibitors) | Cytoplasmic targets |
| Tolerogens (dnaJP1) | Immunotherapy based on T-cell tolerization |

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates, tautomers and stereoisomers thereof, including mixtures thereof in all ratios, and at least one further medicament active ingredient.

The invention also relates to a set (kit) consisting of separate packs of
   (a) an effective amount of a compound of the formula I and/or pharmaceutically acceptable salts, solvates, tautomers and stereoisomers thereof, including mixtures thereof in all ratios, and
   (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates, tautomers and stereoisomers thereof, including mixtures thereof in all ratios,
and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions, neurodegenerative conditions, chronic infections or conditions treatable or preventable by inhibition of a kinase or a kinase pathway, in one embodiment, the GCN2 pathway. In another embodiment this relates to conditions treatable or preventable by inhibition of a kinase or a kinase pathway, from the group of GCN2, FMS (CSF1R), FLT3 or FLT4 or combinations thereof. In one embodiment an effective amount of a compound of formula (I) is an amount that inhibits a kinase in a cell, such as, for example, in vitro or in vivo. In some embodiments, the effective amount of the compound of formula (I) inhibits the kinase in a cell by 10%, 20%, 30%, 40%, 50%, 60%, 70%, 80%, 90% or 99%, compared to the activity of the kinase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of immune modulatory and stress response kinase-induced diseases. These diseases include neoplastic malignancies including, but without being limited to, solid tumor cancers, cancers of the lymphatic or blood system, the proliferation of tumour cells, pathological neovascularisation (or angiogenesis) which promotes the growth of solid tumours, neurodegenerative diseases (Alzheimer, demyelinating core disorders multiple sclerosis and the like), immune related disorders like arthritis, psoriasis, lupus, or other autoimmune diseases as well as chronic infections.

The present invention encompasses the use of the compounds of the formula I and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas, melanomas and breast carcinoma. A further group of preferred forms of cancer include, but is not limited to, cervical cancer, neuroblastoma, testicular cancer, macroglobulinemia and sarcomas.

Also encompassed is the use of the compounds according to Claim 1 according to the invention and/or physiologically acceptable salts and solvates thereof for the preparation of a medicament for the treatment or prevention of a neurological disorder, particularly a neurodegenerative disease, for example a disease caused by axonal degeneration or by protein plaque deposition. Neurodegenerative diseases include, for example, demyelinating core disorders, such as multiple sclerosis, acute transverse myelitis, amyotrophic lateral sclerosis, Creutzfeldt-Jakob disease or Alzheimer disease.

Further encompassed is the use of the compounds according to Claim 1 according to the invention and/or physiologically acceptable salts and solvates thereof for the preparation of a medicament for the treatment of chronic infections. Such a chronic infection could relate to parasites like leishmania to leprosy or to viral infection by HIV and the like.

Further encompassed is the use of the compounds according to Claim 1 according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The present invention encompasses the use of the compounds of the formula I and/or physiologically acceptable salts and solvates thereof for the preparation of a medicament for the treatment or prevention of immune related disorder like ankylosing spondylitis, arthritis, aplastic anemia, Behcet's disease, type 1 diabetes mellitus, graft-versus-host disease, Graves' disease, autoimmune hemolytic anemia, Wegener's granulomatosis, hyper IgE syndrome, idiopathic thrombocytopenia purpura, rheumatoid arthritis, Crohn's disease, multiple sclerosis, Myasthenia gravis, psoriasis, and lupus, among other autoimmune diseases. It might also be used treat organ rejection, bone marrow transplant rejection, non-myeloablative bone marrow transplant rejection, enhance bone marrow engraftment after non-myeloablative conditioning regimens, and combinations thereof Also encompassed is the use of the compounds of the formula I and/or physiologically acceptable salts and solvates thereof for the preparation of a medicament for the treatment or prevention of a immune-modulatory or stress response kinase-induced disease or a immune-modulatory or stress response kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

The expression "immune-modulatory or stress response kinase-induced diseases or conditions" refers to pathological conditions that depend on the activity of one or more immune-modulatory or stress response kinases. immune-modulatory or stress response kinases either directly or indirectly participate in the signal transduction pathways of a variety of cellular activities, including proliferation, adhesion and migration and differentiation. Diseases associated with immune-modulatory or stress response kinase activity include neoplastic malignancies (solid tumor cancers, cancers of the lymphatic or blood system and the like), of neurodegenerative diseases, immune related disorders like arthritis, psoriasis, lupus, multiple sclerosis or other autoimmune diseases as well as chronic infections.

The present invention specifically relates to compounds of the formula I and pharmaceutically acceptable salts, solvates, tautomers and stereoisomers thereof, including mixtures thereof in all ratios, for the use for the treatment of diseases in which the inhibition, regulation and/or modulation inhibition of GCN2 plays a role.

The present invention specifically relates to compounds of the formula I and pharmaceutically acceptable salts, solvates, tautomers and stereoisomers thereof, including mixtures thereof in all ratios, for the use for the inhibition of GCN2.

The present invention specifically relates to compounds of the formula I and pharmaceutically acceptable salts, solvates, tautomers and stereoisomers thereof, including mixtures thereof in all ratios, for the use for the treatment of neoplastic malignancies (solid tumor cancers, cancers of the lymphatic or blood system and the like), of neurodegenerative diseases, immune related disorders like arthritis, psoriasis, lupus, multiple sclerosis or other autoimmune diseases as well as chronic infections.

Especial preference is given to the use for the treatment of a disease where the disease is a neoplastic malignancies.

The neoplastic malignancies is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The neoplastic malignancies is furthermore preferably selected from the group lung adenocarcinoma, small-cell lung carcinomas, pancreatic cancer, glioblastomas, colon carcinoma and breast carcinoma.

Preference is furthermore given to the use for the treatment of a neoplastic malignancies of the blood and immune system, preferably for the treatment of a tumour selected from the group of acute myeloid leukaemia, chronic myeloid leukaemia, acute lymphatic leukaemia and/or chronic lymphatic leukaemia.

The present invention specifically relates to methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a compound of formula I or a pharmaceutically acceptable salt, tautomer, stereoisomer or solvate thereof.

In another aspect provided herein are methods of inhibiting a kinase in a cell expressing said kinase, comprising contacting said cell with an effective amount of a compound of formula I or a pharmaceutically acceptable salt, tautomer, stereoisomer or solvate thereof. In one embodiment the kinase is GCN2 or mutants or isoforms thereof, or combinations of two or more thereof.

Representative immunological conditions that compounds of formula I are useful for treating or preventing include, but are not limited to, Behcet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosus, *pemphigus vulgaris*, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary biliary cirrhosis.

Representative autoimmune conditions that compounds of formula I are useful for treating or preventing include, but are not limited to, autoimmune hemolytic anemia (A1HA), Behcet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, *pemphigus vulgaris*, primary biliary cirrhosis, rheumatoid arthritis, scleroderma, Sjogren's syndrome, ulcerative colitis, or Wegeners granulomatosus.

Representative allergic conditions that compounds of formula I are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that compounds of formula I are useful for treating or preventing include, but are not limited to, rheumatoid arthritis, gout, ankylosing spondylitis, or osteoarthritis.

Representative inflammatory conditions that compounds of formula I are useful for treating or preventing include, but are not limited to, non-ANCA (anti-neutrophil cytoplasmic autoantibody) vasculitis (e.g., wherein GCN2 function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that compounds of formula I are useful for treating or preventing include, but are not limited to, bacterial, parasitic, prion, viral infections or helminth infestation.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that compounds of formula I are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that compounds of formula I are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

The present invention specifically relates to compounds of the formula I and pharmaceutically acceptable salts, solvates, tautomers and stereoisomers thereof, including mixtures thereof in all ratios, for the use for the treatment and/or prevention of inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions, the methods comprising administering to a subject in need thereof an effective amount of a compound of claim 1.

Moreover, the present invention specifically relates to compounds for the use for the treatment and/or prevention of cancer, where the cancer to be treated is a solid tumour or a tumour of the blood and immune system.

Moreover, the present invention specifically relates to compounds, for the use for the treatment and/or prevention of cancer, where the where the tumour originates from the group of acute myeloid leukaemia, chronic myeloid leukaemia, acute lymphatic leukaemia and/or chronic lymphatic leukaemia.

Moreover, the present invention specifically relates to compounds, for the use for the treatment and/or prevention of cancer, where the solid tumour originates from the group of tumours of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondosarcoma and Ewing sarcoma, germ cells, including embryonal tissue tumours, and/or the lung, from the group of monocytic leukaemia, lung adenocarcinoma, small-cell lung carcinomas, pancreatic cancer, glioblastomas, neurofibroma, angiosarcoma, breast carcinoma and/or maligna melanoma.

Moreover, the present invention specifically relates to for the use for the treatment and/or prevention of diseases selected from the group rheumatoid arthritis, systemic lupus, asthma, multiple sclerosis, osteoarthritis, ischemic injury, giant cell arteritis, inflammatory bowel disease, diabetes, cystic fibrosis, psoriasis, Sjögrens syndrom and transplant organ rejection.

Moreover, the present invention specifically relates to compounds for the use for the treatment and/or prevention of diseases selected from the group Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, Parkinson's disease.

Moreover, the present invention specifically relates to compounds for the use for the treatment and/or prevention of diseases selected from the group leishmania, mycobacteria, including *M. leprae, M. tuberculosis* and/or *M. avium, leishmania, plasmodium*, human immunodeficiency virus, Epstein Barr virus, Herpes simplex virus, hepatitis C virus.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for re-placement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |

TABLE 1-continued

| | | |
|---|---|---|
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatin PE (Teikoku Hormone) | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | JSF-154 (Tragen) |
| | Adenocarcinoma vaccine (Biomira) | Cancer vaccine (Intercell) |
| | CTP-37 (AVI BioPharma) | Norelin (Biostar) |
| | JRX-2 (Immuno-Rx) | BLP-25 (Biomira) |

TABLE 1-continued

| | | |
|---|---|---|
| | PEP-005 (Peplin Biotech) | MGV (Progenics) |
| | Synchrovax vaccines (CTL Immuno) | β-Alethin (Dovetail) |
| | | CLL-Thera (Vasogen) |
| | Melanoma vaccine (CTL Immuno) | |
| | p21-RAS vaccine (Gem-Vax) | |
| Hormonal and antihormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (Entre Med) |
| | Tamoxifen | |
| | Toremofin | Arzoxifen (Eli Lilly) |
| | Dexamethasone | |
| Photodynamic agents | Talaporfin (Light Sciences) | Pd-Bacteriopheophorbid (Yeda) |
| | Theralux (Theratechnologies) | Lutetium-Texaphyrin (Pharmacyclics) |
| | Motexafin-Gadolinium (Pharmacyclics) | Hypericin |
| Tyrosine kinase inhibitors | Imatinib (Novartis) | Kahalide F (PharmaMar) |
| | Leflunomide(Sugen/Pharmacia) | CEP-701 (Cephalon) |
| | ZDI839 (AstraZeneca) | CEP-751 (Cephalon) |
| | Erlotinib (Oncogene Science) | MLN518 (Millenium) |
| | Canertjnib (Pfizer) | PKC412 (Novartis) |
| | Squalamine (Genaera) | Phenoxodiol O |
| | SU5416 (Pharmacia) | Trastuzumab (Genentech) |
| | SU6668 (Pharmacia) | C225 (ImClone) |
| | ZD4190 (AstraZeneca) | rhu-Mab (Genentech) |
| | ZD6474 (AstraZeneca) | MDX-H210 (Medarex) |
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | | IMC-1C11 (ImClone) |
| | EKB-509 (Wyeth) | |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | |
| | Tiazofurin (IMPDH inhibitor, Ribapharm) | Indisulam (p53 stimulant, Eisai) |
| | Cilengitide (integrin antagonist, Merck KGaA) | Aplidin (PPT inhibitor, PharmaMar) |
| | SR-31747 (IL-1 antagonist, Sanofi-Synthelabo) | Rituximab (CD20 antibody, Genentech) |
| | CCI-779 (mTOR kinase inhibitor, Wyeth) | Gemtuzumab (CD33 antibody, Wyeth Ayerst) |
| | Exisulind (PDE-V inhibitor, Cell Pathways) | PG2 (haematopoiesis promoter, Pharmagenesis) |
| | CP-461 (PDE-V inhibitor, | Immunol™ (triclosan |

TABLE 1-continued

| | |
|---|---|
| Cell Pathways) | mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | Trans-retinic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1] Prop. INN (Proposed international Nonproprietary Name)
[2] Rec. INN (Recommended International Nonproprietary Names)
[3] USAN (United States Adopted Name)
[4] no INN.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), ml (milliliter), µl (microliter), ACN (acetonitrile), AcOH (acetic acid), CDCl₃ (deuterated chloroform), CD₃OD (deuterated methanol), CH₃CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d₆ (deuterated dimethylsulfoxide), EDC (1-(3-dimethyl-amino-propyl)-3-ethylcarbodiimide), ESI (Electro-spray ionization), EtOAc (ethyl acetate), Et₂O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K₂CO₃ (potassium carbonate), LC (Liquid Chromatography), MeOH (methanol), MgSO₄ (magnesium sulfate), MS (mass spectrometry), MTBE (Methyl tert-butyl ether), NaHCO₃ (sodium bicarbonate), NaBH₄ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays

GCN2: Assay Principle & Conditions

This assay can quantificate the activity of the serin kinase GCN2 (general control non-derepressible-2).

This kinase is involved in the stress metabolism of cells. It is activated upon starvation (amino acid depletion). Its natural substrate is eIF2a (eukaryotic initiation factor 2 alpha subunit), a translation factor, which gets activated (phosphorylated) by GCN2 in case of an amino acid bottleneck in the cells. This in turn leads to a halt of the protein synthesis. Inhibition of GCN2 results in stopping this mechanism: The cell can not stop protein production upon "starvation" stress.

The assay is run in two steps: the enzymatic reaction and the detection step. In the first step GCN2 is incubated with 10 µM ATP and 80 nM of the GFP-labelled substrate eIF2alpha at room temperature.

The enzymatic reaction is stopped by addition of EDTA. The amount of phosphorylated eIF2alpha is determined by TR-FRET (Lanthascreen): A complex is formed consisting of antibody and GFP labelled phospho-eIF2a, which allows a FRET upon exitation at 340 nm.

The GCN2-activity is directly proportional to the ratio of fluorescence units at the emission wavelenghth 520 nm (phosphopeptide-sensitive wavelength=emission of GFP) to the units at 495 nm (reference wavelength=emission of Terbium-chelate).

Final Concentrations in the Enzymatic Reaction

Hepes, pH 7.0 50 mM
MgCl₂ 10 mM
MnCl₂ 5 mM
BSA 0.1%
DMSO 1%
ATP 10 uM
DTT 2 mM
GFP-eIF2a 80 nM (substrate)
GCN2 30 nM (enzyme)

Assay Procedure 4 uL enzyme solution (in assay buffer)
1.5 uL compound (in cmpd dilution buffer/6.3% DMSO)
Incubation 20 min at RT
4 uL substrate/ATP mix (in assay buffer)
Incubation 90 min at RT
10 uL stop/detection mix (in antibody dilution buffer)
Incubation 60 min at RT
Readout Lanthascreen 340/495/520

Cellular Assay for the Determination of Compound Activities

Human U2OS cells (2000 cells/well) are seeded into 384-well plates and incubated for 20 hours.

The next day, the cells are treated with the test compounds and incubated for 2 hours. Then, tryptophanol, at a final concentration of 600 µM, is added to the cells and those are incubated for 30 minutes.

The analysis of cellular GCN2 activities is done by immunocytochemistry. Briefly, cells are fixated on the well surfaces by formaldehyde and permeabilised with Triton X-100. The primary antibody (anti-phospho-eIF2alpha (Ser51, Cell Signalling Technology, #3398) is incubated on the treated cells for 20 hours, followed by a 60 minutes incubation of the secondary antibody (anti-rabbit-IgG-Alexa 488; Molecular Probes #11008). The analysis and quantification of phosphorylated GCN2 is done by scanning the plates in the Acumen Explorer system (TTPLabtech). The obtained data are normalised against the untreated control wells (DMSO only) and expressed as % effect values. The determination of $IC_{50}$ values is done by using the Graph Pad Prism software.

LCMS
Method A
Method: A-0.1% TFA in $H_2O$, B-0.1% TFA in ACN: Flow: 2.0 mL/min.
Column: XBridge C8 (50×4.6 mm, 3.5 μm), +ve mode.
Method B
A: 10 mM $NH_4HCO_3$ in $H_2O$, B: ACN; Flow Rate: 0.8 mL/min.
Column: XBridge C8 (150×4.6) mm, 3.5 μm.
$^1H$ NMR:
Bruker 400 MHz
HPLC:
Method A
Method A: 0.1% TFA in $H_2O$, B: 0.1% TFA in ACN: Flow: 2.0 mL/min.
Column: XBridge C8 (50×4.6 mm, 3.5 μm).
Method B
Method A: 10 mM $NH_4HCO_3$ in $H_2O$, B: ACN; Flow Rate: 0.8 mL/min.
Column: XBridge C8 (150×4.6) mm, 3.5 μm.
HPLC/MS Conditions A
column: Chromolith PerformanceROD RP-18e, 100×3 $mm^2$
gradient: A:B=99:1 to 0:100 in 1.8 min
flow rate: 2.0 ml/min
eluent A: water+0.05% formic acid
eluent B: acetonitrile+0.04% formic acid
wavelength: 220 nm
mass spectroscopy: positive mode
HPLC/MS Conditions B
column: Chromolith PerformanceROD RP-18e, 50×4.6 $mm^2$
gradient: A:B=96:4 to 0:100 in 2.8 min
flow rate: 2.40 ml/min
eluent A: water+0.05% formic acid
Eluent B: acetonitrile+0.04% formic acid
wavelength: 220 nm
mass spectroscopy: positive mode Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

OVERVIEW SYNTHESIS OF IMIDAZOPYRIMIDINES

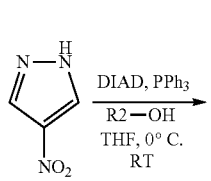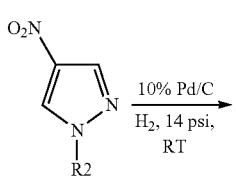

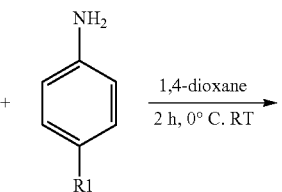

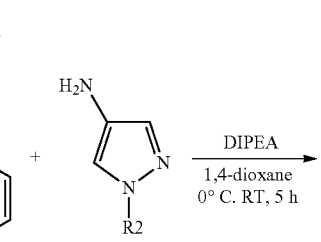

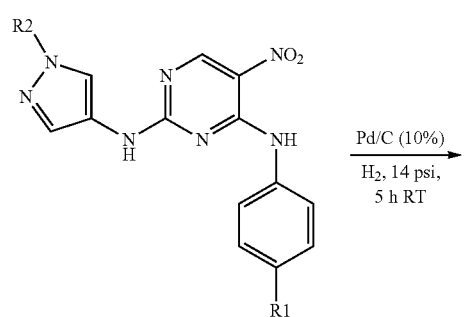

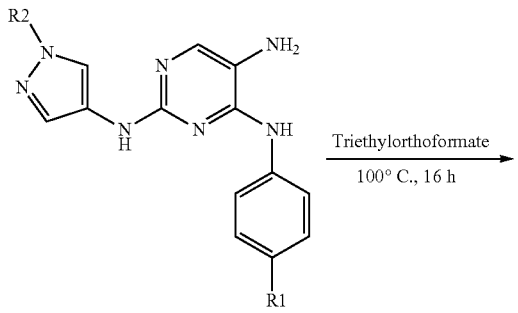

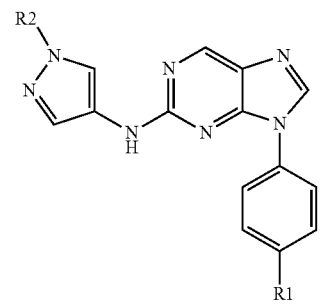

EXAMPLE 1

Synthesis of 9-(4-ethoxyphenyl)-N-(1-(1-methylpiperidin-4-yl)-1H-pyrazol-4-yl)-9H-purin-2-amine ("A1")

Step 1

1-methyl-4-(4-nitro-1H-pyrazol-1-yl)piperidine

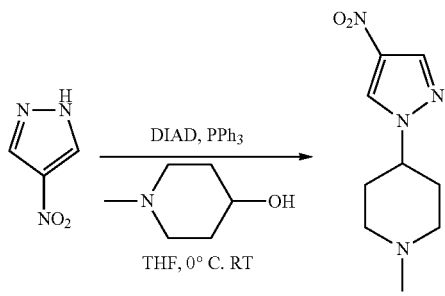

Procedure: DIAD (6.32 mL, 0.026 mol) was added dropwise to a stirred solution of 4-nitro pyazole (3.23 g, 0.0286 mol), 1-methylpiperidin-4-ol (3 g, 0.026 mol) and PPh$_3$ (10.49 g, 0.039 mol) in THF (50 mL) cooled to 0° C. under N$_2$ atmosphere. The resulting solution was stirred at 0° C. for 10 minutes then allowed to warm to room temperature and stirred overnight. The mixture was diluted with hexane (80 mL) and EtOAc (20 mL) and then stirred vigorously. The mixture was filtered and the solid was washed with hexane. The combined filtrates were evaporated and the residue was purified by chromatography to afford 1-methyl-4-(4-nitro-1H-pyrazol-1-yl)piperidine; yield: 38% (2.1 g, Pale Yellow Solid); LCMS: (Method A) 210.1 (M+H).

Step 2

1-(1-methylpiperidin-4-yl)-1H-pyrazol-4-amine

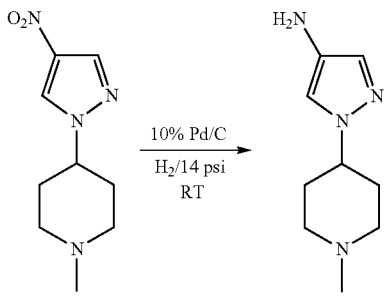

Procedure: 1-methyl-4-(4-nitro-1H-pyrazol-1-yl)piperidine (2.1 g, 0.01 mol), was dissolved in methanol (20 mL) and Pd/C (10%, 300 mg) was added and hydrogenated under balloon H$_2$ (14 psi) for 5 hr. After the completion of the reaction as evidenced by TLC, the reaction mixture was filtered through Celite bed, washed with ethanol (10 mL). The filtrate was concentrated to get desired compound 1-(1-methylpiperidin-4-yl)-1H-pyrazol-4-amine; yield: 81% (1.5 g, yellow liquid); LCMS: (Method A) 181.1 (M+H).

Step 3

2-chloro-N-(4-ethoxyphenyl)-5-nitropyrimidin-4-amine

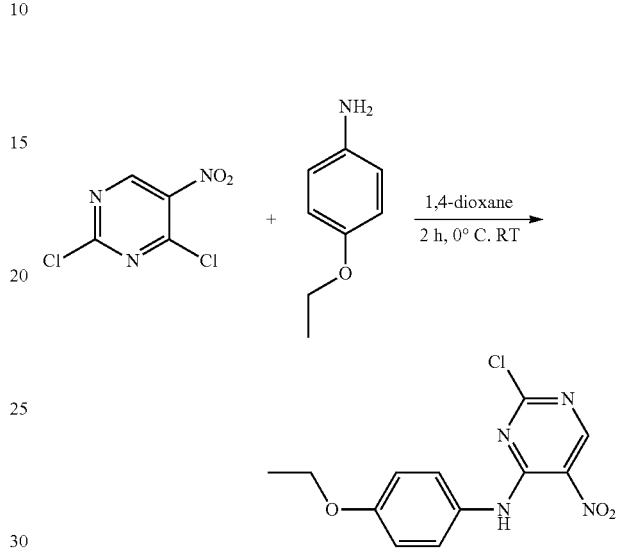

Procedure: To a solution of 2,4-dichloro-5-nitropyrimidine (1.5 g, 0.0077 mol) in 1,4-dioxane (10 mL) at 0° C. was added a solution of (4-ethoxyphenyl) amine (0.37 g, 0.0077 mol)) in 1,4-dioxane (5 mL). The reaction was stirred for 2 h. After the completion of the reaction as evidenced by TLC, the reaction mixture was evaporated under reduced pressure and the resulting residue was purified by column chromatography to give the 2-chloro-N-(4-ethoxyphenyl)-5-nitropyrimidin-4-amine; yield: 66% (1.5 g, yellow solid); LCMS: (Method A) 295.0 (M+H).

Step 4

N$^4$-(4-ethoxyphenyl)-N$^2$-(1-(1-methylpiperidin-4-yl)-1H-pyrazol-4-yl)-5-nitropyrimidine-2,4-diamine

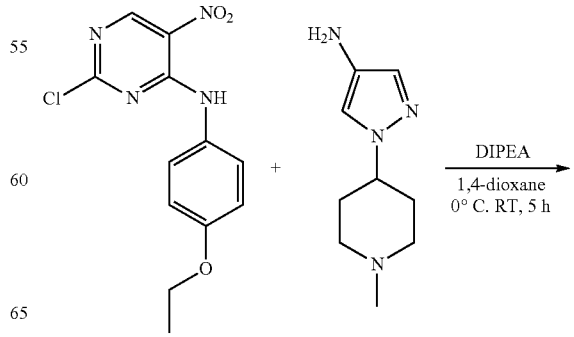

-continued

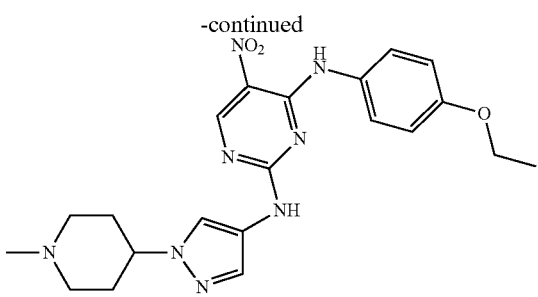

Procedure: To a stirred solution of 2-chloro-N-(4-ethoxyphenyl)-5-nitropyrimidin-4-amine (1.5 g, 0.0053 mol) in 1,4-dioxane (10 mL) at 0° C. was added a solution of 1-(1-methylpiperidin-4-yl)-1H-pyrazol-4-amine (0.96 g, 0.0053 mol), DIPEA (1 mL, 0.016 mol) in 1,4-dioxane (2 mL) and allowed to stir for 5 h. After the completion of the reaction as evidenced by TLC, the solvent was removed under reduced pressure and the resulting residue was purified by column chromatography to afford $N^4$-(4-ethoxyphenyl)-$N^2$-(1-(1-methylpiperidin-4-yl)-1H-pyrazol-4-yl)-5-nitropyrimidine-2,4-diamine; yield: 65% (1.5 g, yellow solid); LCMS: (Method A) 439.0 (M+H).

Step 5

N4-(4-ethoxyphenyl)-N2-(1-(1-methylpiperidin-4-yl)-1H-pyrazol-4-yl) pyrimidine-2,4,5-triamine

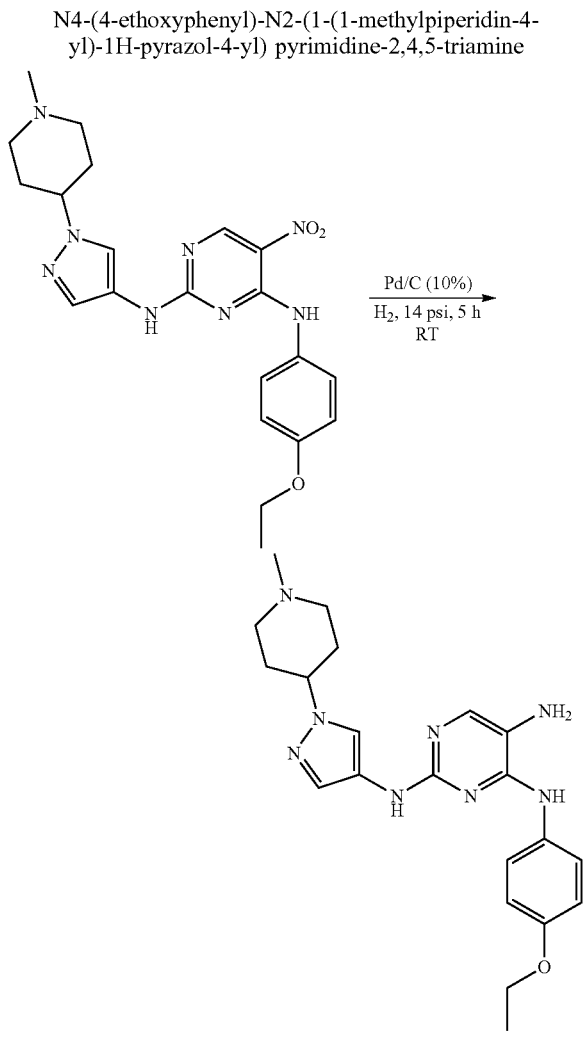

Procedure: To a mixture of $N^4$-(4-ethoxyphenyl)-$N^2$-(1-(1-methylpiperidin-4-yl)-1H-pyrazol-4-yl)-5-nitropyrimidine-2,4-diamine (1.5 g, 0.0034 mol), in methanol (20 mL) was added Pd/C (10%, 300 mg) and hydrogenated under $H_2$ atmosphere for 5 h. After the completion of the reaction as evidenced by TLC, the reaction mixture was filtered through celite bed, washed with ethanol (10 mL). The filtrate was concentrated to get desired compound $N^4$-(4-ethoxy-phenyl)-$N^2$-(1-(1-methylpiperidin-4-yl)-1H-pyrazol-4-yl)pyrimidine-2,4,5-triamine; yield: 65% (0.9 g, pale yellow gummy solid); LCMS: (Method A) 409.0 (M+H).

Step 6

9-(4-ethoxyphenyl)-N-(1-(1-methylpiperidin-4-yl)-1H-pyrazol-4-yl)-9H-purin-2-amine ("A1")

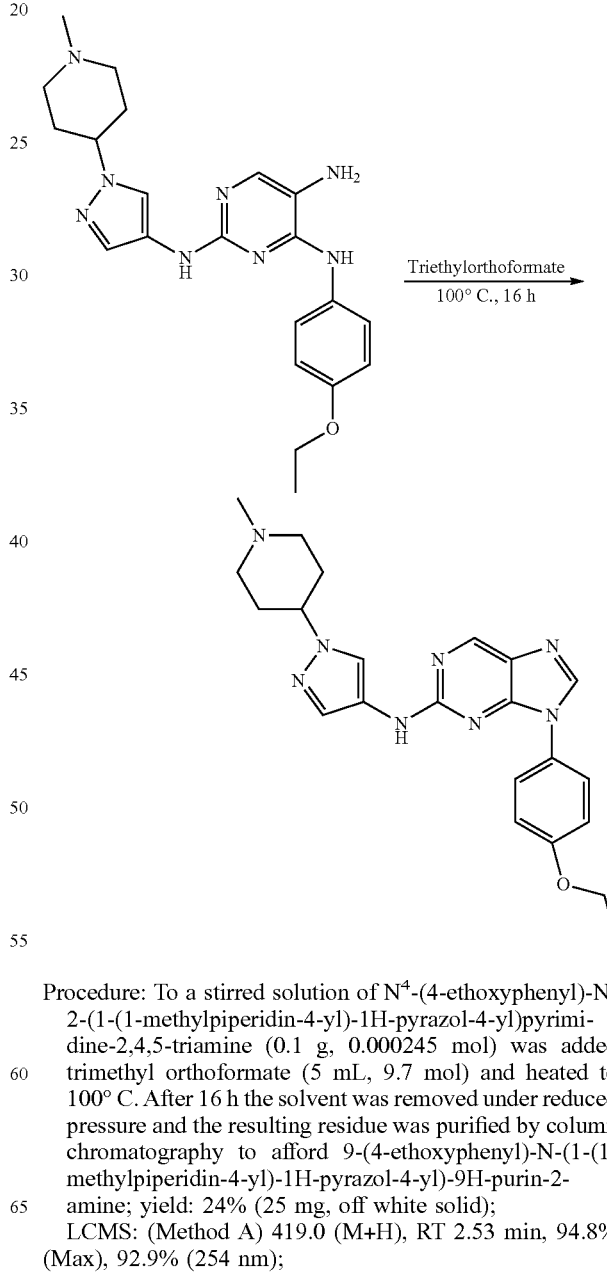

Procedure: To a stirred solution of $N^4$-(4-ethoxyphenyl)-N-2-(1-(1-methylpiperidin-4-yl)-1H-pyrazol-4-yl)pyrimidine-2,4,5-triamine (0.1 g, 0.000245 mol) was added trimethyl orthoformate (5 mL, 9.7 mol) and heated to 100° C. After 16 h the solvent was removed under reduced pressure and the resulting residue was purified by column chromatography to afford 9-(4-ethoxyphenyl)-N-(1-(1-methylpiperidin-4-yl)-1H-pyrazol-4-yl)-9H-purin-2-amine; yield: 24% (25 mg, off white solid);

LCMS: (Method A) 419.0 (M+H), RT 2.53 min, 94.8% (Max), 92.9% (254 nm);

HPLC: (Method A) RT, 2.69 min 94.8%, (Max), 92.6% (254 nm);

$^1$H NMR: (400 MHz, DMSO-d$_6$): δ [ppm] 9.62 (s, 1H), 8.84 (s, 1H), 8.49 (s, 1H), 8.02 (s, 1H), 7.78 (d, J=8.5 Hz, 2H), 7.44 (s, 1H), 7.17 (d, J=8.7 Hz, 2H), 4.15-4.10 (m, 2H), 4.02-3.99 (m, 1H), 2.87-2.84 (m, 2H), 2.22 (s, 3H), 1.96-2.05 (m, 4H), 1.87-1.82 (m, 2H), 1.38 (t, J=6.9 Hz, 3H).

EXAMPLE 2

Synthesis of 9-(4-(2-methoxyethoxyl)phenyl)-N-(1-(1-methylpiperidin-4-yl)-1H-pyrazol-4-yl)-9H-purin-2-amine ("A2")

Step 1

2-chloro-N-[4-(2-methoxyethoxyl)phenyl]-5-nitro-pyrimidin-4-amine

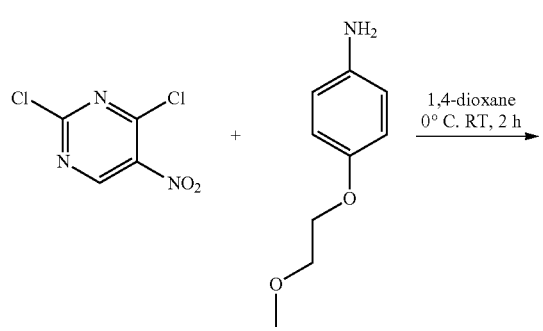

Procedure: To a stirred solution of 2,4-dichloro-5-nitropyrimidine (0.25 g, 0.013 mol) in 1,4-dioxane (10 mL) at 0° C. was added a solution of [4-(2-methoxy ethyl)phenyl] amine (0.217 g, 0.0013 mol) in 1,4-dioxane (5 mL). The reaction mixture was stirred for 2 h. After the completion of the reaction as evidenced by TLC, the solvent was removed under reduced pressure and the resulted residue was purified by column chromatography afford 2-chloro-N-[4-(2-methoxyethoxyl)phenyl]-5-nitropyrimidin-4-amine; yield: 40% (0.17 g, yellow solid); LCMS: (Method A) 325.0 (M+H).

Step 2

N$^4$-(4-(2-methoxyethoxyl)phenyl)-N$^2$-(1-(1-methyl-piperidin-4-yl)-1H-pyrazol-4-yl)-5-nitropyrimidine-2,4-diamine

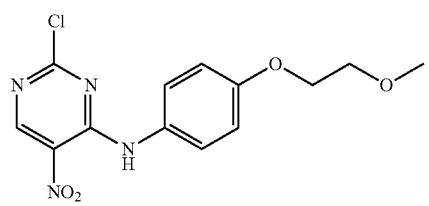

Procedure: To a stirred solution of 2-chloro-N-[4-(2-methoxyethoxyl)phenyl]-5-nitropyrimidin-4-amine (0.17 g, 0.00052 mol) in 1,4-dioxane (10 mL) at 0° C. was added a solution of 1-(1-methylpiperidin-4-yl)-1H-pyrazol-4-amine (obtained from example 1 step 2; 0.096 g, 0.00052 mol), DIPEA (0.1 mL, 0.00057 mol) in 1,4-dioxane (2.0 mL) and stirred for 12 h. After the completion of the reaction, the solvent was removed under reduced pressure and the resulted residue was purified by column chromatography to afford N$^4$-(4-(2-methoxy-ethoxyl)phenyl)-N$^2$-(1-(1-methylpiperidin-4-yl)-1H-pyrazol-4-yl)-5-nitro pyrimidine-2,4-diamine); yield: 82% (0.20 g, pale yellow solid); LCMS: (Method A) 469.1 (M+H).

Step 3
N⁴-(4-(2-methoxyethoxy)phenyl)-N²-(1-(1-methyl-piperidin-4-yl)-1H-pyrazol-4-yl)pyrimidine-2,4,5-triamine

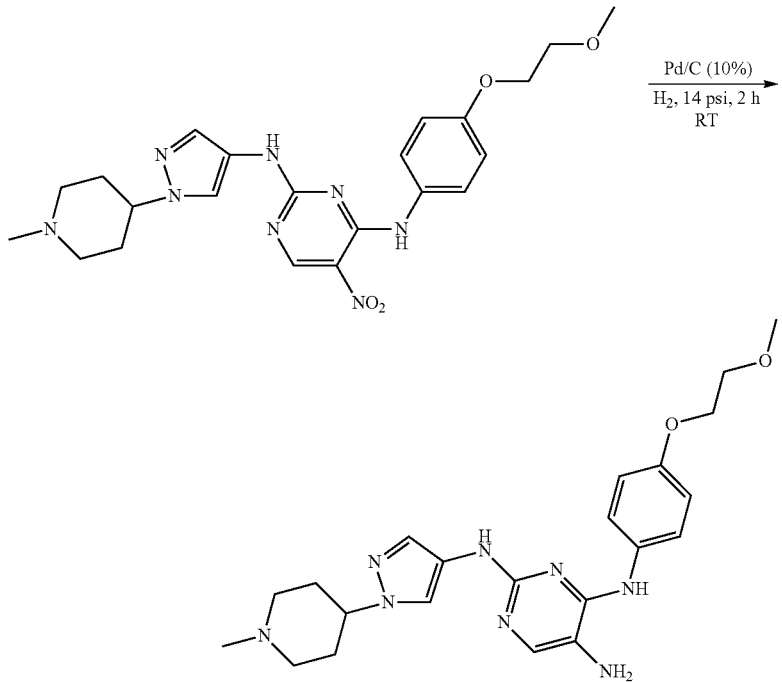

A mixture of N⁴-(4-(2-methoxyethoxy)phenyl)-N²-(1-(1-methylpiperidin-4-yl)-1H-pyrazol-4-yl)-5-nitropyrimidine-2,4-diamine (0.2 g, 0.00042 mol), Pd/C (10%, 25 mg) in methanol (20 mL) was hydrogenated for 2 h under H₂ atmosphere. After the completion of the reaction, the reaction mixture was filtered through Celite bed, washed with ethanol (10 mL). The filtrate was concentrated to get desired compound N⁴-(4-(2-methoxyethoxy)phenyl)-N²-(1-(1-methylpiperidin-4-yl)-1pyrazol-4-yl)pyrimidine-2,4,5-triamine; yield: 54% (0.10 g, yellow liquid); LCMS: (Method A) 439.1 (M+H).

Step 4
9-(4-(2-methoxyethoxy)phenyl)-N-(1-(1-methylpiperidin-4-yl)-1H-pyrazol-4-yl)-9H-purin-2-amine ("A2")

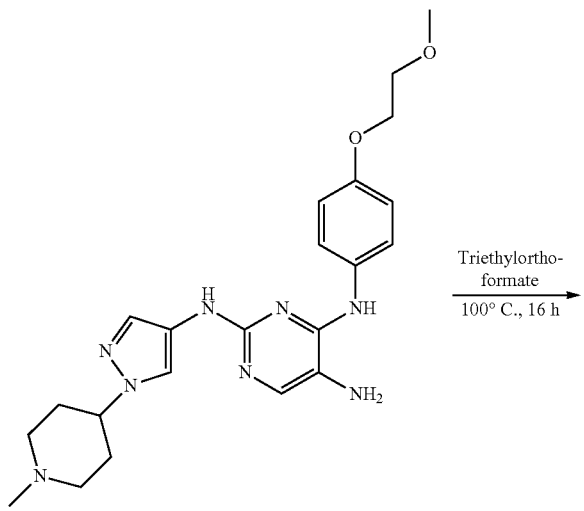

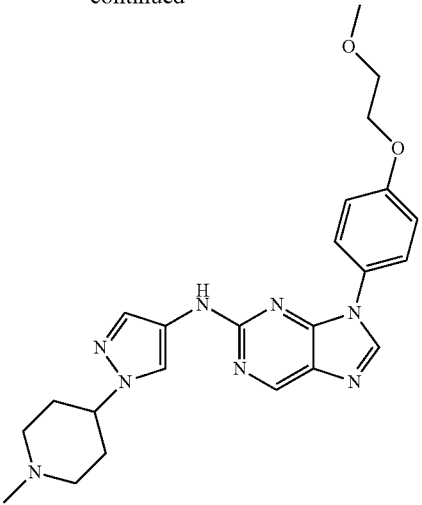

Procedure: To a stirred solution of N⁴-(4-(2-methoxy-ethoxyl)phenyl)-N²-(1-(1-methyl piperidin-4-yl)-1H-pyrazol-4-yl)pyrimidine-2,4,5-triamine (0.1 g, 0.00022 mol) was added trimethyl orthoformate (5 ml, 9.7 mol) and heated to 100° C. After 18 h, the solvent was removed under reduced pressure and the resulted residue was purified by column chromatography to afford 9-(4-(2-methoxy-ethoxy)phenyl)-N-(1-(1-methyl piperidin-4-yl)-1H-pyrazol-4-yl)-9H-purin-2-amine; yield: 10% (10 mg, pale brown solid); LCMS: (Method A) 449.3 (M+H), RT, 2.24 min, 91.1% (Max), 94.4% (254 nm);

HPLC: (Method A) RT 2.46 min 96.2% (Max), 96.4% (254 nm);

$^1$H NMR: (400 MHz, DMSO-d$_6$): δ [ppm] 8.77 (s, 1H), 8.37 (s, 1H), 8.09 (s, 1H), 7.75 (dd, J=2.2, 6.7 Hz, 2H), 7.61 (s, 1H), 7.23 (d, J=8.9 Hz, 2H), 4.25-4.23 (m, 2H), 4.19-4.16 (m, 1H), 3.83-3.81 (m, 2H), 3.47 (s, 3H), 3.14-3.12 (m, 2H), 2.47-2.43 (m, 5H), 2.19-2.16 (m, 2H), 2.04-2.02 (m, 2H).

EXAMPLE 3

Synthesis of 4-(2-((1-(tetrahydro-2H-pyran-4-yl)-1H-pyrazol-4-yl)amino)-9H-purin-9-yl)benzamide ("A3")

Step 1

4-nitro-1-(tetrahydro-2H-pyran-4-yl)-1H-Pyrazole

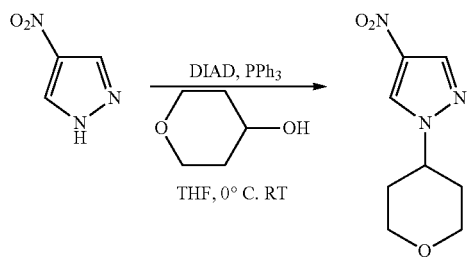

Procedure: To a stirred solution of di-tert-butyl azodicarboxylate (2.6 g, 11.5 mmol) in THF (5 mL) was added tetrahydro-pyran-4-ol (903 mg, 8.85 mmol), 4-nitro-1H-pyrazole (1.0 g, 8.85 mmol) and PPh$_3$ (2.8 g, 10.62 mmol) in THF (35 mL) at RT for 16 h. After completion of the reaction the mixture was concentrated under reduced pressure to afford the crude product which was purified by column chromatography to afford the product; yield: 91% (1.59 g, white solid);
$^1$H NMR: (400 MHz, DMSO-d$_6$): δ [ppm] 2.04-1.90 (m, 4 H), 3.44-3.41 (m, 2 H), 3.99-3.92 (m, 2 H), 4.55-4.46 (m, 1 H), 8.29 (s, 1 H), 8.96 (s, 1 H).

Step 2

1-(tetrahydro-2H-pyran-4-yl)-1H-Pyrazol-4-amine

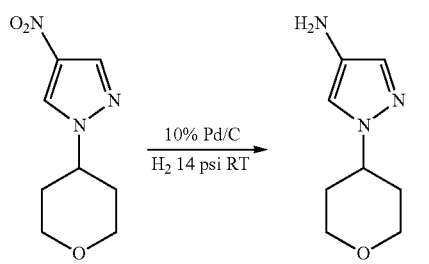 [SMILES: O=[N+]([O-])c1cnn(C2CCOCC2)c1 ; Nc1cnn(C2CCOCC2)c1]

Procedure: To a solution of 4-nitro-1-(tetrahydro-pyran-4-yl)-1H-pyrazole (1.59 g, 8.07 mmol) was added 10% Pd/C (300 mg) in ethanol (30 mL) and stirred for 16 h under H$_2$ atmosphere. After the completion of the reaction, the reaction mixture was filtered through a Celite bed and the filtrate was concentrated to afford the product; yield: 98% (1.33 g, purple colored solid);
$^1$H NMR: (400 MHz, DMSO-d$_6$): δ [ppm] 1.76-1.94 (m, 4 H), 3.29-3.48 (m, 2 H), 3.80 (s, 2 H), 4.00-3.48 (m, 2 H), 4.16-4.12 (m, 1 H), 6.90 (s, 1 H), 7.06 (s, 1 H).

Step 3

4-((2-chloro-5-nitropyrimidin-4-yl)amino)benzamide

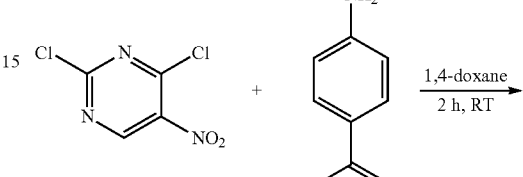

Procedure: To a stirred solution of 2,4-dichloro-5-nitropyrimidine (0.5 g, 0.0025 mol) in 1,4-dioxane (10 mL) at 0° C. was added a solution of 4-aminobenzamide (0.35 g, 0.0025 mol) in 1,4-dioxane (5 mL). The reaction was stirred for 2 h. After the completion of the reaction, the solvent was removed under reduced pressure and the resulted residue was purified by column chromatography to afford 4-((2-chloro-5-nitropyrimidin-4-yl)amino)benzamide; yield: 41% (0.3 g, yellow solid); LCMS: (Method A) 294.0 (M+H).

Step 4

4-((5-nitro-2-((1-(tetrahydro-2H-pyran-4-yl)-1H-Pyrazol-4-yl)amino)pyrimidin-4-yl)amino)benzamide

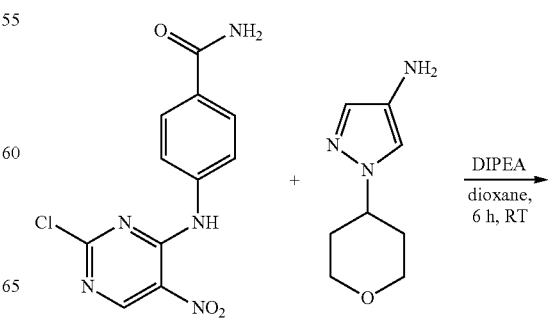

-continued

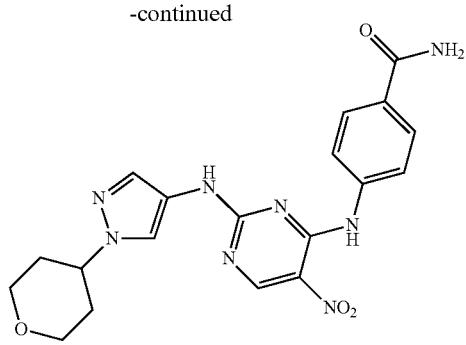

Procedure: To a stirred solution of 4-(2-chloro-5-nitropyrimidin-4-yl)amino)-benzamide (0.3 g, 0.0010 mol) in 1,4-dioxane (10 mL) at 0° C. was added a solution of 1-(tetrahydro-2H-pyran-4-yl)-1H-pyrazol-4-amine (0.17 g, 0.0010 mol) and DIPEA (0.5 mL, 0.003 mol) in 1,4-dioxane (2 mL). The reaction was stirred for 8 h. After the completion of the reaction, the solvent was removed under reduced pressure and the resulting residue was purified by column chromatography to afford 4-(5-nitro-2-((1-(tetrahydro-2H-pyran-4-yl)-1H-pyrazol-4-yl)amino)pyrimidin-4-yl)amino)benzamide; yield: 47% (0.2 g, yellow solid); LCMS: (Method A) 425.1 (M+H).

Step 5

4-((5-amino-2-((1-(tetrahydro-2H-pyran-4-yl)-1H-Pyrazol-4-yl)amino)pyrimidin-4-yl)amino)benzamide

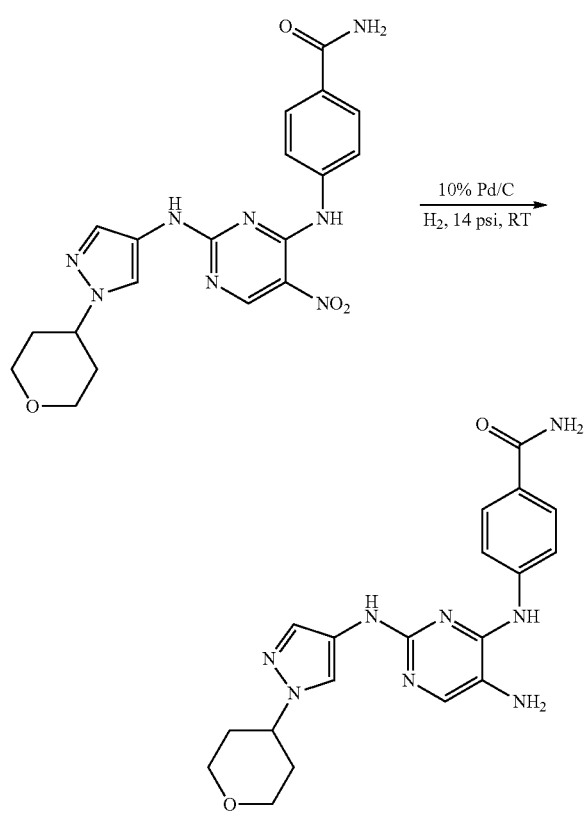

Procedure: A mixture of 4-((5-nitro-2-((1-(tetrahydro-2H-pyran-4-yl)-1H-pyrazol-4-yl)amino)pyrimidin-4-yl)amino)benzamide (0.2 g, 0.00047 mol), Pd/C (10%, 25 mg) in $CH_3OH$ (20 mL) was hydrogenated under $H_2$ atmosphere for 5 hr. After the completion of the reaction as evidenced by TLC, the reaction mixture was filtered through Celite, washed with ethanol (10 mL). The filtrate was concentrated to get desired compound 4-((5-amino-2-((1-(tetrahydro-2H-pyran-4-yl)-1H-pyrazol-4-yl)amino)pyrimidin-4-yl)amino)benzamide; yield: 54% (0.1 g, yellow liquid); LCMS: (Method A) 395.0 (M+H).

Step 6

4-(2-((1-(tetrahydro-2H-pyran-4-yl)-1H-pyrazol-4-yl)amino)-9H-purin-9-yl)benzamide

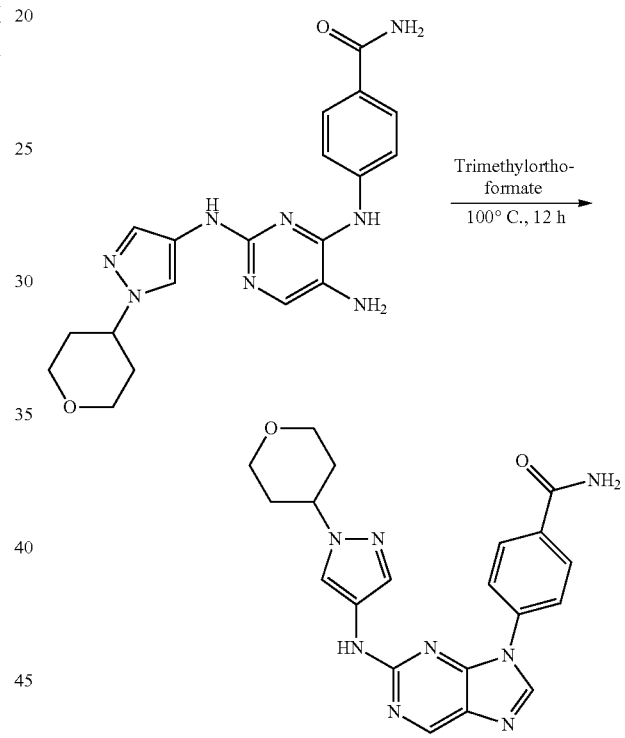

Procedure: A solution of 4-((5-amino-2-((1-(tetrahydro-2H-pyran-4-yl)-1H-pyrazolyl)amino)pyrimidin-4-yl)amino)benzamide (0.1 g, 0.00025 mol) and trimethyl orthoformate (5 ml, 9.7 mol) were stirred at 100° C. for 12 h. After the completion of the reaction, the solvent was removed under reduced pressure and the resulting residue was purified by column chromatography to afford 4-(2-((1-(tetrahydro-2H-pyran-4-yl)-1H-pyrazol-4-yl)amino)-9H-purin-9-yl)-benzamide; yield: 24% (25 mg, pale brown solid);

LCMS: (Method A) 405.2 (M+H), RT, 2.26 min, 97.3% (Max), 97.4% (254 nm); HPLC: (Method A) RT 2.22 min 98.0% (Max), 98.0% (254 nm);

$^1$H NMR: (400 MHz, DMSO-$d_6$): δ [ppm] 9.67 (s, 1H), 8.88 (s, 1H), 8.67 (s, 1H), 8.14-8.12 (m, 3H), 8.06-8.01 (m, 3H), 7.54-7.52 (m, 2H), 4.32-4.28 (m, 1H), 3.98-3.95 (m, 2H), 3.47 (t, J=1.96 Hz, 2H), 2.02-1.98 (m, 2H), 1.85-1.83 (m, 2H).

EXAMPLE 4

Synthesis of N,9-bis-(1-ethyl-1H-pyrazol-4-yl)-9H-purin-2-amine ("A4")

Step 1

1-ethyl-4-nitro-1H-pyrazole

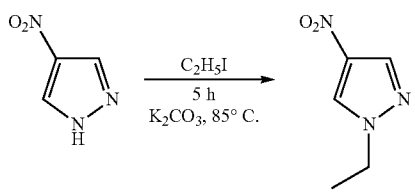

Procedure: To a stirred solution of 4-nitro-1H-pyrazole (2 g, 0.0176 mol) in CH$_3$CN (50 mL) were added K$_2$CO$_3$ (4.88 g 0.035 mol) and iodoethane (2.7 g, 0.0176 mol). The resulting mixture was stirred at 85° C. for 5 h. After the completion of the reaction, the reaction mixture was filtered through a Celite bed, washed with methanol (10 mL). The filtrate was concentrated to afford 1-ethyl-4-nitro-1H-pyrazole; yield: 24% (1.50 g, white solid);

$^1$H NMR: (400 MHz, DMSO-d$_6$): δ [ppm] 1.55 (t, J=7.3 Hz, 3H), 4.22 (m, 2H), 8.07 (s, 1H), 8.14 (s, 1H).

Step 2

1-ethyl-1H-pyrazol-4-amine

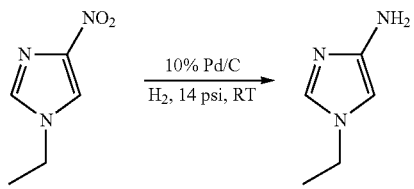

Procedure: To a solution of 1-ethyl-4-nitro-1H-pyrazole (2 g, 0.014 mol) was added 10% Pd/C (300 mg) in ethanol (30 mL) and stirred for 16 h under H$_2$ atmosphere. After the completion of the reaction, the reaction mixture was filtered through a Celite bed and the filtrate was concentrated to afford 1-ethyl-1H-pyrazol-4-amine; yield: 81% (1.50 g, pale yellow liquid).

$^1$H NMR: (400 MHz, DMSO-d$_6$): δ [ppm] 7.15 (s, 1H), 7.02 (s, 1H), 4.05-4.02 (m, 2H), 2.88 (br s, 2H), 1.43 (t, 3H, J=7.2 Hz).

Step 3

N$^2$,N$^4$-bis(1-ethyl-1H-pyrazol-4-yl)-5-nitropyrimidine-2,4-diamine

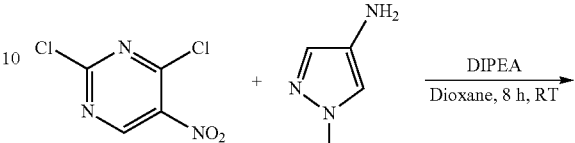

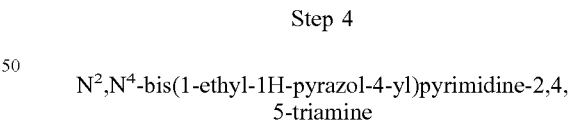

Procedure: To a stirred solution of 2,4-dichloro-5-nitropyrimidine (1 g, 0.0051 mol) in 1,4-dioxane (10 mL) at 0° C. was added a solution of 1-ethyl-1H-pyrazol-4-amine (0.288 g, 0.010 mol) and DIPEA (2.7 mL, 0.015 mol) in 1,4-dioxane (2 mL). The reaction was stirred for 8 h. After the completion of the reaction, the solvent was removed under reduced pressure and the resulting residue was purified by column chromatography to afford N$^2$,N$^4$-bis(1-ethyl-1H-pyrazol-4-yl)-5-nitropyrimidine-2,4-diamine; yield: 45% (0.8 g, yellow solid); LCMS: (Method A) 344.0 (M+H).

Step 4

N$^2$,N$^4$-bis(1-ethyl-1H-pyrazol-4-yl)pyrimidine-2,4,5-triamine

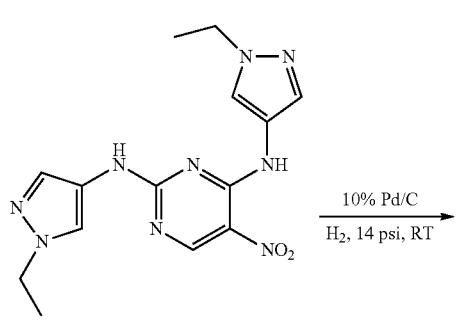

-continued

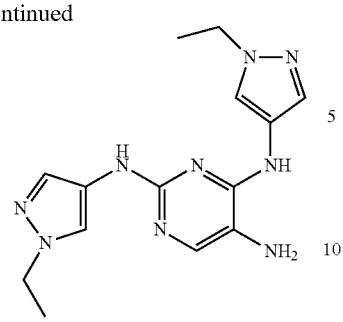

Procedure: A mixture of $N^2,N^4$-bis(1-ethyl-1H-pyrazol-4-yl)-5-nitropyrimidine-2,4-diamine (0.8 g, 0.0023 mol), Pd/C (10%, 150 mg) in $CH_3OH$ (20 mL) was hydrogenated under $H_2$ atmosphere for 5 hr. After the completion of the reaction as evidenced by TLC, the reaction mixture was filtered through Celite, washed with ethanol (10 mL). The filtrate was concentrated to afford $N^2,N^4$-bis(1-ethyl-1H-pyrazol-4-yl)pyrimidine-2,4,5-triamine; yield: 83% (0.6 g, pale yellow liquid); LCMS: (Method A) 314.0 (M+H).

Step 5

N,9-bis(1-ethyl-1H-pyrazol-4-yl)-9H-purin-2-amine

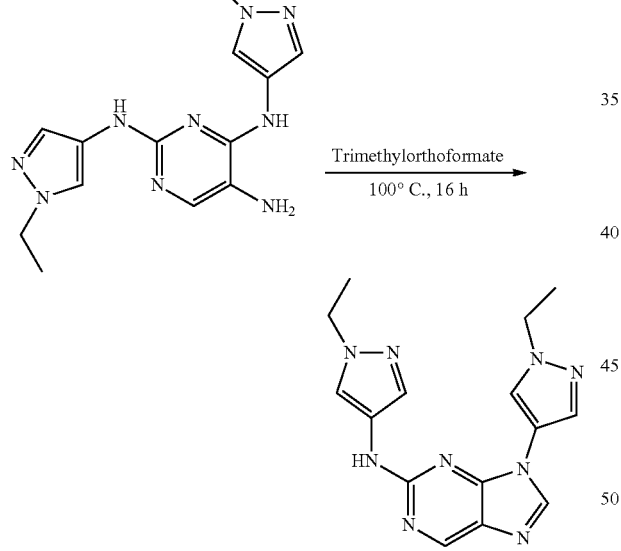

Procedure: A solution of N2,N4-bis(1-ethyl-1H-pyrazol-4-yl)pyrimidine-2,4,5-triamine (0.1 g, 0.00032 mol) and trimethyl orthoformate (5 ml, 9.7 mol) were stirred at 100° C. for 16 h. After the completion of the reaction, the solvent was removed under reduced pressure and the resulting residue was purified by column chromatography to afford N, 9-bis(1-ethyl-1H-pyrazol-4-yl)-9H-purin-2-amine; yield: 38% (40 mg, off-white solid); LCMS: (Method A) 324.0 (M+H), RT, 2.31 min, 99.9% (Max), 99.9% (254 nm);

HPLC: (Method A) RT 2.44 min 99.5% (Max), 99.2% (254 nm);

$^1$H NMR: (400 MHz, DMSO-$d_6$): δ [ppm] 9.55 (s, 1H), 8.82 (s, 1H), 8.43 (s, 1H), 8.02 (s, 1H), 7.94 (s, 1H), 7.52 (s, 1H), 4.24 (q, J=7.2 Hz, 2H), 4.09 (q, J=7.2 Hz, 2H), 1.45 (t, J=7.2 Hz, 3H), 1.36 (t, J=7.2 Hz, 3H).

EXAMPLE 5

Synthesis of 9-(1-ethyl-1H-pyrazol-4-yl)-N-(1-(tetrahydro-2H-pyran-4-yl)-1H-pyrazol-4-yl)-9H-purin-2-amine ("A5")

Step 1

2-chloro-N-(1-ethyl-1H-pyrazol-4-yl)-5-nitropyrimidin-4-amine

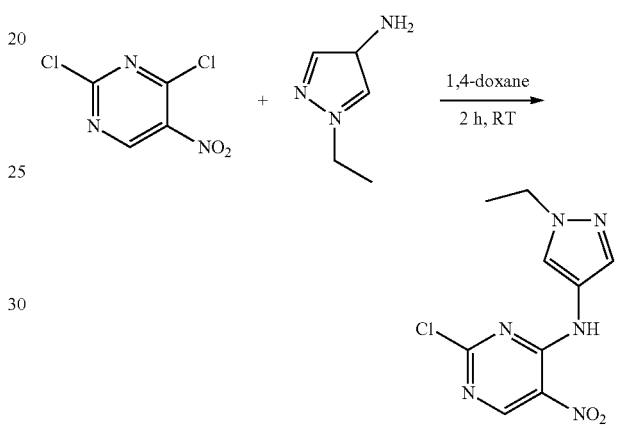

Procedure: To a stirred solution of 2,4-dichloro-5-nitropyrimidine (0.25 g, 0.0013 mol) in 1,4-dioxane (10 mL) at 0° C. was added a solution of 1-ethyl-1H-pyrazol-4-amine (0.14 g, 0.0013 mol) in 1,4-dioxane (5 mL). The reaction was stirred for 2 h. After the completion of the reaction, the solvent was removed under reduced pressure and the resulted residue was purified by column chromatography to afford 2-chloro-N-(1-ethyl-1H-pyrazol-4-yl)-5-nitropyrimidin-4-amine; yield: 57% (0.2 g, yellow solid): LCMS: (Method A) 269.0 (M+H).

Step 2

$N^4$-(1-ethyl-1H-pyrazol-4-yl)-5-nitro-$N^2$-(1-(tetrahydro-2H-pyran-4-yl)-1H-pyrazol-4-yl)pyrimidine-2,4-diamine

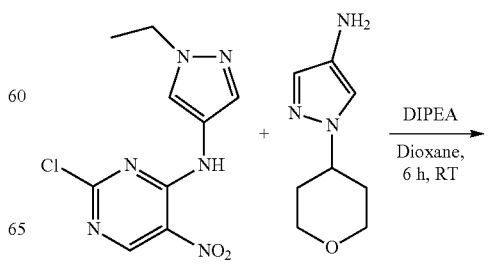

-continued

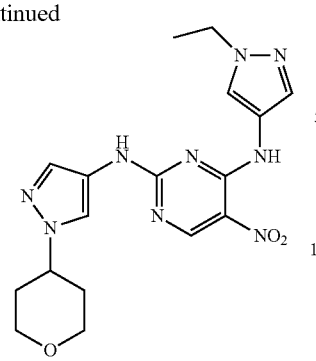

Procedure: To a stirred solution of 2-chloro-N-(1-ethyl-1H-pyrazol-4-yl)-5-nitro pyrimidin-4-amine (0.3 g, 0.0012 mol) in 1,4-dioxane (10 mL) at 0° C. was added a solution of 1-(tetrahydro-2H-pyran-4-yl)-1H-pyrazol-4-amine (0.22 g, 0.0012 mol) and DIPEA (0.2 mL, 0.002 mol) in 1,4-dioxane (2 mL). The reaction was stirred for 6 h. After the completion of the reaction, the solvent was removed under reduced pressure and the resulting residue was purified by column chromatography to afford $N^4$-(1-ethyl-1H-pyrazol-4-yl)-5-nitro-$N^2$-(1-(tetrahydro-2H-pyran-4-yl)-1H-pyrazol-4-yl)pyrimidine-2,4-diamine; yield: 42% (0.2 g, yellow solid); LCMS: (Method A) 400.0 (M+H).

Step 3

$N^4$-(1-ethyl-1H-pyrazol-4-yl)-$N^2$-(1-(tetrahydro-2H-pyran-4-yl)-1H-pyrazol-4-yl) pyrimidine-2,4,5-triamine

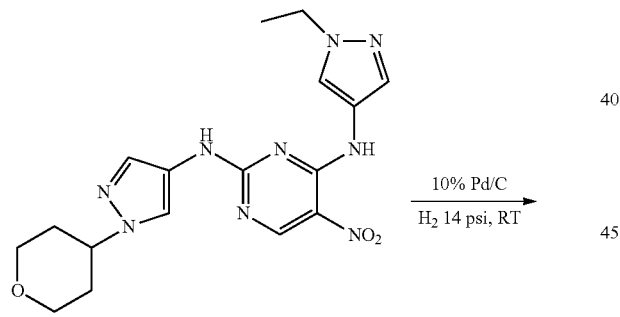

Procedure: A mixture of $N^4$-(1-ethyl-1H-pyrazol-4-yl)-5-nitro-$N^2$-(1-(tetrahydro-2H-pyran-4-yl)-1H-pyrazol-4-yl) pyrimidine-2,4-diamine (0.2 g, 0.0005 mol), Pd/C (10%, 50 mg) in CH$_3$OH (20 mL) was hydrogenated under H$_2$ atmosphere for 5 hr. After the completion of the reaction as evidenced by TLC, the reaction mixture was filtered through Celite, washed with ethanol (10 mL). The filtrate was concentrated to get desired compound $N^4$-(1-ethyl-1H-pyrazol-4-yl)-$N^2$-(1-(tetrahydro-2H-pyran-4-yl)-1H-pyrazol-4-yl)pyrimidine-2,4,5-triamine; yield: 54% (0.1 g, white gummy liquid); LCMS: (Method A) 370.0 (M+H).

Step 4

9-(1-ethyl-1H-pyrazol-4-yl)-N-(1-(tetrahydro-2H-pyran-4-yl)-1H-Pyrazol-4-yl)-9H-purin-2-amine

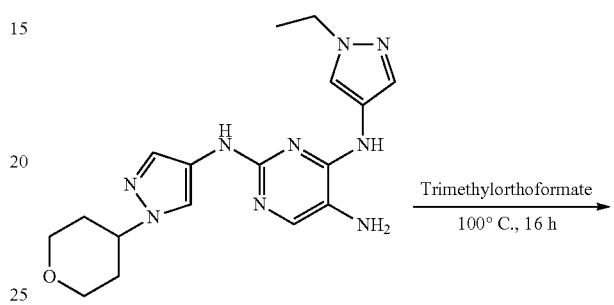

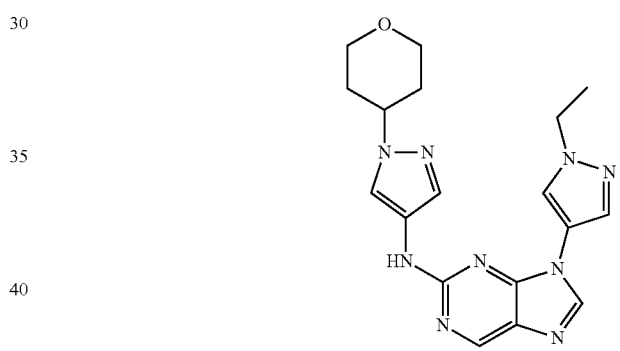

Procedure: A solution of $N^4$-(1-ethyl-1H-pyrazol-4-yl)-$N^2$-(1-(tetrahydro-2H-pyran-4-yl)-1H-pyrazol-4-yl)pyrimidine-2,4,5-triamine (0.1 g, 0.00027 mol) and trimethyl orthoformate (5 ml, 9.7 mol) were stirred at 100° C. for 16 h. After the completion of the reaction, the solvent was removed under reduced pressure and the resulting residue was purified by column chromatography to afford 9-(1-ethyl-1H-pyrazol-4-yl)-N-(1-(tetra hydro-2H-pyran-4-yl)-1H-pyrazol-4-yl)-9H-purin-2-amine; yield: 49% (50 mg, off-white solid); LCMS: (Method A) 380.0 (M+H), RT 2.31 min, 95.5% (Max), 95.3% (254 nm);

HPLC: (Method A) RT, 2.50 min 95.6% (Max), 94.6% (254 nm);

$^1$H NMR: (400 MHz, DMSO-d$_6$): δ [ppm] 9.58 (s, 1H), 8.82 (s, 1H), 8.43 (d, J=7.2 Hz, 2H), 8.01 (d, J=2.4 Hz, 2H), 7.54 (s, 1H), 4.34-4.30 (m, 1H), 4.24 (d, J=7.2 Hz, 2H), 3.95-3.94 (m, 2H), 3.46-3.45 (m, 2H), 1.97-1.90 (m, 4H), 1.45 (t, J=7.2 Hz, 3H).

EXAMPLE 6

Synthesis of 9-(4-ethoxyphenyl)-8-methyl-N-(1-(1-methylpiperidin-4-yl)-1H-pyrazol-4-yl)-9H-purin-2-amine ("A6")

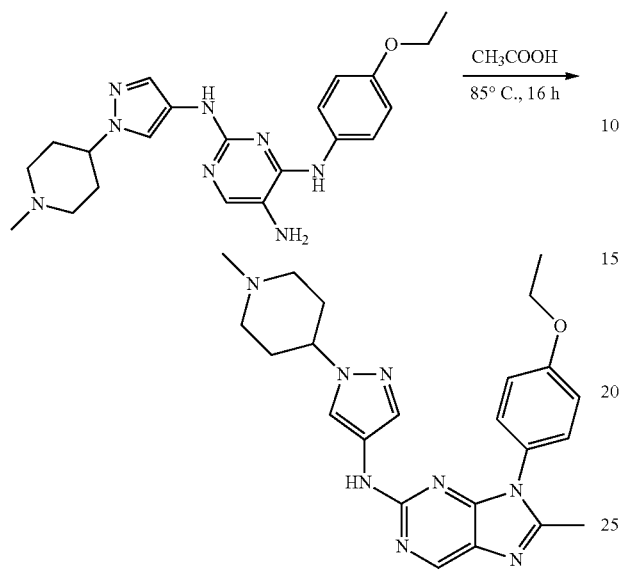

Procedure: A solution of (N⁴-(4-ethoxyphenyl)-N²-(1-(1-methylpiperidin-4-yl)-1H-pyrazol-4-yl)pyrimidine-2,4,5-triamine (0.1 g, 0.00024 mol) and glacial acetic acid (10 ml, 9.7 mol) were stirred at 85° C. for 16 h. After the completion of the reaction, the solvent was removed under reduced pressure and the resulting residue was purified by column chromatography to afford 9-(4-ethoxyphenyl)-8-methyl-N-(1-(1-methylpiperidin-4-yl)-1H-pyrazol-4-yl)-9H-purin-2-amine; yield: 49% (22 mg, pale yellow solid); LCMS: (Method A) 433.2 (M+H), RT, 2.43 min, 96.2% (Max), 93.6% (254 nm);

HPLC: (Method A) RT 2.45 min 95.5% (Max), 93.0% (254 nm);

¹H NMR: (400 MHz, DMSO-d₆): δ [ppm] 9.42 (s, 1H), 8.66 (s, 1H), 7.83 (s, 1H), 7.50 (d, J=8.6 Hz, 2H), 7.36 (s, 1H), 7.15 (d, J=8.8 Hz, 2H), 4.12-4.10 (m, 2H), 3.93-3.91 (m, 1H), 2.84-2.81 (m, 2H), 2.39 (s, 3H), 2.21 (s, 3H), 2.02-2.00 (m, 2H), 1.91-1.88 (m, 2H), 1.74-1.72 (m, 2H), 1.50-1.49 (m, 3H).

EXAMPLE 7

Synthesis of 9-(4-ethoxyphenyl)-N2-(1-(1-methylpiperidin-4-yl)-1H-pyrazol-4-yl)-9H-purine-2,8-diamine ("A7")

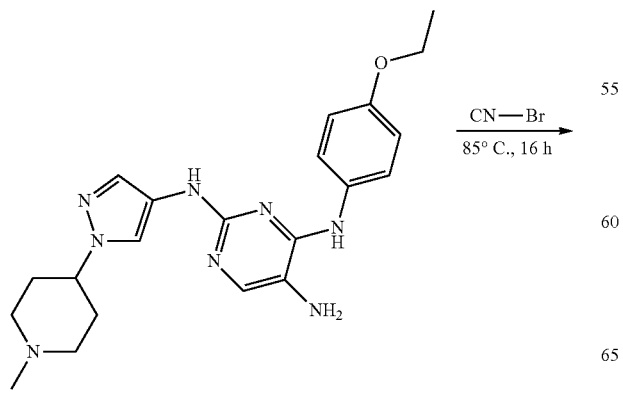

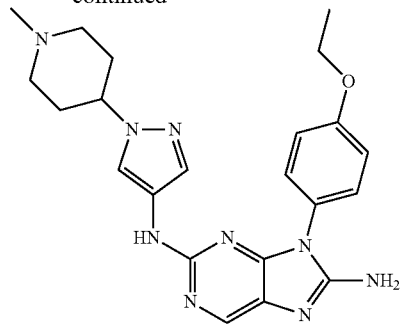

Procedure: A solution of 9-(4-ethoxyphenyl)-8-methyl-N-(1-(1-methylpiperidin-4-yl)-1H-pyrazol-4-yl)-9H-purin-2-amine (0.1 g, 0.00024 mol) and cyanic bromide (0.026 g, 0.00024 mmol) in MeCN (10 mL) and water (1 mL) were stirred at 85° C. for 16 h. After the completion of the reaction, the solvent was removed under reduced pressure and the resulting residue was purified by column chromatography to afford 9-(4-ethoxyphenyl)-8-methyl-N-(1-(1-methylpiperidin-4-yl)-1H-pyrazol-4-yl)-9H-purin-2-amine; yield: 6% (62 mg, pale brown solid); LCMS: (Method A) 434.2 (M+H), RT 1.98 min, 96.3% (Max), 94.6% (254 nm); HPLC: (Method A) RT 2.13 min 95.9% (Max), 95.0% (254 nm);

¹H NMR: (400 MHz, DMSO-d₆): δ [ppm] 8.96 (s, 1H), 8.14 (s, 1H), 7.80 (s, 1H), 7.42 (d, J=8.8 Hz, 2H), 7.31 (s, 1H), 7.13 (d, J=8.8 Hz, 2H), 6.45 (s, 1H), 4.12 (q, J=6.9 Hz, 2H), 3.96-3.90 (m, 1H), 2.85-2.82 (m, 2H), 2.21 (s, 3H), 2.03-2.00 (m, 2H), 1.91-1.88 (m, 2H), 1.88-1.74 (m, 2H), 1.39 (t, J=6.9 Hz, 3H).

EXAMPLE 8

Synthesis of N²,9-bis(1-ethyl-1H-pyrazol-4-yl)-9H-purine-2,8-diamine ("A8")

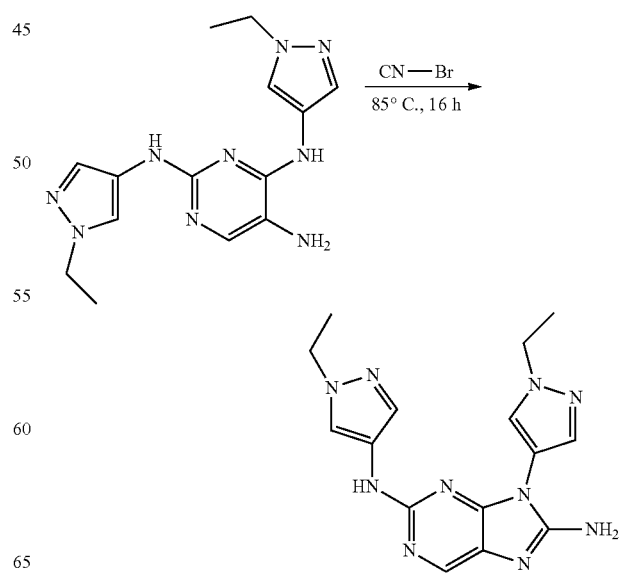

Procedure: A solution of 9-(4-ethoxyphenyl)-8-methyl-N-(1-(1-methylpiperidin-4-yl)-1H-pyrazol-4-yl)-9H-purin-2-amine (0.1 g, 0.00032 mol) and cyanic bromide (0.034 g, 0.00032 mmol) in MeCN (10 mL) and water (1 mL) were stirred at 85° C. for 16 h. After the completion of the reaction, the solvent was removed under reduced pressure and the resulting residue was purified by column chromatography to afford N2,9-bis(1-ethyl-1H-pyrazol-4-yl)-9H-purine-2,8-diamine; yield: 7% (73 mg, pale yellow solid); LCMS: (Method A) 339.0 (M+H), RT 1.93 min, 98.0% (Max), 97.8% (254 nm).

HPLC: (Method A) RT 2.04 min 97.6% (Max), 97.5% (254 nm);

$^1$H NMR: (400 MHz, DMSO-$d_6$): δ [ppm] 8.97 (s, 1H), 8.17 (s, 1H), 8.13 (s, 1H), 7.80 (s, 1H), 7.72 (s, 1H), 7.37 (s, 1H), 5.00 (s, H), 4.20-4.18 (m, 2H), 4.02-4.01 (m, 2H), 1.44 (t, J=7.2 Hz, 3H), 1.31 (t, J=7.2 Hz, 3H).

EXAMPLE 9

Synthesis of 6-(2-((1-ethyl-1H-pyrazol-4-yl)amino)-9H-purin-9-yl)-3,3-dimethylindolin-2-one ("A9")

Step 1

6-((2-chloro-5-nitropyrimidin-4-yl)amino)-3,3-dimethylindolin-2-one

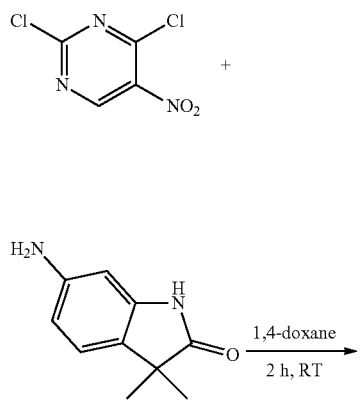

Procedure: To a stirred solution of 2,4-dichloro-5-nitropyrimidine (0.3 g, 0.00154 mol) in 1,4-dioxane (10 mL) at 0° C. was added a solution of 6-amino-3,3-dimethylindolin-2-one (0.3 g, 0.00154 mol) in 1,4-dioxane (5 mL). The reaction was stirred for 2 h. After the completion of the reaction, the solvent was removed under reduced pressure and the resulted residue was purified by column chromatography to afford 6-((2-chloro-5-nitropyrimidin-4-yl)amino)-3,3-dimethylindolin-2-one; yield: 78% (0.4 g, yellow solid); LCMS: (Method A) 334.0 (M+H).

Step 2

6-((2-(((1-ethyl-1H-Pyrazol-4-yl)amino)-5-nitropyrimidin-4-yl)amino)-3,3-dimethylindolin-2-one

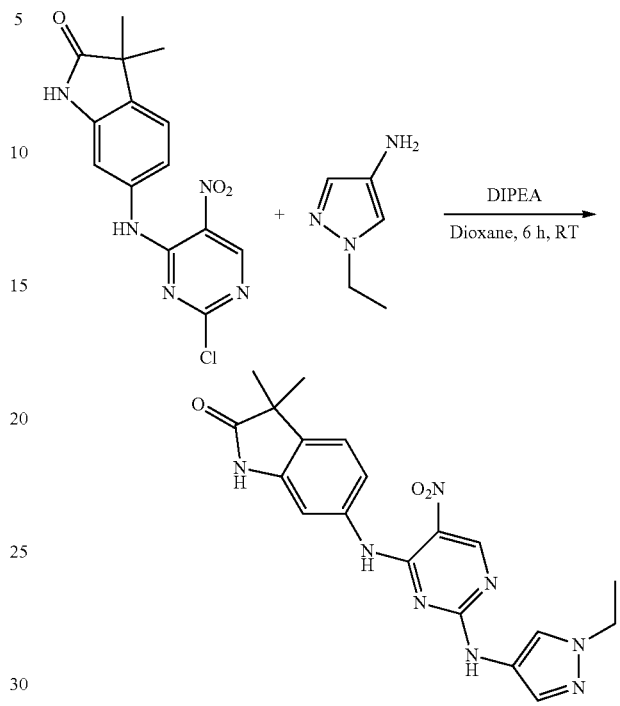

Procedure: To a stirred solution of 6-((2-chloro-5-nitropyrimidin-4-yl)amino)-3,3-dimethylindolin-2-one (0.4 g, 0.0012 mol) in 1,4-dioxane (10 mL) at 0° C. was added a solution of -ethyl-1H-pyrazol-4-amine (0.133 g, 0.0012 mol) and DIPEA (0.5 mL, 0.003 mol) in 1,4-dioxane (2 mL). The reaction was stirred for 6 h. After the completion of the reaction, the solvent was removed under reduced pressure and the resulting residue was purified by column chromatography to afford 6-((2-((1-ethyl-1H-pyrazol-4-yl)amino)-5-nitropyrimidin-4-yl)amino)-3,3-dimethylindolin-2-one; yield: 61% (0.3 g, yellow solid): LCMS: (Method A) 409.0 (M+H).

Step 3; 6-((5-amino-2-((1-ethyl-1H-Pyrazol-4-yl)amino)pyrimidin-4-yl)amino)-3,3-dimethylindolin-2-one

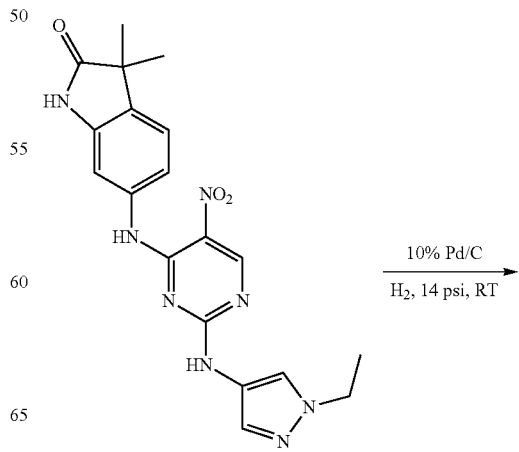

-continued

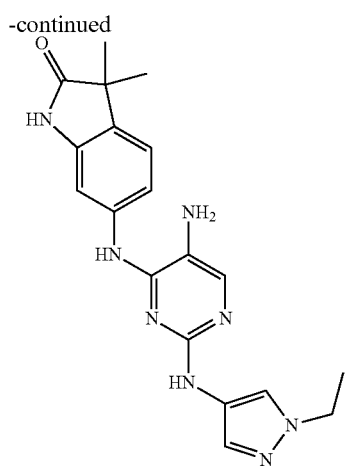

Procedure: A mixture of 6-((2-((1-ethyl-1H-pyrazol-4-yl)amino)-5-nitro-pyrimidin-4-yl)amino)-3,3-dimethylindolin-2-one (0.3 g, 0.00073 mol), Pd/C (10%, 70 mg) in $CH_3OH$ (20 mL) was hydrogenated under $H_2$ atmosphere for 5 hr. After the completion of the reaction as evidenced by TLC, the reaction mixture was filtered through Celite, washed with ethanol (10 mL). The filtrate was concentrated to get 6-((5-amino-2-((1-ethyl-1H-pyrazol-4-yl)amino)pyrimidin-4-yl)amino)-3,3-dimethylindolin-2-one; yield: 54% (0.15 g, brown liquid); LCMS: (Method A) 379.0 (M+H).

Step 4

6-(2-((1-ethyl-1H-Pyrazol-4-yl)amino)-9H-purin-9-yl)-3,3-dimethylindolin-2-one

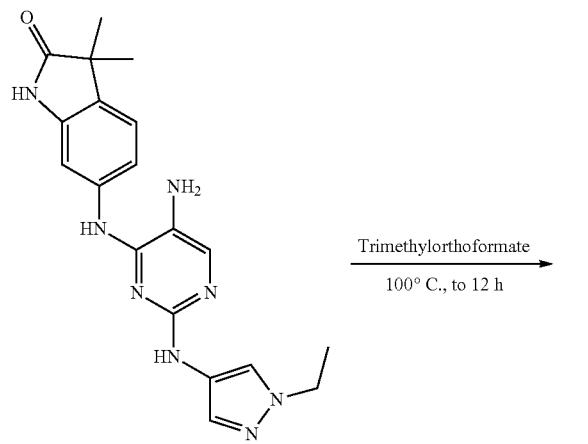

Procedure: A solution of 6-((5-amino-2-((1-ethyl-1H-pyrazol-4-yl)amino)-pyrimidin-4-ylamino)-3,3-dimethylindolin-2-one (0.15 g, 0.00039 mol) and trimethyl orthoformate (5 ml, 9.7 mol) were stirred at 100° C. for 12 h. After the completion of the reaction, the solvent was removed under reduced pressure and the resulting residue was purified by column chromatography to afford 6-(2-((1-ethyl-1H-pyrazol-4-yl)amino)-9H-purin-9-yl)-3,3-dimethylindolin-2-one; yield: 23% (33 mg, white solid); LCMS: (Method A) 389.0 (M+H), RT 2.74 min, 99.5% (Max), 99.5% (254 nm);

HPLC: (Method A) RT 2.76 min 99.3% (Max), 98.8% (254 nm);

$^1$H NMR: (400 MHz, DMSO-$d_6$): δ [ppm] 10.66 (s, 1H), 8.85 (s, 1H), 8.52 (s, 1H), 7.95 (s, 1H), 7.54 (d, J=7.9 Hz, 1H), 7.48 (s, 1H), 7.40 (d, J=7.8 Hz, 1H), 7.34 (d, J=7.5 Hz, 1H), 4.81-4.80 (m, 2H), 1.31 (s, 6H).

EXAMPLE 10

Synthesis of N-(1-(2-(1H-pyrazol-1-yl)ethyl)-1H-pyrazol-4-yl)-9-(4-ethoxyphenyl)-9H-purin-2-amine ("A10")

Step 1

1-(2-(1H-pyrazol-1-yl)ethyl)-4-nitro-1H-pyrazole

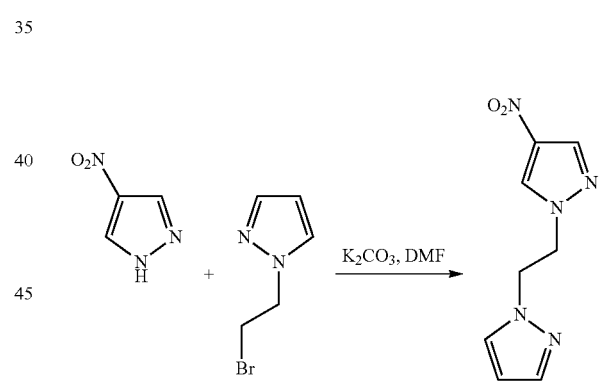

Procedure: To a stirred solution of 4-nitro-1H-pyrazole (1 g, 0.0176 mol) in DMF (5 ml) was added $K_2CO_3$ (3.6 g 0.035 mol) and 1-(2-bromoethyl)-1H-pyrazole (1.7 g, 0.0097 mol) were added. The mixture was stirred at 100° C. for 5 h. After the completion of the reaction, the solvent was evaporated and the residue was partitioned between DCM (20 mL) and $H_2O$ (20 mL), The organic layer was extracted dried using $Na_2SO_4$ and filtered. The filtrate was evaporated under reduced pressure and the crude residue was purified by column chromatography to afford 1-(2-methoxy-4-nitrophenyl)-4-methyl-piperazine; yield: 81% (1.5 g, off-white solid); LCMS: (Method A) 208.0 (M+H).

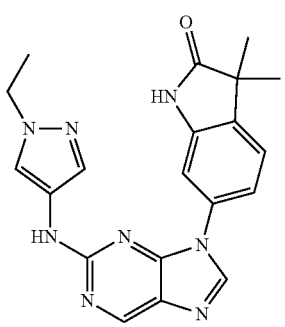

Step 2

1-(2-pyrazol-1-yl-ethyl)-1H-pyrazol-4-ylamine

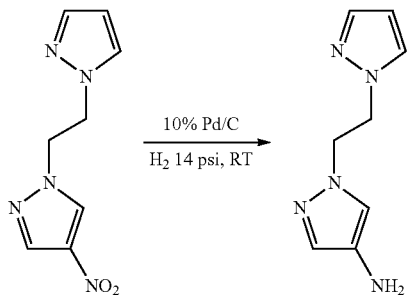 [SMILES: O=[N+]([O-])c1cnn(CCn2cccn2)c1 ; Nc1cnn(CCn2cccn2)c1]

Procedure: A mixture of 1-(2-(1H-pyrazol-1-yl)ethyl)-4-nitro-1H-pyrazole (1.5 g, 0.0072 mol), Pd/C (10%, 300 mg) in CH$_3$OH (20 mL) was hydrogenated under H$_2$ atmosphere for 5 hr. After the completion of the reaction as evidenced by TLC, the reaction mixture was filtered through Celite, washed with CH$_3$OH (10 mL). The filtrate was concentrated to get desired compound 1-(2-pyrazol-1-yl-ethyl)-1H-pyrazol-4-ylamine; yield: 70% (0.9 g, yellow liquid); LCMS: (Method A) 178.0 (M+H).

Step 3

N$^2$-(1-(2-(1H-pyrazol-1-yl)ethyl)-1H-pyrazol-4-yl)-N$^4$-(4-ethoxyphenyl)-5-nitropyrimidine-2,4-diamine

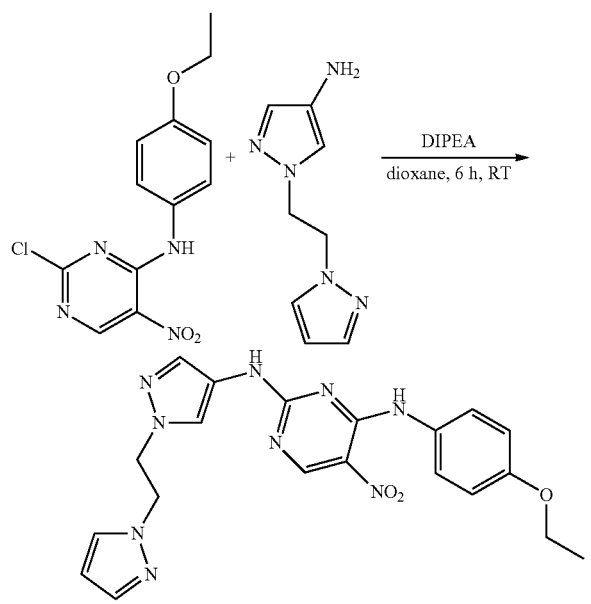

Procedure: To a stirred solution of 2-chloro-N-(4-ethoxyphenyl)-5-nitro-pyrimidin-4-amine (0.25 g, 0.00085 mol) in 1,4-dioxane (10 mL) at 0° C. was added a solution of 1-(2-pyrazol-1-yl-ethyl)-1H-pyrazol-4-ylamine (0.15 g, 0.00085 mol) and DIPEA (0.45 mL, 0.0025 mol) in 1,4-dioxane (2 mL). The reaction was stirred for 8 h. After the completion of the reaction, the solvent was removed under reduced pressure and the resulting residue was purified by column chromatography to afford N$^2$-(1-(2-(1H-pyrazol-1-yl)ethyl)-1H-pyrazol-4-yl)-N$^4$-(4-ethoxyphenyl)-5-nitropyrimidine-2,4-diamine; yield: 54% (0.2 g, yellow solid); LCMS: (Method A) 436.3 (M+H).

Step 4

N$^2$-(1-(241H-pyrazol-1-yl)ethyl)-1H-pyrazol-4-yl)-N$^4$-(4-ethoxyphenyl)pyrimidine-2,4,5-triamine

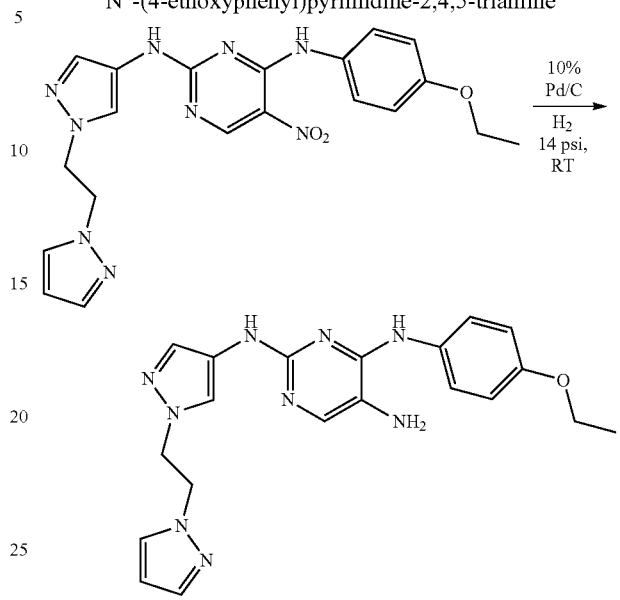

Procedure: A mixture of N$^2$-(1-(2-(1H-pyrazol-1-yl)ethyl)-1H-pyrazol-4-yl)-N$^4$-(4-ethoxyphenyl)-5-nitropyrimidine-2,4-diamine (0.2 g, 0.00046 mol), Pd/C (10%, 75 mg) in CH$_3$OH (20 mL) was hydrogenated under H$_2$ atmosphere for 5 hr. After the completion of the reaction as evidenced by TLC, the reaction mixture was filtered through Celite, washed with ethanol (10 mL). The filtrate was concentrated to get desired compound N$^2$-(1-(2-(1H-pyrazol-1-yl)ethyl)-1H-pyrazol-4-yl)-N$^4$-(4-ethoxyphenyl)pyrimidine-2,4,5-triamine; yield: 53% (0.1 g, yellow liquid); LCMS: (Method A) 406.0 (M+H).

Step 5

N-(1-(2-(1H-pyrazol-1-yl)ethyl)-1H-pyrazol-4-yl)-9-(4-ethoxyphenyl)-9H-purin-2-amine

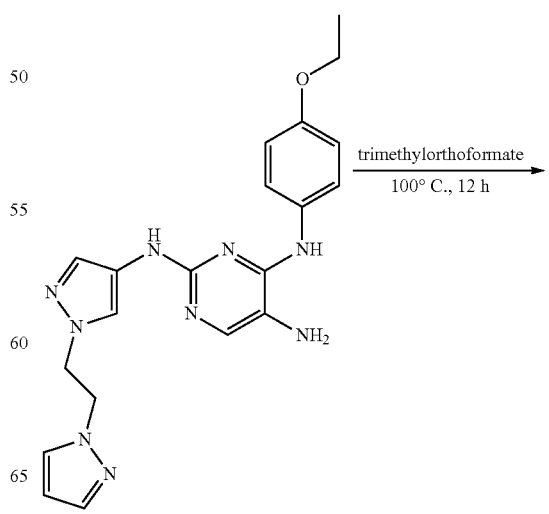

-continued

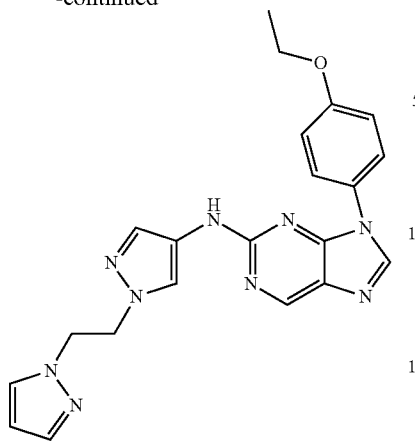

Procedure: A solution of N²-(1-(2-(1H-pyrazol-1-yl)ethyl)-1H-pyrazol-4-yl)-N⁴-(4-ethoxyphenyl)pyrimidine-2,4,5-triamine (0.1 g, 0.00024 mol) and trimethyl orthoformate (5 ml, 9.7 mol) were stirred at 100° C. for 12 h. After the completion of the reaction, the solvent was removed under reduced pressure and the resulting residue was purified by column chromatography to afford N-(1-(2-(1H-pyrazol-1-yl)ethyl)-1H-pyrazol-4-yl)-9-(4-ethoxyphenyl)-9H-purin-2-amine; yield: 25% (25 mg, off white solid); LCMS: (Method A) 416.2 (M+H), RT 3.20 min, 97.7% (Max), 96.6% (254 nm);

HPLC: (Method A) RT 3.17 min 97.6% (Max), 96.5% (254 nm);

¹H NMR: (400 MHz, DMSO-$d_6$): δ [ppm] 9.57 (s, 1H), 8.83 (s, 1H), 8.50 (s, 1H), 7.76-7.72 (m, 2H), 7.67 (s, 1H), 7.54 (s, 1H), 7.41-7.40 (m, 2H), 7.19 (d, J=8.7 Hz, 2H), 6.12 (s, 1H), 4.50 (t, J=5.5 Hz, 2H), 4.44 (t, J=5.2 Hz, 2H), 4.13-4.10 (m, 2H), 1.38 (t, J=7.0 Hz, 3H).

EXAMPLE 11

Synthesis of 9-(4-ethoxyphenyl)-N-(1-(3-(piperidin-4-yl)propyl)-1H-pyrazol-4-yl)-9H-purin-2-amine hydrochloride ("A11")

Step 1 tert-butyl 4-(3-(4-nitro-1H-pyrazol-1-yl)propyl)piperidine-1-carboxylate

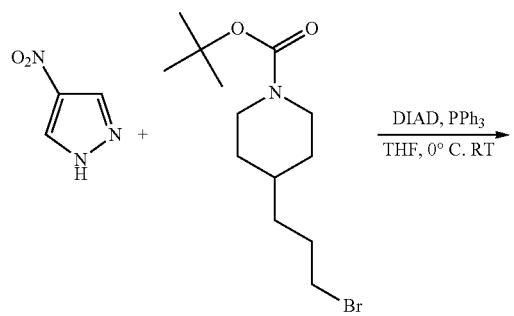

-continued

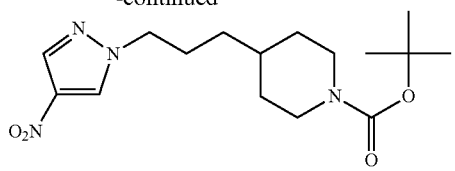

Procedure: DIAD (6.32 mL, 0.026 mol) was added dropwise to a stirred solution of 4-nitro-pyazole (1 g, 0.0088 mol), (3-aminopropyl)-piperidine-1-carboxylic acid tert-butyl ester (2.9 g, 0.0088 mol) and PPh₃ (3.5 g, 0.013 mol) in THF (50 mL) cooled to 0° C. under N₂ atmosphere. The resulting solution was stirred at 0° C. for 10 minutes then allowed to warm to room temperature and stirred overnight. The mixture was diluted with hexane (80 mL) and EtOAc (20 mL) and then stirred vigorously. The mixture was filtered and the solid was washed with hexane. The combined filtrates were evaporated and the residue was purified by chromatography to afford tert-butyl 4-(3-(4-nitro-1H-pyrazol-1-yl)propyl)piperidine-1-carboxylate; yield: 67% (2.0 g, pale yellow solid); LCMS: (Method A) 339.0 (M+H).

Step 2 tert-butyl 4-(3-(4-amino-1H-pyrazol-1-yl)propyl)piperidine-1-carboxylate

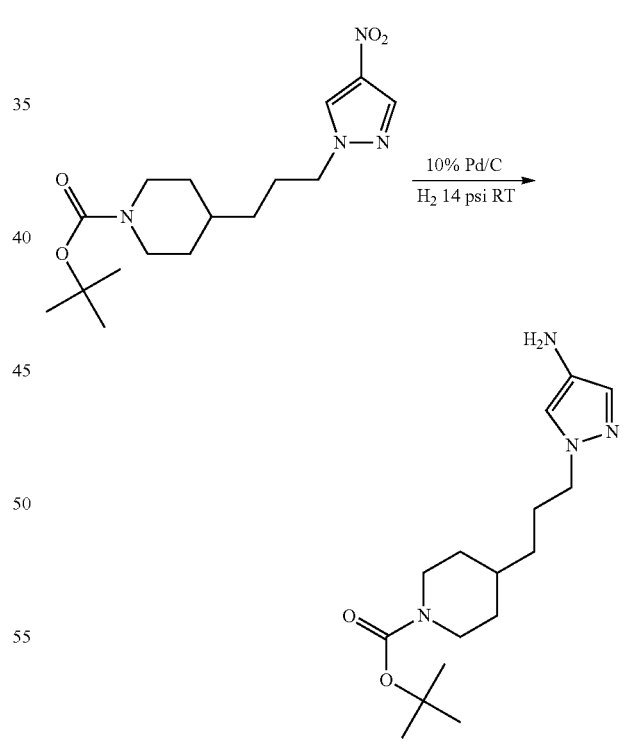

Procedure: A mixture of tert-butyl 4-(3-(4-nitro-1H-pyrazol-1-yl)propyl)-piperidine-1-carboxylate (2.0 g, 0.0059 mol), Pd/C (10%, 300 mg) in CH₃OH (20 mL) was hydrogenated under H₂ atmosphere for 5 hr. After the completion of the reaction as evidenced by TLC, the reaction mixture was filtered through Celite, washed with ethanol (10 mL). The filtrate was concentrated to get desired compound tert-butyl 4-(3-(4-amino-1H-pyrazol-1-yl)propyl)piperidine-1-carboxylate; yield: 55% (1 g, yellow liquid); LCMS: (Method A) 309.0 (M+H).

Step 3 tert-butyl 4-(3-(4-((4-((4-ethoxyphenyl)amino)-5-nitropyrimidin-2-yl)amino)-1H-pyrazol-1-yl)propyl)piperidine-1-carboxylate

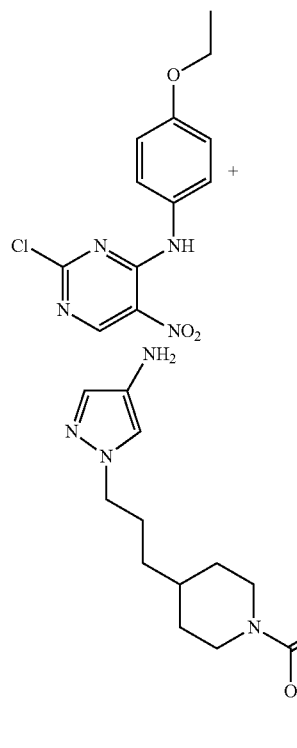

Procedure: To a stirred solution of N2-(1-(2-(1H-pyrazol-1-yl)ethyl)-1H-pyrazol-4-yl)-N4-(4-ethoxyphenyl)-5-nitropyrimidine-2,4-diamine (0.4 g, 0.0015 mol) in 1,4-dioxane (10 mL) at 0° C. was added a solution of tert-butyl 4-(3-(4-amino-1H-pyrazol-1-yl)propyl)piperidine-1-carboxylate (0.51 g, 0.00016 mol) and DIPEA (0.8 mL, 0.004 mol) in 1,4-dioxane (2 mL). The reaction was stirred for 8 h. After the completion of the reaction, the solvent was removed under reduced pressure and the resulting residue was purified by column chromatography to afford tert-butyl 4-(3-(4-((4-((4-ethoxyphenyl)amino)-5-nitropyrimidin-2-yl)amino)-1H-pyrazol-1-yl)propyl)piperidine-1-carboxylate; yield: 47% (0.2 g, yellow solid); LCMS: (Method A) 425.1 (M+H).

Step 4 tert-butyl 4-(3-(4-((5-amino-4-((4-ethoxyphenyl)amino)pyrimidin-2-yl)amino)-1H-pyrazol-1-yl)propyl)piperidine-1-carboxylate

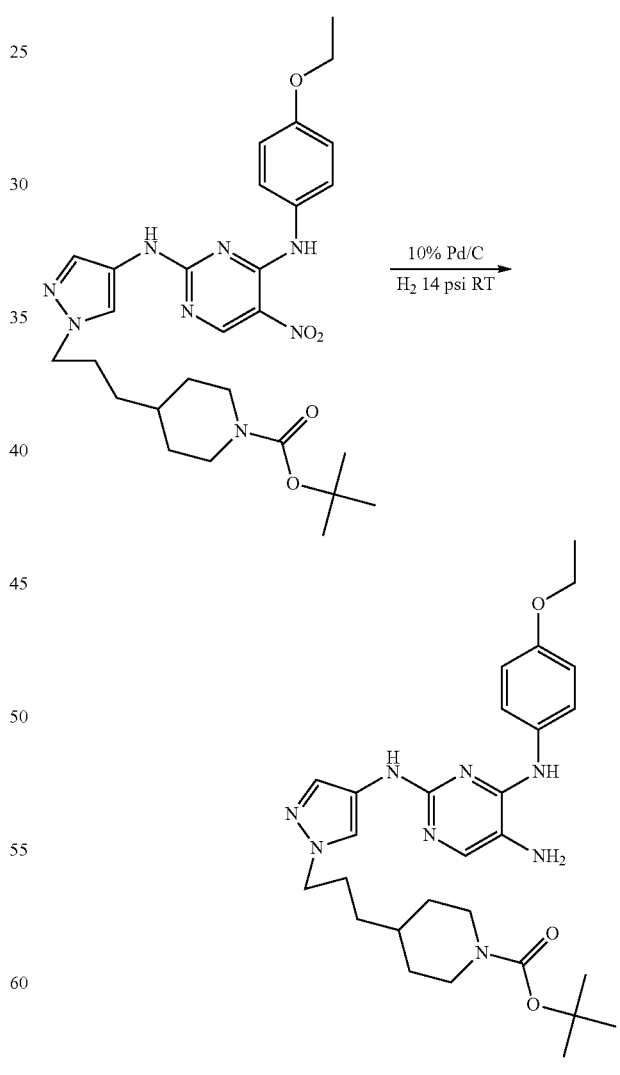

Procedure: A mixture of tert-butyl 4-(3-(4-((4-((4-ethoxyphenyl)amino)-5-nitro pyrimidin-2-yl)amino)-1H-pyrazol-1-yl)propyl)piperidine-1-carboxylate (0.2 g, 0.00035 mol), Pd/C (10%, 75 mg) in CH₃OH (20 mL) was hydrogenated under H₂ atmosphere for 5 hr. After the completion of the reaction as evidenced by TLC, the reaction mixture was filtered through Celite, washed with methanol (10 mL). The filtrate was concentrated to get desired compound tert-butyl 4-(3-(4-((5-amino-4-((4-ethoxyphenyl)amino)pyrimidin-2-yl)amino)-1H-pyrazol-1-yl) propyl)piperidine-1-carboxylate; yield: 40% (75 mg, yellow liquid); LCMS: (Method A) 537.2 (M+H).

Step 5 tert-butyl 4-(3-(4-((9-(4-ethoxyphenyl)-9H-purin-2-yl)amino)-1H-pyrazol-1-yl) propyl)piperidine-1-carboxylate

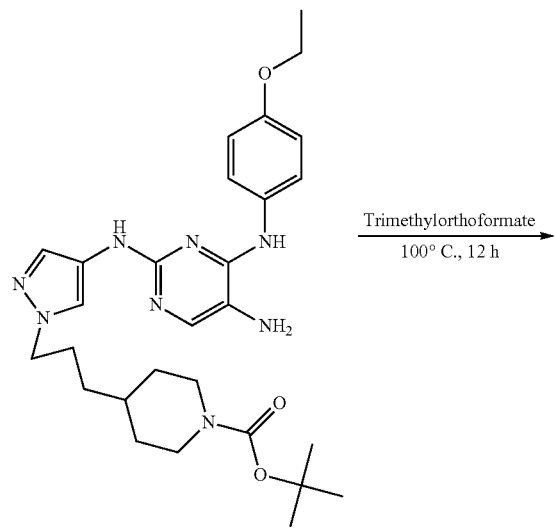

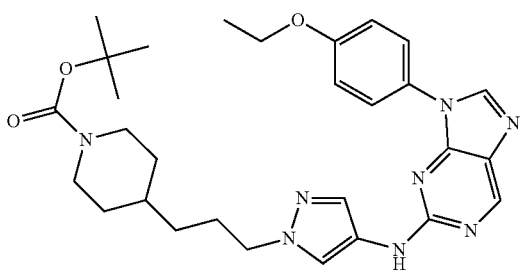

Procedure: A solution of tert-butyl 4-(3-(4-((5-amino-4-((4-ethoxyphenyl)amino) pyrimidin-2-yl)amino)-1H-pyrazol-1-yl)propyl)piperidine-1-carboxylate (0.15 g, 0.00027 mol) and trimethyl orthoformate (5 mL, 9.7 mol) were stirred at 100° C. for 12 h. After the completion of the reaction, the solvent was removed under reduced pressure and the resulting residue was purified by column chromatography to afford tert-butyl 4-(3-(4-((9-(4-ethoxyphenyl)-9H-purin-2-yl)amino)-1H-pyrazol-1-yl) propyl)piperidine-1-carboxylate; yield: 40% (0.075 mg, yellow Liquid); LCMS: (Method A) 547.2 (M+H).

Step 6

9-(4-ethoxyphenyl)-N-(1-(3-(piperidin-4-yl)propyl)-1H-Pyrazol-4-yl)-9H-purin-2-amine hydrochloride

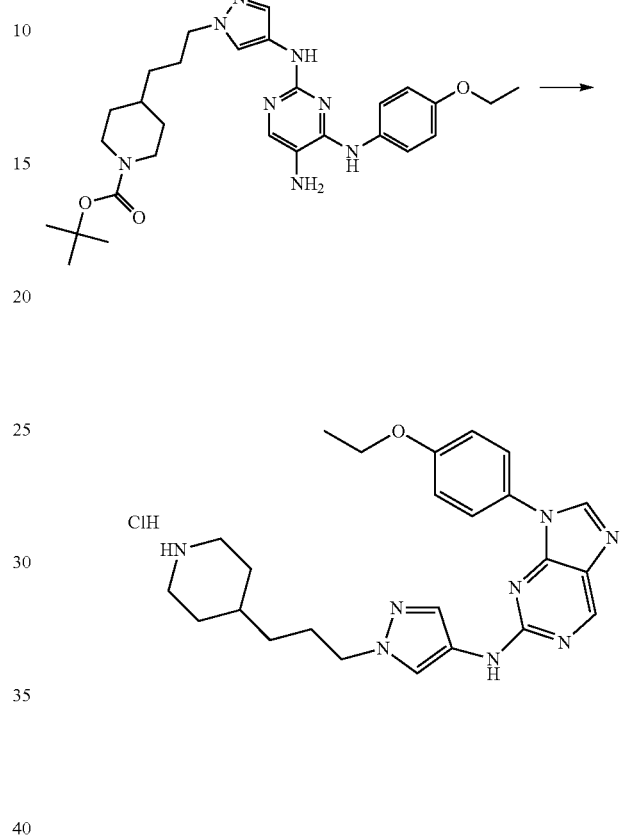

Procedure: To a stirred solution of tert-butyl 4-(3-(4-((9-(4-ethoxyphenyl)-9H-purin-2-yl)amino)-1H-pyrazol-1-yl) propyl)piperidine-1-carboxylate (75 mg, 0.0018 mol) in DCM (10 mL) was cooled to 0° C. then 5 mL of HCl in 1,4 dioxane added to the reaction mixture kept for 2 h at room temperature, then solvent was removed under reduced pressure, triturated with diethyl ether to afford 9-(4-ethoxyphenyl)-N-(1-(3-(piperidin-4-yl)propyl)-1H-pyrazol-4-yl)-9H-purin-2-amine hydrochloride; yield: 16% (10 mg, off-white solid);

LCMS: (Method A) 447.3 (M+H), RT 2.82 min, 93.5% (Max), 91.3% (254 nm);

HPLC: (Method A) RT 3.21 min 93.6% (Max), 91.0% (254 nm);

¹H NMR: (400 MHz, DMSO-d₆): δ [ppm] 9.61 (s, 1H), 8.84 (s, 1H), 8.49 (s, 1H), 7.90 (s, 1H), 7.77 (d, J=8.8 Hz, 2H), 7.48 (s, 1H), 7.16 (d, J=8.8 Hz, 2H), 4.11-4.10 (m, 2H), 4.01 (t, J=6.9 Hz, 2H), 2.94-2.91 (m, 2H), 2.46-2.43 (m, 2H), 1.74-1.71 (m, 2H), 1.56-1.53 (m, 2H), 1.37 (t, J=6.9 Hz, 3H), 1.27-1.26 (m, 2H), 1.00-0.99 (m, 2H).

EXAMPLE 12

Synthesis of 9-(4-chloro-3-fluorophenyl)-N-(1-(tetrahydro-2H-pyran-4-yl)-1H-pyrazol-4-yl)-9H-purine-2-amine ("A12")

Step 1

2-chloro-N-(4-chloro-3-fluorophenyl)-5-nitropyrimidin-4-amine

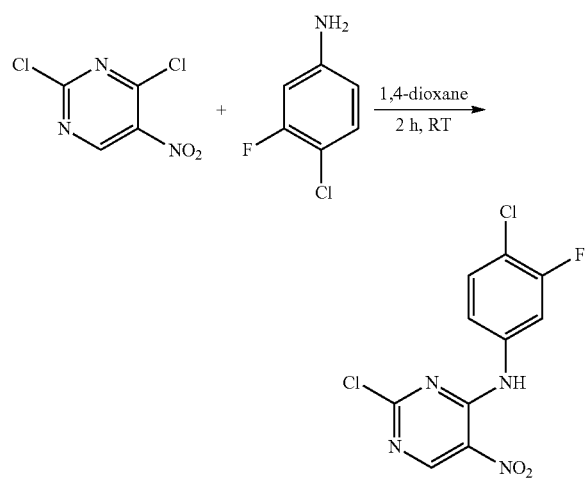

Procedure: To a stirred solution of 2,4-dichloro-5-nitropyrimidine (0.4 g, 0.0020 mol) in 1,4-dioxane (10 mL) at 0° C. was added a solution of 2-chloro-N-(4-chloro-3-fluorophenyl)-5-nitropyrimidin-4-amine (0.3 g, 0.0020 mol) in 1,4-dioxane (5 mL). The reaction was stirred for 2 h. After the completion of the reaction, the solvent was removed under reduced pressure and the resulted residue was purified by column chromatography to afford 2-chloro-N-(4-chloro-3-fluorophenyl)-5-nitropyrimidin-4-amine; yield: 50% (0.3 g, yellow solid); LCMS: (Method A) 303.0 (M+H).

Step 2

$N^4$-(4-chloro-3-fluorophenyl)-5-nitro-$N^2$-(1-(tetrahydro-2H-pyran-4-yl)-1H-pyrazol-4-yl)pyrimidine-2,4-diamine

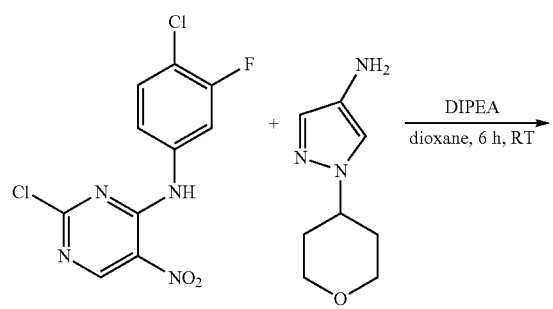

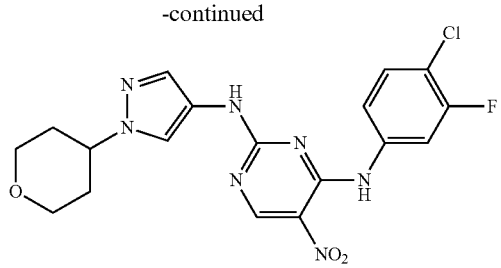

Procedure: To a stirred solution of 2-chloro-N-(4-chloro-3-fluorophenyl)-5-nitropyrimidin-4-amine (0.3 g, 0.00099 mol) in 1,4-dioxane (10 mL) at 0° C. was added a solution of 1-(tetrahydro-2H-pyran-4-yl)-1H-pyrazol-4-amine (0.162 g, 0.00099 mol) and DIPEA (0.5 mL, 0.003 mol) in 1,4-dioxane (2 mL). The reaction was stirred for 5 h. After the completion of the reaction, the solvent was removed under reduced pressure and the resulting residue was purified by column chromatography to afford $N^4$-(4-chloro-3-fluorophenyl)-5-nitro-$N^2$-(1-(tetrahydro-2H-pyran-4-yl)-1H-pyrazol-4-yl)pyrimidine-2,4-diamine; yield: 58% (0.25 g, yellow solid); LCMS: (Method A) 434.0 (M+H).

Step 3

$N^4$-(4-chloro-3-fluorophenyl)-$N^2$-(1-(tetrahydro-2H-pyran-4-yl)-1H-pyrazol-4-yl)pyrimidine-2,4,5-triamine

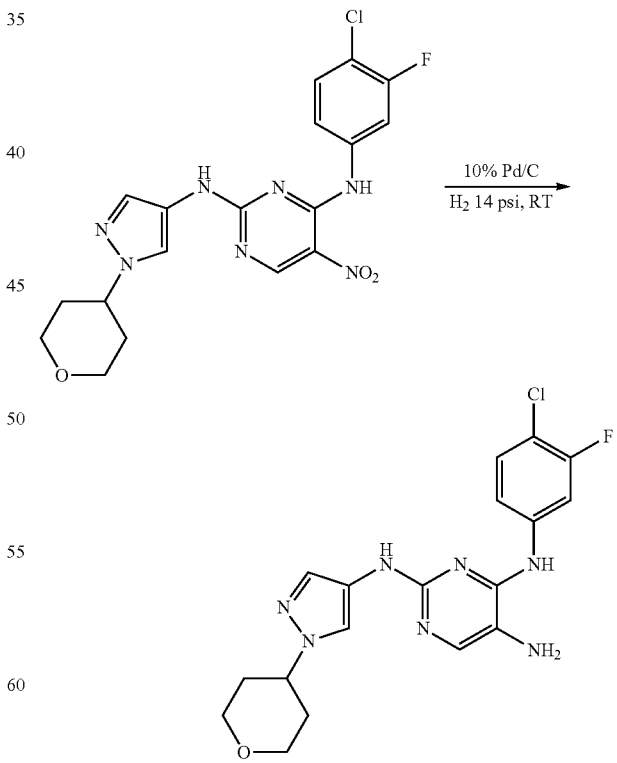

Procedure: A mixture of $N^4$-(4-chloro-3-fluorophenyl)-5-nitro-$N^2$-(1-(tetrahydro-2H-pyran-4-yl)-1H-pyrazol-4-yl)pyrimidine-2,4-diamine (0.25 g, 0.00057 mol), Pd/C (10%, 75 mg) in CH₃OH (20 mL) was hydrogenated under H₂ atmosphere for 5 hr. After the completion of the reaction as evidenced by TLC, the reaction mixture was filtered through Celite, washed with ethanol (10 mL). The filtrate was concentrated to get desired compound $N^4$-(4-chloro-3-fluoro-phenyl)-$N^2$-(1-(tetrahydro-2H-pyran-4-yl)-1H-pyrazol-4yl)pyrimidine-2,4,5-triamine; yield: 65% (0.15 g, colorless gummy liquid); LCMS: (Method A) 404.0 (M+H).

Step 4

9-(4-chloro-3-fluorophenyl)-N-(1-(tetrahydro-2H-pyran-4-yl)-1H-pyrazol-4-yl)-9H-purine-2-amine

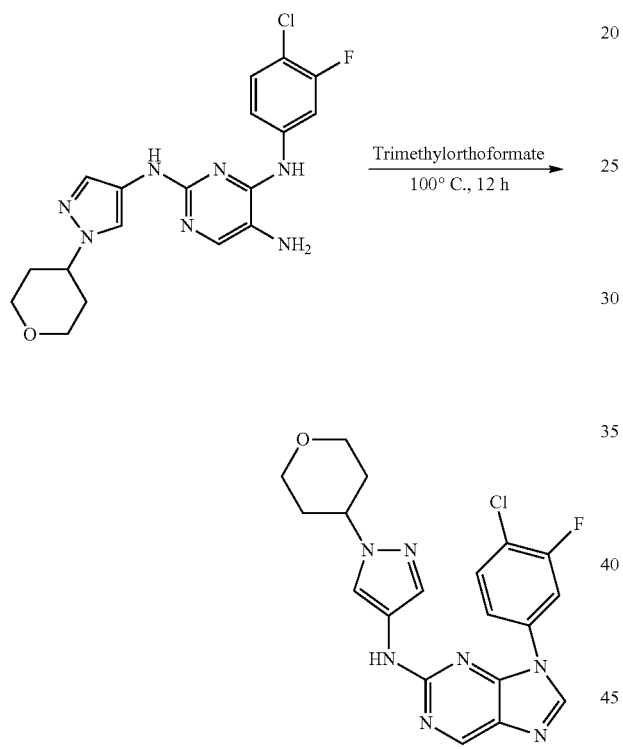

Procedure: A solution of $N^4$-(4-chloro-3-fluorophenyl)-$N^2$-(1-(tetrahydro-2H-pyran-4-yl)-1H-pyrazol-4-yl)pyrimidine-2,4,5-triamine (0.15 g, 0.00037 mol) and trimethyl orthoformate (5 ml, 9.7 mol) was stirred at 100° C. for 12 h. After the completion of the reaction, the solvent was removed under reduced pressure and the resulting residue was purified by column chromatography to afford 9-(4-chloro-3-fluorophenyl)-N-(1-(tetrahydro-2H-pyran-4-yl)-1H-pyrazol-4-yl)-9H-purin-2-amine; yield: 46% (70 mg, off-white solid); LCMS: (Method A) 414.2 (M+H), RT 3.47 min, 97.7% (Max), 97.9% (254 nm);

HPLC: (Method A) RT 3.46 min 98.1% (Max), 97.8% (254 nm);

¹H NMR: (400 MHz, DMSO-d₆): δ [ppm] 9.68 (s, 1H), 8.88 (s, 1H), 8.66 (s, 1H), 8.20-8.18 (m, 1H), 8.00 (s, 1H), 7.87 (s, 2H), 7.53 (s, 1H), 4.35-4.30 (m, 1H), 3.96-3.94 (m, 2H), 3.46-3.42 (m, 2H), 1.99-1.97 (m, 2H), 1.90-1.85 (m, 2H).

EXAMPLE 13

Synthesis of N-(1-(1-(2-methoxyethyl)piperidin-4-yl)-1H-pyrazol-4-yl)-9-(4-methoxyphenyl)-9H-purin-2-amine ("A13")

Step 1 tert-butyl 4-(4-nitro-1H-pyrazol-1-yl)piperidine-1-carboxylate

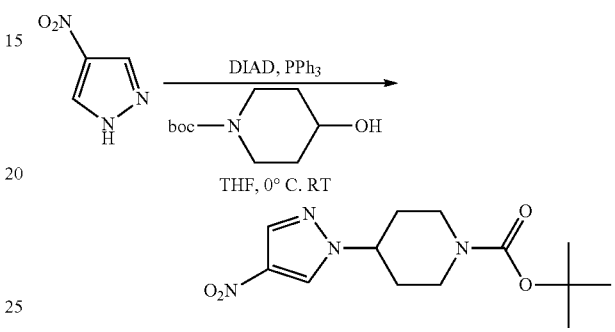

Procedure: To a stirred solution of 4-nitro-1H-pyrazole (1.5 g, 13.27 mmol), tert-butyl 4-hydroxypiperidine-1-carboxylate (2.67 g, 13.27 mmol) and PPh₃ (5.22 g, 19.90 mmol) in THF (30 mL) at 0° C. under N₂ atmosphere was added DIAD (3.92 mL, 19.90 mmol). The resulting solution was stirred at 0° C. for 10 minutes then allowed to warm to RT and stirred overnight. After the completion of the reaction, the reaction mixture was diluted with hexane (80 mL) and EtOAc (20 mL) and then stirred vigorously. The mixture was filtered and the solid washed with hexane (20 mL). The combined filtrates were evaporated and the residue was purified by chromatography to afford tert-butyl 4-(4-nitropyrazol-1-yl)piperidine-1-carboxylate; yield: 92% (3.63 g, pale yellow solid);

¹H NMR: (400 MHz, DMSO-d₆): δ [ppm] 1.42 (9H, s), 1.84-1.79 (2H, m), 2.05-2.01 (2H, m), 2.97-2.87 (2H, m). 4.47-4.40 (1H, m), 8.28 (1H, s), 8.95 (1H, s).

Step 2 tert-butyl 4-(4-amino-1H-pyrazol-1-yl)piperidine-1-carboxylate

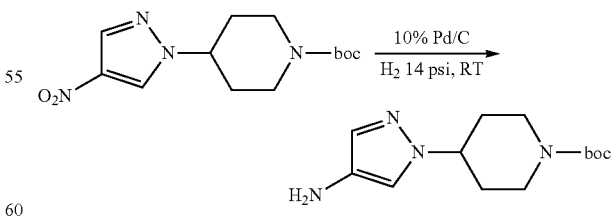

Procedure: tert-butyl 4-(4-nitropyrazol-1-yl)piperidine-1-carboxylate (3.63 g, 12.25 mmol), was dissolved in CH₃OH (20 mL) and Pd/C (10%, 300 mg) was added and hydrogenated under H₂ (14 psi) atmosphere for 18 h. After the completion of the reaction as evidenced by TLC, the reaction mixture was filtered through Celite bed, washed with ethanol (10 mL). The filtrate was concentrated to afford tert-butyl 4-(4-aminopyrazol-1-yl)piperidine-1-carboxylate; yield: 64% (2.1 g, pale yellow liquid); 
$^1$H NMR: (400 MHz, DMSO-d$_6$): δ [ppm] 1.41 (s, 9H), 1.74-1.65 (m, 2H), 1.92-1.89 (m, 2H), 2.93-2.81 (m, 2H), 3.75 (s, 2H), 3.99-3.92 (m, 2H), 4.16-4.09 (m, 1H), 6.91 (s, 1H), 7.06 (s, 1H).

Step 3

2-chloro-N-(4-methoxyphenyl)-5-nitropyrimidin-4-amine

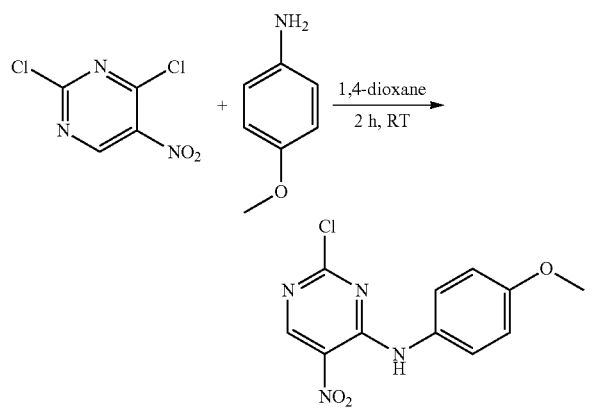

Procedure: To a stirred solution of 2,4-dichloro-5-nitropyrimidine (0.3 g, 0.00155 mol) in 1,4-dioxane (10 mL) at 0° C. was added a solution of (4-methoxyphenyl)amine (0.19 g, 0.00155 mol) in 1,4-dioxane (5 mL). The reaction was stirred for 2 h. After the completion of the reaction, the solvent was removed under reduced pressure and the resulted residue was purified by column chromatography to afford 2-chloro-N-(4-methoxyphenyl)-5-nitro-pyrimidin-4-amine; yield: 58% (0.25 g, yellow solid); LCMS: (Method A) 281.0 (M+H).

Step 4

4-{4-[4-(4-methoxy-phenylamino)-5-nitro-pyrimidin-2-ylamino]-pyrazol-1-yl}-piperidine-1-carboxylic acid tert-butyl ester

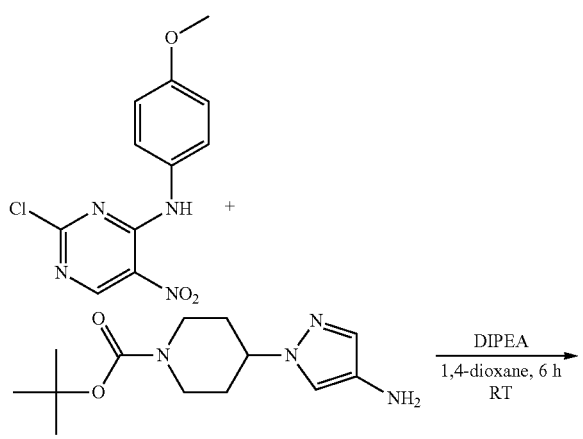

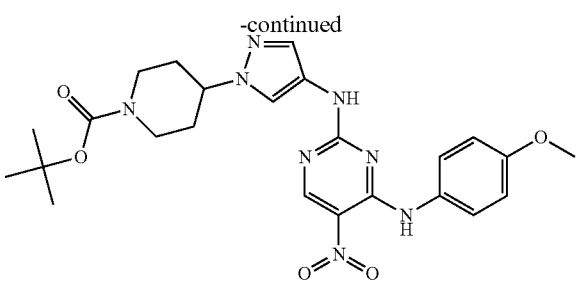

Procedure: To a stirred solution of 2-chloro-N-(4-methoxyphenyl)-5-nitro-pyrimidin-4-amine (0.5 g, 0.00178 mol) in 1,4-dioxane (10 mL) at 0° C. was added a solution of tert-butyl 4-(4-amino-1H-pyrazol-1-yl)piperidine-1-carboxylate (0.5 g, 0.00178 mol), DIPEA (0.9 mL, 0.0050 mol) in 1,4-dioxane (5 mL). The reaction was stirred for 6 h. The solvent was removed under reduced pressure and the resulting residue was purified by column chromatography to give 4-{4-[4-(4-methoxy-phenylamino)-5-nitro-pyrimidin-2-ylamino]-pyrazol-1-yl}-piperidine-1-carboxylic acid tert-butyl ester; yield: 20% (0.35 g, yellow solid); LCMS: (Method A) 511.2 (M+H).

Step 5

4-{4-[5-amino-4-(4-methoxy-phenylamino)-pyrimidin-2-ylamino]-pyrazol-1-yl}-piperidine-1-carboxylic acid tert-butyl ester

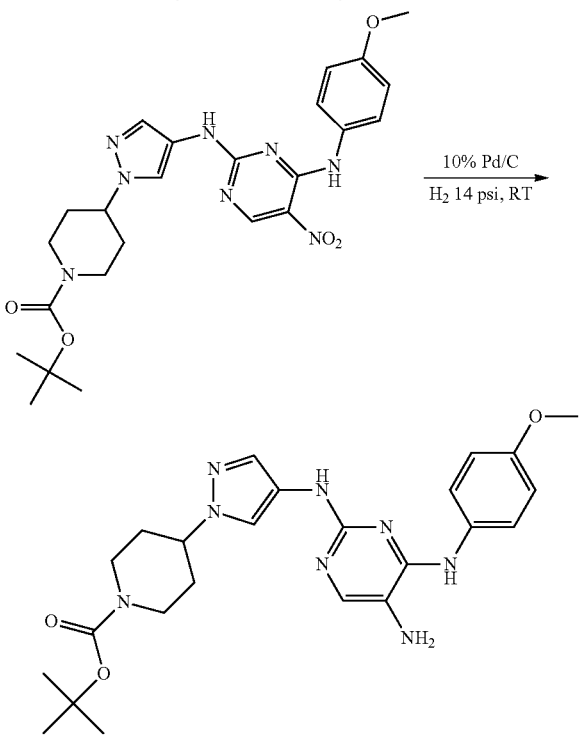

Procedure: 4-{4-[4-(4-Methoxy-phenylamino)-5-nitro-pyrimidin-2-ylamino]-pyrazol-1-yl}-piperidine-1-carboxylic acid tert-butyl ester (0.35 g, 0.00068 mol), was dissolved in CH$_3$OH (20 mL) and Pd/C (10%, 300 mg) was added and hydrogenated under H$_2$ (14 psi) atmosphere for 16 h. After the completion of the reaction as evidenced by TLC, the reaction mixture was filtered through Celite bed, washed with ethanol (10 mL). The filtrate was concentrated to afford 4-{4-[5-amino-4-(4-methoxy-phenylamino)-pyrimidin-2-ylamino]-pyrazol-1-yl}-piperidine-1-carboxylic acid tert-butyl ester; yield: 92% (0.3 g, yellow liquid); LCMS: (Method A) 481.0 (M+H).

Step 6

4-{4-[9-(4-methoxy-phenyl)-9H-purin-2-ylamino]-pyrazol-1-yl}-piperidine-1-carboxylic acid tert-butyl ester

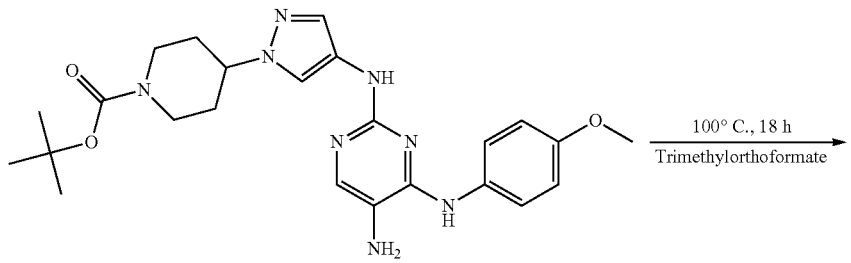

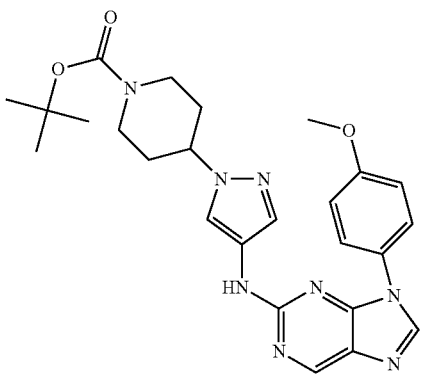

Procedure: A solution of 4-{4-[5-amino-4-(4-methoxy-phenylamino)-pyrimidin-2-ylamino]-pyrazol-1-yl}-piperidine-1-carboxylic acid tert-butyl ester (0.3 g, 0.00062 mol) and trimethyl orthoformate (5 mL) was stirred at 100° C. for 18 h. After the completion of the reaction as evidenced by TLC, the solvent was removed under reduced pressure and the resulted residue was purified by column chromatography to 4-{4-[9-(4-methoxy-phenyl)-9H-purin-2-ylamino]-pyrazol-1-yl}-piperidine-1-carboxylic acid tert-butyl ester; yield: 66% (0.2 g, off-white solid); LCMS: (Method A) 491.3 (M+H).

Step 7

9-(4-methoxyphenyl)-N-(1-(piperidin-4-yl)-1H-pyrazol-4-yl)-9H-purin-2-amine hydrochloride

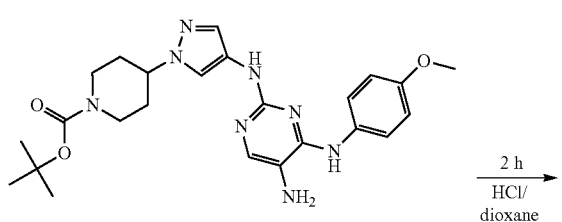

-continued

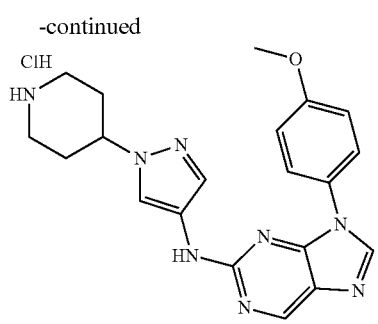

Procedure: To a stirred solution of tert-butyl 4-(4-((9-(4-methoxyphenyl)-9H-purin-2-yl)amino)-1H-pyrazol-1-yl)piperidine-1-carboxylate (0.2 g, 0.0004 mole) in a mixture of dichloromethane (10 mL)) at 0° C. was added 4M HCl in dioxane (5 mL) and stirred at for 2 h. The solid which had formed was filtered off, washed with Et₂O and dried to afford the HCl salt of 9-(4-methoxyphenyl)-N-(1-(piperidin-4-yl)-1H-pyrazol-4-yl)-9H-purin-2-amine hydrochloride; yield: 88% (0.15 g, white solid); LCMS: (Method A) 391.3 (M+H).

85
Step 8

N-(1-(1-(2-methoxyethyl)piperidin-4-yl)-1H-pyrazol-4-yl)-9-(4-methoxyphenyl)-9H-purin-2-amine

86
EXAMPLE 14

Synthesis of 9-(4-ethoxy-phenyl)-$N^2$-[1-(2-pyrazol-1-yl-ethyl)-1H-pyrazol-4-yl]-9H-purine-2,8-diamine ("A14")

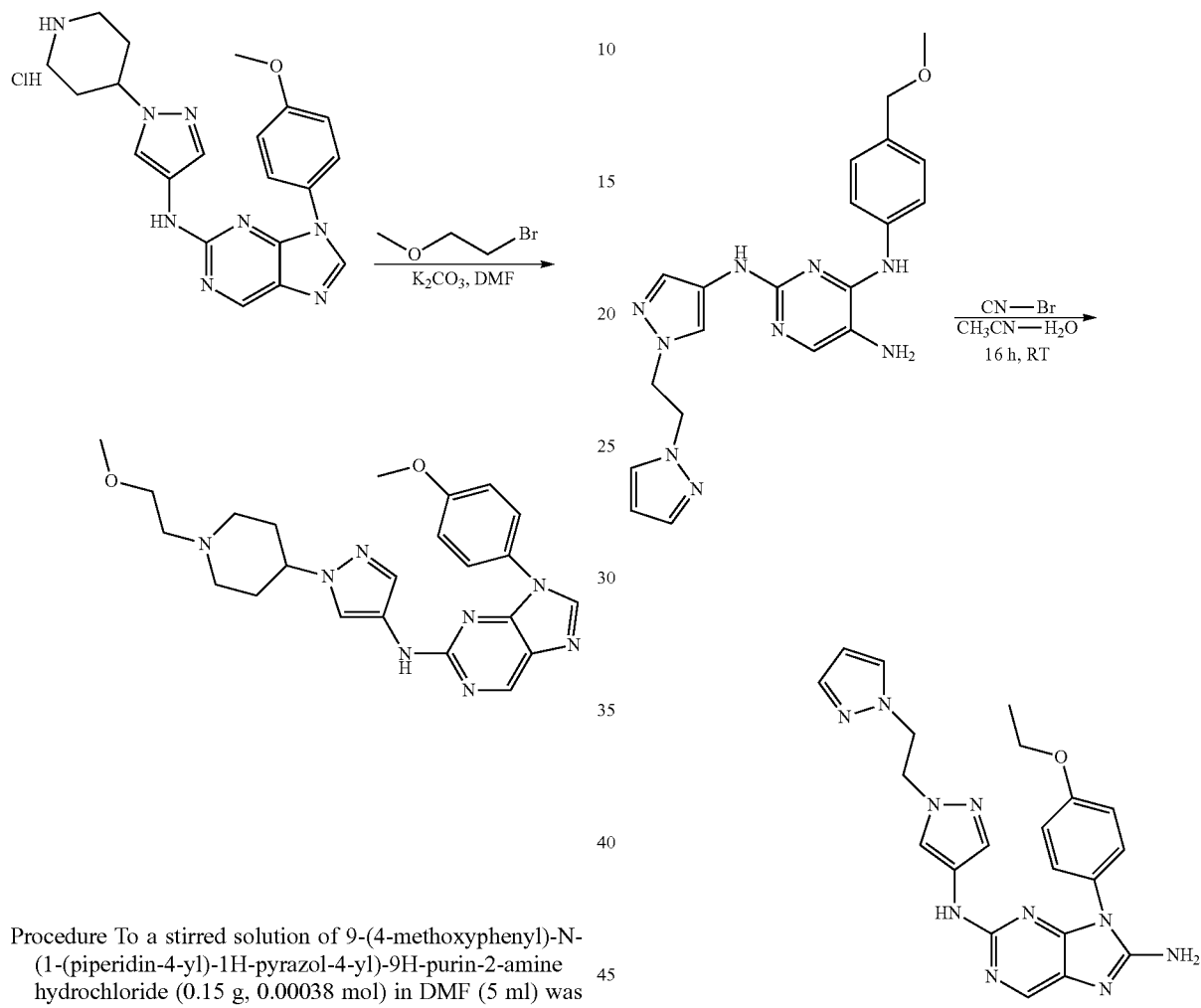

Procedure To a stirred solution of 9-(4-methoxyphenyl)-N-(1-(piperidin-4-yl)-1H-pyrazol-4-yl)-9H-purin-2-amine hydrochloride (0.15 g, 0.00038 mol) in DMF (5 ml) was added $K_2CO_3$ (0.160 g, 0.0011 mol) and 1-bromo-2-methoxyethane (0.1 mL, 0.00076 mol) were added. The mixture was stirred at 100° C. for 4 h. After the completion of the reaction, the solvent was evaporated and the residue was partitioned between DCM (20 mL) and $H_2O$ (20 mL). The organic layer was extracted dried using $Na_2SO_4$ and filtered. The filtrate was evaporated under reduced pressure and the crude residue was purified by column chromatography to afford N-(1-(1-(2-methoxyethyl)piperidin-4-yl)-1H-pyrazol-4-yl)-9-(4-methoxyphenyl)-9H-purin-2-amine; yield: 88% (0.15 g, pale yellow solid); LCMS: (Method A) 449.2 (M+H), RT 2.45 min, 94.8% (Max), 94.9% (254 nm); HPLC: (Method A) RT. 2.64 min 94.8%, (Max), 93.8% (254 nm);

$^1$H NMR: (400 MHz, DMSO-$d_6$): δ [ppm] 9.60 (s, 1H), 8.84 (s, 1H), 8.49 (s, 1H), 8.01 (s, 1H), 7.80 (d, J=8.8 Hz, 2H), 7.45 (s, 1H), 7.18 (d, J=8.9 Hz, 2H), 4.04-3.98 (m, 1H), 3.85 (s, 3H), 3.45 (t, J=5.8 Hz, 2H), 3.25 (s, 3H), 2.97-2.94 (m, 2H), 2.50-2.49 (m, 2H), 2.16-2.10 (m, 2H), 1.99-1.96 (m, 2H), 1.81-1.79 (m, 2H).

To a stirred solution of $N^4$-(4-ethoxy-phenyl)-$N^2$-[1-(2-pyrazol-1-yl-ethyl)-1H-pyrazol-4-yl]-pyrimidine-2,4,5-triamine (0.1 g, 0.00024 mol) was added cyanogen bromide (0.034 g, 0.00024 mmol) in MeCN (10 mL) and $H_2O$ (1 mL) and stirred for 16 h at RT. After the completion of the reaction, the reaction mixture was then diluted with EtOAc (50 mL) and extracted with saturated $NaHCO_3$ (3×25 mL) and brine (25 mL). The organic layer was separated and dried over $Na_2SO_4$ filtered and evaporated. The crude residue was purified by column chromatography to give 9-(4-ethoxy-phenyl)-$N^2$-[1-(2-pyrazol-1-yl-ethyl)-1H-pyrazol-4-yl]-9H-purine-2,8-diamine; yield: 20% (20 mg, pale yellow solid); LCMS: (Method A) 431.2 (M+H), RT 2.64 min, 95.5% (Max), 94.9% (254 nm); HPLC: (Method A) RT 2.64 min 94.8%, (Max), 93.6% (254 nm);

$^1$H NMR: (400 MHz, DMSO-$d_6$): δ [ppm] 8.93 (s, 1H), 8.12 (s, 1H), 7.56 (s, 1H), 7.43-7.39 (m, 5H), 7.12-7.10 (m, 2H), 6.44 (s, 2H), 6.14 (s, 1H), 4.47-4.44 (m, 2H), 4.36-4.32 (m, 2H), 4.11-4.09 (m, 2H), 1.37-1.35 (m, 3H).

EXAMPLE 15

Synthesis of N-(1-(1-methylpiperidin-4-yl)-1H-pyrazol-4-yl)-9-(quinolin-6-yl)-9H-purin-2-amine ("A15")

Step 1

N-(2-chloro-5-nitropyrimidin-4-yl)quinolin-6-amine

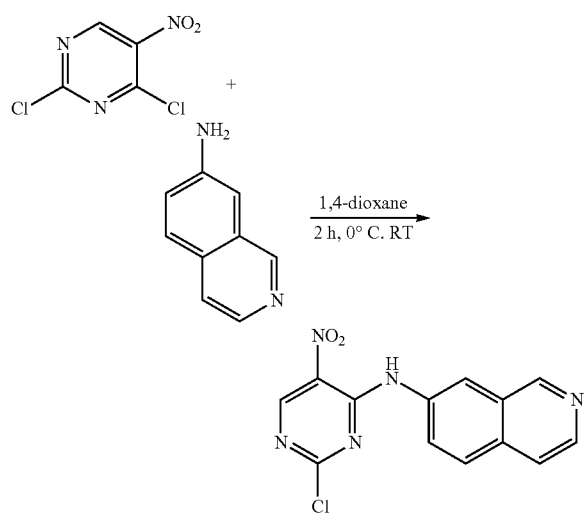

Procedure: To a stirred solution of 2,4-dichloro-5-nitropyrimidine (1 g, 0.00515 mol) in 1,4-dioxane (10 mL) at 0° C. was added a solution of quinolin-6-amine (0.81 g, 0.00567 mol)) in 1,4-dioxane (5 mL). The reaction was stirred for 2 h. After the completion of the reaction as evidenced by TLC, the reaction mixture was evaporated under reduced pressure and the resulting residue was purified by column chromatography to give the N-(2-chloro-5-nitropyrimidin-4-yl)-quinolin-6-amine; yield: 32% (0.5 g, yellow solid); LCMS: (Method A) 302.0 (M+H).

Step 2

$N^2$-(1-(1-methylpiperidin-4-yl)-1H-pyrazol-4-yl)-5-nitro-N4-(quinolin-6-yl)-pyrimidine-2,4-diamine

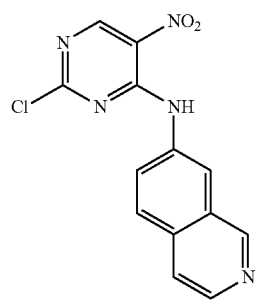

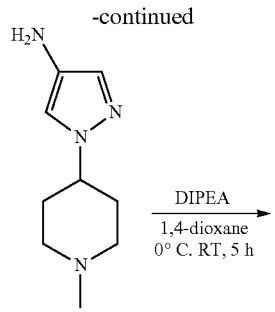

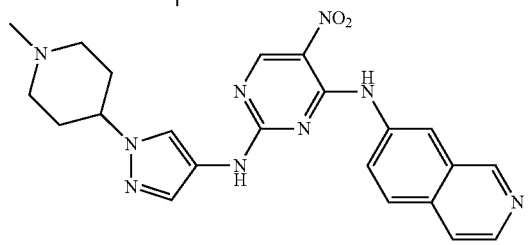

Procedure: To a stirred solution of N-(2-chloro-5-nitropyrimidin-4-yl)quinolin-6-amine (0.5 g, 0.00166 mol) in 1,4-dioxane (10 mL) at 0° C. was added a solution of 1-(1-methylpiperidin-4-yl)-1H-pyrazol-4-amine (0.32 g, 0.00182 mol), DIPEA (0.6 mL, 0.003 mol) in 1,4-dioxane (2 mL) and allowed to stir for 5 h. After the completion of the reaction as evidenced by TLC, the solvent was removed under reduced pressure and the resulting residue was purified by column chromatography to afford N2-(1-(1-methylpiperidin-4-yl)-1H-pyrazol-4-yl)-5-nitro-N4-(quinolin-6-yl)pyrimidine-2,4-diamine; yield: 67% (0.5 g, yellow solid); LCMS: (Method A) 446.2 (M+H).

Step 3

$N^2$-(1-(1-methylpiperidin-4-yl)-1H-pyrazol-4-yl)-N4-(quinolin-6-yl)pyrimidine-2,4,5-triamine

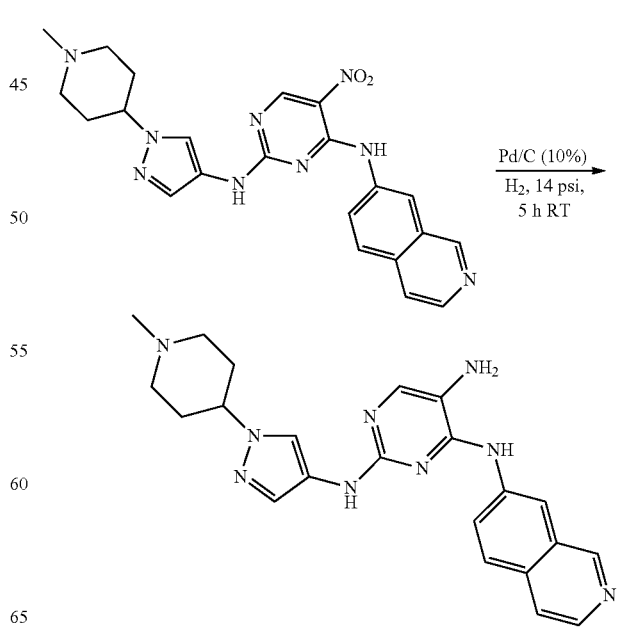

Procedure: To a mixture of N²-(1-(1-methylpiperidin-4-yl)-1H-pyrazol-4-yl)-5-nitro-N4-(quinolin-6-yl)pyrimidine-2,4-diamine (0.5 g, 0.00112 mol), in CH₃OH (20 mL) was added Pd/C (10%, 300 mg) and hydrogenated under H₂ atmosphere for 5 h. After the completion of the reaction as evidenced by TLC, the reaction mixture was filtered through Celite bed, washed with CH₃OH (10 mL). The filtrate was concentrated to get desired compound N2-(1-(1-methylpiperidin-4-yl)-1H-pyrazol-4-yl)-N4-(quinolin-6-yl)pyrimidine-2,4,5-triamine; yield: 64% (0.3 g, pale brown gummy solid); LCMS: (Method A) 416.3 (M+H).

Step 4

N-(1-(1-methylpiperidin-4-yl)-1H-pyrazol-4-yl)-9-(quinolin-6-yl)-9H-purin-2-amine

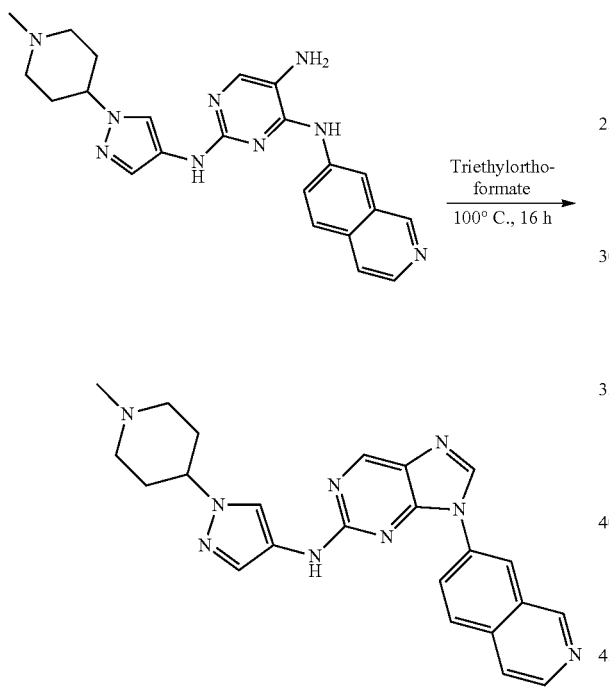

Procedure: To a stirred solution of N2-(1-(1-methylpiperidin-4-yl)-1H-pyrazol-4-yl)-N4-(quinolin-6-yl)pyrimidine-2,4,5-triamine (0.2 g, 0.00045 mol) was added triethyl orthoformate (5 mL, 0.0072 mol) and heated to 100%. After 16 h the solvent was removed under reduced pressure and the resulting residue was purified by column chromatography to afford N-(1-(1-methylpiperidin-4-yl)-1H-pyrazol-4-yl)-9-(quinolin-6-yl)-9H-purin-2-amine; yield: 24% (47 mg, off white solid); LCMS: (Method A) 426.2 (M+H), RT 1.72 min, 96.3% (Max), 95.5% (254 nm); HPLC: (Method A) RT 1.76 min, 92.9%, (Max), 94.6% (254 nm).

¹H NMR 400 MHz, DMSO-d₆: δ [ppm] 9.68 (s, 1H), 9.01 (dd, J=1.5, 4.1 Hz, 1H), 8.90 (s, 1H), 8.73 (s, 1H), 8.57 (d, J=1.9 Hz, 1H), 8.51 (d, J=7.9 Hz, 1H), 8.33 (d, J=2.3 Hz, 1H), 8.31 (d, J=2.4 Hz, 1H), 8.17 (s, 1H), 8.00 (s, 1H), 7.66 (dd, J=4.2, 8.3 Hz, 1H), 7.52 (s, 1H), 3.99 (s, 1H), 2.85-2.83 (m, 2H), 2.26 (s, 3H), 2.14-2.12 (m, 2H), 1.95-1.92 (m, 2H), 1.84-1.82 (m, 2H).

EXAMPLE 16

Synthesis of 9-(4-methoxyphenyl)-N-(1-(1-methylpiperidin-4-yl)-1H-pyrazol-4-yl)-9H-purin-2-amine ("A16")

Step 1

N⁴-(4-methoxyphenyl)-N²-(1-(1-methylpiperidin-4-yl)-1H-pyrazol-4-yl)-5-nitropyrimidine-2,4-diamine

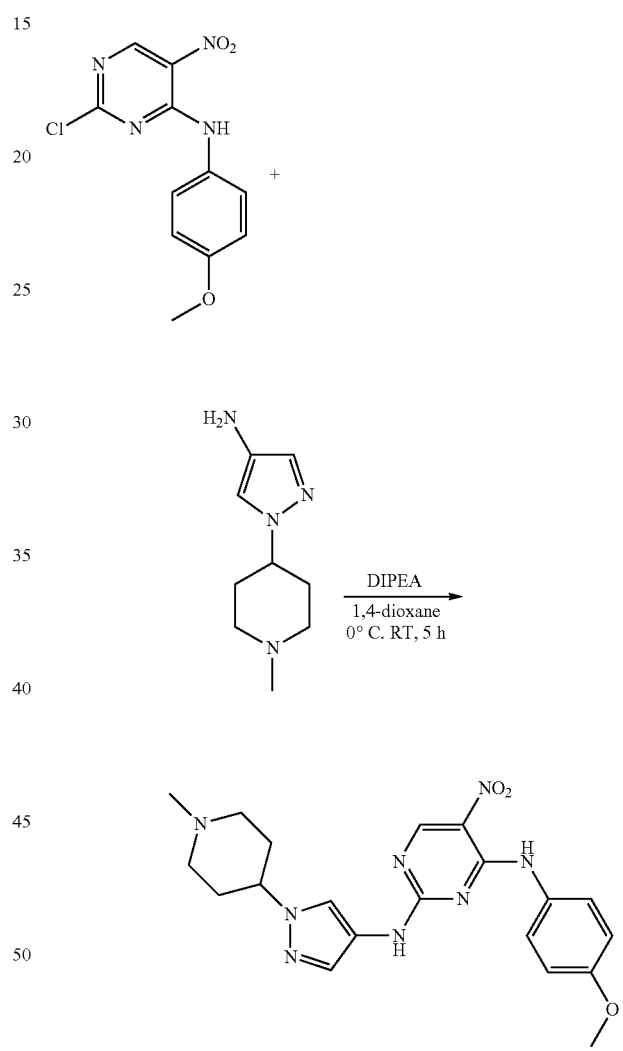

Procedure: To a stirred solution of 2-chloro-N-(4-methoxyphenyl)-5-nitro-pyrimidin-4-amine (1.5 g, 0.0053 mol) in 1,4-dioxane (10 mL) at 0° C. was added a solution of 1-(1-methylpiperidin-4-yl)-1H-pyrazol-4-amine (0.36 g, 0.002 mol), DIPEA (0.7 mL, 0.004 mol) in 1,4-dioxane (2 mL) and allowed to stir for 5 h. After the completion of the reaction as evidenced by TLC, the solvent was removed under reduced pressure and the resulting residue was purified by column chromatography to afford N⁴-(4-methoxyphenyl)-N²-(1-(1-methylpiperidin-4-yl)-1H-pyrazol-4-yl)-5-nitropyrimidine-2,4-diamine; yield: 59% (0.5 g, yellow solid); LCMS: (Method A) 425.2 (M+H).

Step 2

N4-(4-methoxyphenyl)-N2-(1-(1-methylpiperidin-4-yl)-1H-pyrazol-4-yl)Pyrimidine-2,4,5-triamine

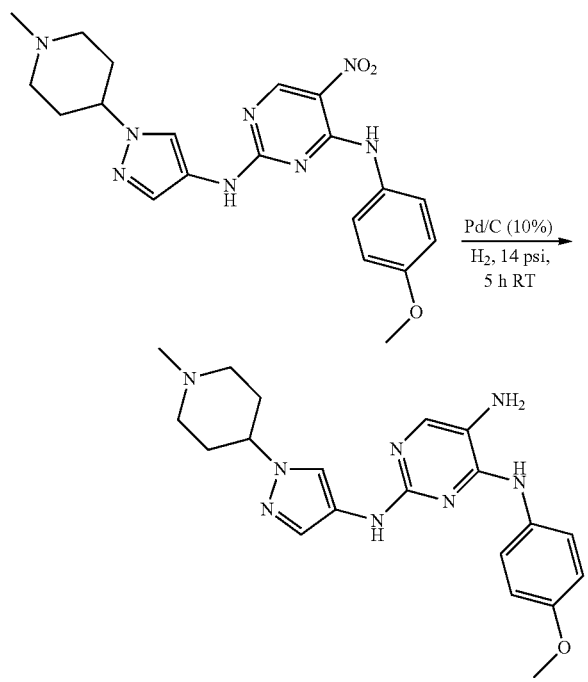

Procedure: To a mixture of N4-(4-methoxyphenyl)-N2-(1-(1-methylpiperidin-4-yl)-1H-pyrazol-4-yl)-5-nitropyrimidine-2,4-diamine (0.5 g, 0.0011 mol), in CH₃OH (20 mL) was added Pd/C (10%, 150 mg) and hydrogenated under H₂ atmosphere for 5 h. After the completion of the reaction as evidenced by TLC, the reaction mixture was filtered through celite bed, washed with CH₃OH (10 mL). The filtrate was concentrated to get desired compound N4-(4-methoxy phenyl)-N2-(1-(1-methylpiperidin-4-yl)-1H-pyrazol-4-yl)pyrimidine-2,4,5-triamine; yield: 69% (0.3 g, pale brown gummy solid); LCMS: (Method A) 395.0 (M+H).

Step 3

9-(4-methoxyphenyl)-N-(1-(1-methylpiperidin-4-yl)-1H-pyrazol-4-yl)-9H-purin-2-amine

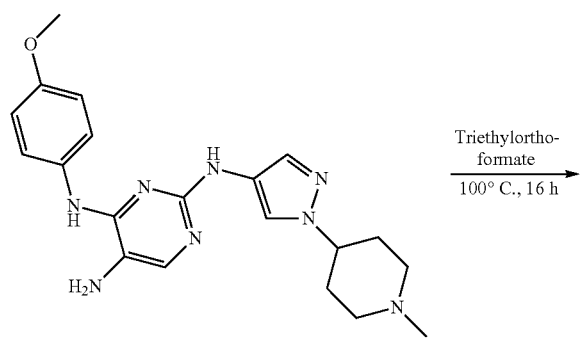

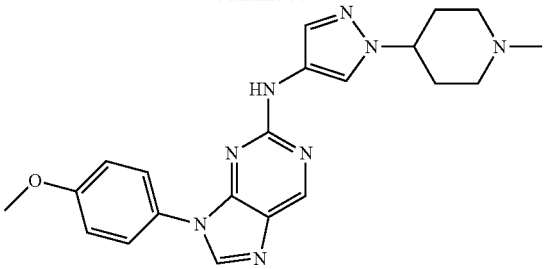

Procedure: To a stirred solution of N4-(4-methoxyphenyl)-N2-(1-(1-methylpiperidin-4-yl)-1H-pyrazol-4-yl)pyrimidine-2,4,5-triamine (0.25 g, 0.00076 mol) was added triethyl orthoformate (5 mL, 9.7 mol) and heated to 100° C. After 16 h the solvent was removed under reduced pressure and the resulting residue was purified by column chromatography to afford 9-(4-methoxyphenyl)-N-(1-(1-methylpiperidin-4-yl)-1H-pyrazol-4-yl)-9H-purin-2-amine; yield: 49% (122 mg, off white solid); LCMS: (Method A) 405.3 (M+H), RT 2.29 min, 95.9% (Max), 95.4% (254 nm); HPLC: (Method A) RT 2.27 min 98.5%, (Max), 98.3% (254 nm);

¹H NMR: 400 MHz, DMSO-d₆: δ [ppm] 9.61 (s, 1H), 8.84 (s, 1H), 8.49 (s, 1H), 8.02 (s, 1H), 7.80 (d, J=8.8 Hz, 2H), 7.45 (s, 1H), 7.18 (d, J=8.9 Hz, 2H), 7.45 (s, 1H), 7.18 (d, J=8.9 Hz, 2H), 4.05-3.97 (m, 1H), 3.86 (s, 3H), 2.84-2.82 (m, 2H), 2.20 (s, 3H), 2.06-2.00 (m, 4H), 1.88-1.81 (m, 2H).

EXAMPLE 17

Synthesis of N-(1-(4-aminocyclohexyl)-1H-pyrazol-4-yl)-9-(4-ethoxyphenyl)-9H-purin-2-amine hydrochloride ("A17")

Step 1 tert-butyl (4-(4-nitro-1H-pyrazol-1-yl)cyclohexyl) carbamate

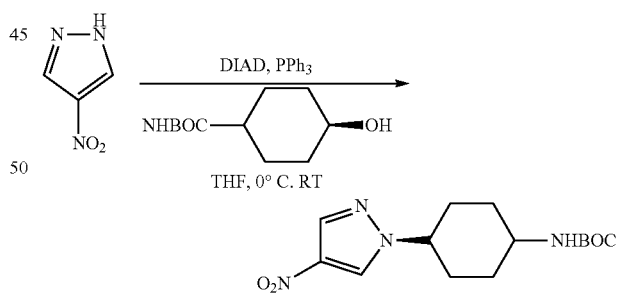

Procedure: DIAD (2.3 mL, 0.0132 mol) was added dropwise to a stirred solution of 4-nitro pyazole (1.0 g, 0.0088 mol), trans-4-Boc-amino-cyclohexanol (2.09 g, 0.00972 mol) and PPh₃ (3.47 g, 0.0132 mol) in THF (50 mL) cooled to 0° C. under N₂ atmosphere. The resulting solution was stirred at 0° C. for 10 minutes, then allowed to warm to room temperature and stirred overnight. The mixture was diluted with hexane (80 mL) and EtOAc (20 mL) and then stirred vigorously. The mixture was filtered and the solid was washed with hexane. The combined filtrates were evaporated and the residue was purified by chromatography to afford 1-methyl-4-(4-nitro-1H-pyrazol-1-yl)piperidine; yield: 36% (1 g, pale yellow solid); LCMS: (Method A) 311.0 (M+H).

Step 2 tert-butyl (4-(4-amino-1H-pyrazol-1-yl)cyclohexyl)carbamate

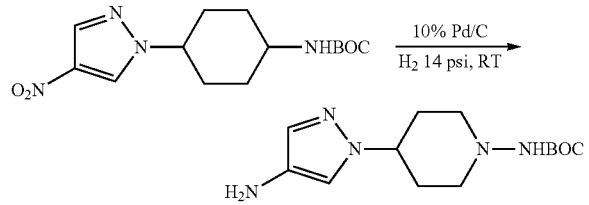

Procedure: tert-butyl (4-(4-nitro-1H-pyrazol-1-yl)cyclohexyl)carbamate (1 g, 0.0032 mol), was dissolved in CH₃OH (20 mL) and Pd/C (10%, 300 mg) was added and hydrogenated under balloon H₂ (14 psi) for 5 h. After the completion of the reaction as evidenced by TLC, the reaction mixture was filtered through Celite bed and washed with CH₃OH (10 mL). The filtrate was concentrated to get desired compound tert-butyl (4-(4-amino-1H-pyrazol-1-yl)cyclohexyl)carbamate; yield: 51% (0.5 g, yellow liquid); LCMS: (Method A) 281.1 (M+H).

Step 3 tert-butyl (4-(4-((4-ethoxyphenyl)amino)-5-nitropyrimidin-2-yl)amino)-1H-pyrazol-1-yl)cyclohexyl)carbamate

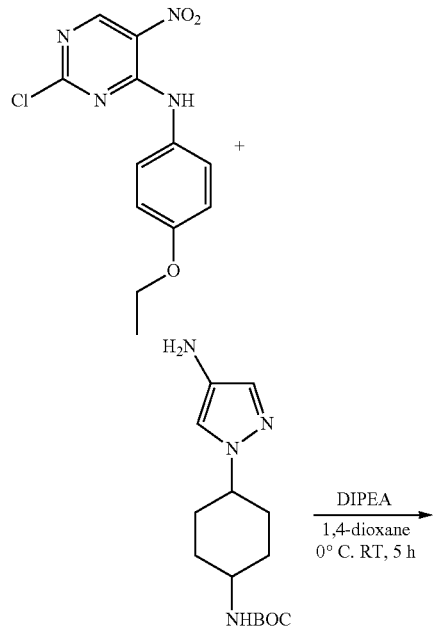

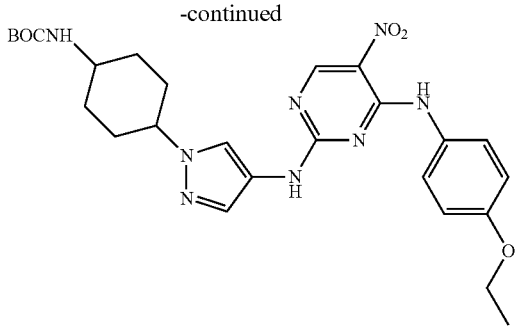

Procedure: To a stirred solution of 2-chloro-N-(4-ethoxyphenyl)-5-nitro-pyrimidin-4-amine (0.5 g, 0.0018 mol) in 1,4-dioxane (10 mL) at 0° C. was added a solution of tert-butyl (4-(4-amino-1H-pyrazol-1-yl)cyclohexyl)-carbamate (0.51 g, 0.0018 mol), DIPEA (0.63 mL, 0.036 mol) in 1,4-dioxane (2 mL) and allowed to stir for 5 h. After the completion of the reaction as evidenced by TLC, the solvent was removed under reduced pressure and the resulting residue was purified by column chromatography to afford tert-butyl (4-(4-((4-((4-ethoxyphenyl)amino)-5-nitro pyrimidin-2-yl)amino)-1H-pyrazol-1-yl)-cyclohexyl)carbamate; yield: 51% (0.5 g, yellow solid); LCMS: (Method A) 539.2 (M+H).

Step 4 tert-butyl (4-(4-((5-amino-4-((4-ethoxyphenyl)amino)pyrimidin-2-yl)amino)-1H-pyrazol-1-yl)cyclohexyl)carbamate

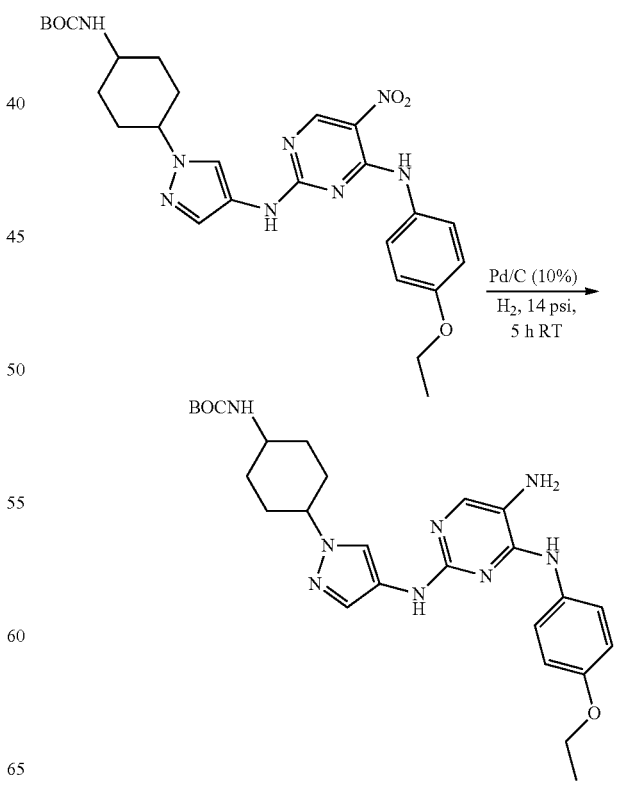

Procedure: To a mixture of tert-butyl (4-(4-((4-ethoxy-phenyl)amino)-5-nitropyrimidin-2-yl)amino)-1H-pyrazol-1-yl)cyclohexyl)carbamate (0.5 g, 0.00092 mol), in CH₃OH (20 mL) was added Pd/C (10%, 300 mg) and hydrogenated under H₂ atmosphere for 5 h. After the completion of the reaction as evidenced by TLC, the reaction mixture was filtered through celite bed, washed with CH₃OH (10 mL). The filtrate was concentrated to get desired compound tert-butyl (4-(4-((5-amino-4-((4-ethoxyphenyl)amino)pyrimidin-2-yl)amino)-1H-pyrazol-1-yl)cyclohexyl)carbamate; yield: 66% (0.3 g, pale brown gummy solid); LCMS: (Method A) 509.2 (M+H).

Step 5 tert-butyl (4-(4-((9-(4-ethoxyphenyl)-9H-purin-2-yl)amino)-1H-pyrazol-1-yl)-cyclohexyl)carbamate

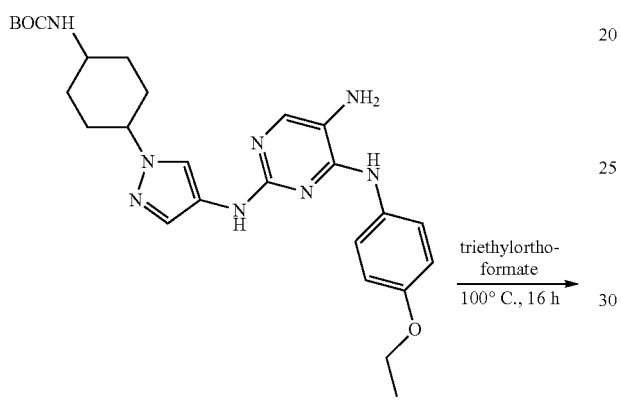

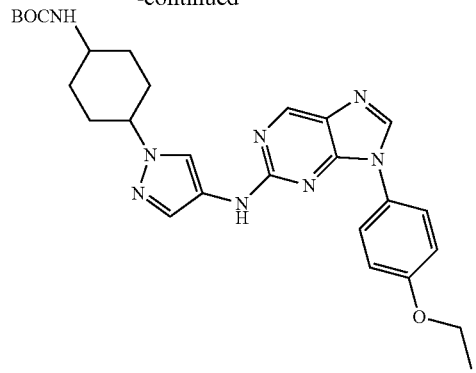

Procedure: To a stirred solution of tert-butyl (4-(4-((5-amino-4-((4-ethoxy-phenyl)amino)pyrimidin-2-yl)amino)-1H-pyrazol-1-yl)cyclohexyl)carbamate (0.3 g, 0.00058 mol) was added triethyl orthoformate (5 mL, 9.7 mol) and heated to 100° C. After 16 h the solvent was removed under reduced pressure and the resulting residue was purified by column chromatography to afford tert-butyl (4-(4-((9-(4-ethoxyphenyl)-9H-purin-2-yl)amino)-1H-pyrazol-1-yl)-cyclohexyl)carbamate; yield: 53% (160 mg, off white solid); LCMS: (Method A) 519.2 (M+H).

Step 6

N-(1-(4-aminocyclohexyl)-1H-pyrazol-4-yl)-9-(4-ethoxyphenyl)-9H-purin-2-amine hydrochloride

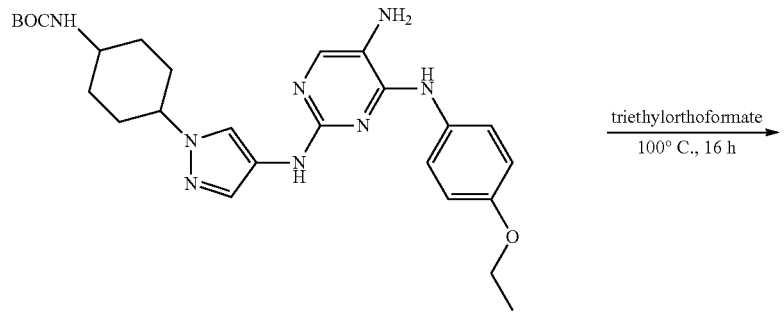

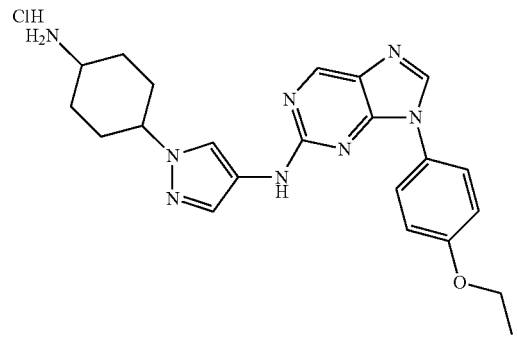

Procedure: A stirred solution of tert-butyl (4-(4-((9-(4-ethoxyphenyl)-9H-purin-2-yl)amino)-1H-pyrazol-1-yl)cyclohexyl)carbamate (160 mg, 0.00030 mol) in DCM (10 mL) was cooled to 0° C., then 5 mL of HCl in 1,4 dioxane added to the reaction mixture and kept for 2 h at room temperature, then solvent was removed under reduced pressure, triturated with diethyl ether to afford N-(1-(4-aminocyclohexyl)-1H-pyrazol-4-yl)-9-(4-ethoxyphenyl)-9H-purin-2-amine hydrochloride; yield: 85% (120 mg, off white solid); LCMS: (Method A) 419.3 (M+H), RT 2.65 min, 98.1% (Max), 97.9% (254 nm); HPLC: (Method A) RT 2.66 min 97.7%, (Max), 96.5% (254 nm);

$^1$H NMR: 400 MHz, DMSO-d$_6$: δ [ppm] 9.68 (s, 1H), 8.87 (s, 1H), 8.54 (s, 1H), 8.02 (s, 1H), 7.76 (d, J=8.8 Hz, 2H), 7.55 (s, 1H), 7.15 (d, J=8.9 Hz, 2H), 4.20 (s, 1H), 4.12-4.10 (m, 2H), 2.23-2.21 (m, 2H), 1.09-1.85 (m, 4H), 1.78-1.67 (m, 2H), 1.37 (t, J=6.9 Hz, 3H).

EXAMPLE 18

Synthesis of [9-(4-methoxy-phenyl)-9H-purin-2-yl]-(1H-pyrazol-4-yl)-amine ("A18")

Step 1

4-[4-(4-methoxy-phenylamino)-5-nitro-pyrimidin-2-ylamino]-pyrazole-1-carboxylic acid tert-butyl ester

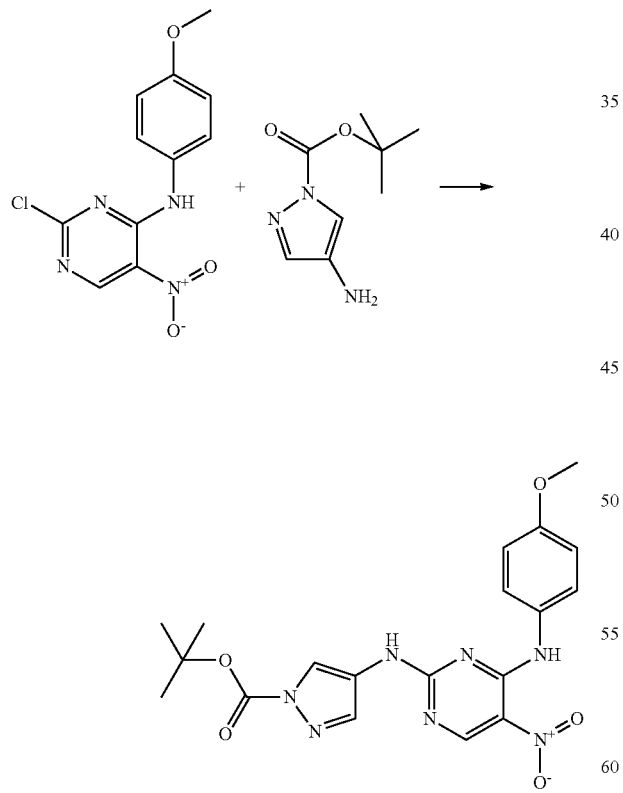

Procedure: 2-chloro-5-nitro-pyrimidin-4-yl)-(4-methoxy-phenyl)-amine (223.20 mg; 0.80 mmol; 1.00 eq.) and 4-amino-pyrazole-1-carboxylic acid tert-butyl ester (160.27 mg; 0.87 mmol; 1.10 eq.) were weighed into a reaction vial. Then, N-ethyldiisopropylamine (148.76 μl; 0.87 mmol; 1.10 eq.) and 1,4-dioxane (2 mL) were added. The reaction mixture was stirred at room temperature for six hours. Water was added to the reaction mixture. The precipitate was filtered off, washed with water and dried under vacuum to give 4-[4-(4-methoxy-phenylamino)-5-nitro-pyrimidin-2-ylamino]-pyrazole-1-carboxylic acid tert-butyl ester; yield: 286 mg of orange crystals (84%); HPLC/MS conditions B: 428.2 (M+H), RT 2.443 min.

Step 2

4-[5-Amino-4-(4-methoxy-phenylamino)-pyrimidin-2-ylamino]-pyrazole-1-carboxylic acid tert-butyl ester

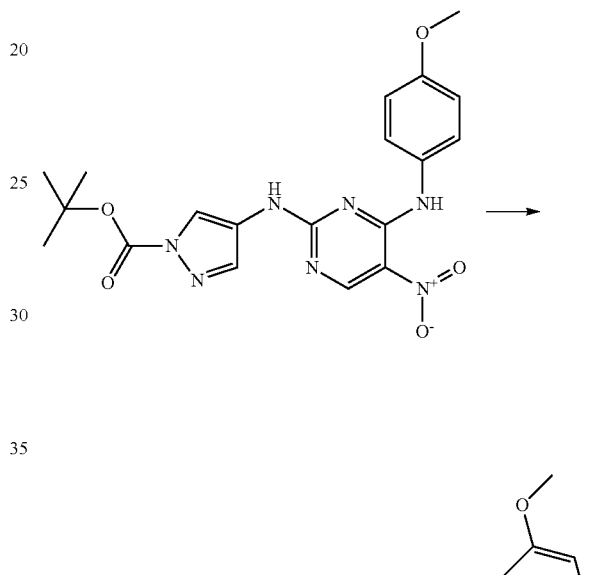

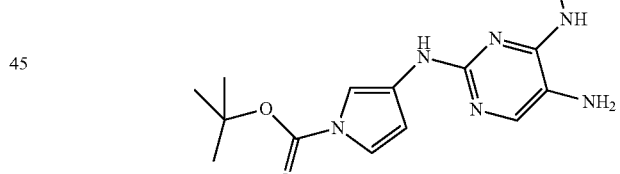

Procedure: To a mixture of 4-[4-(4-methoxy-phenylamino)-5-nitro-pyrimidin-2-ylamino]-pyrazole-1-carboxylic acid tert-butyl ester (0.278 g, 0.00065 mol) in CH$_3$OH (5 mL) and THF (5 mL) was added Pd/C (5%, 300 mg) and the mixture was hydrogenated under H$_2$ atmosphere for 5 h. After the completion of the reaction as evidenced by HPLC, the reaction mixture was filtered through celite bed, washed with CH$_3$OH (10 mL). The filtrate was concentrated to get desired compound 4-[5-amino-4-(4-methoxy-phenyl-amino)-pyrimidin-2-ylamino]-pyrazole-1-carboxylic acid tert-butyl ester; yield: 245 mg of grey crystals (95%); HPLC/MS conditions A: 398.2 (M+H), RT 1.436 min.

Step 3

4-[9-(4-Methoxy-phenyl)-9H-purin-2-ylamino]-pyrazole-1-carboxylic acid tert-butyl ester

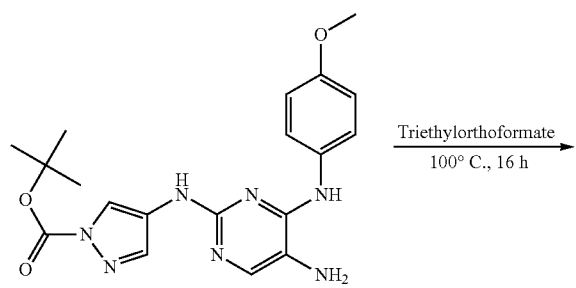

Triethylorthoformate
100° C., 16 h

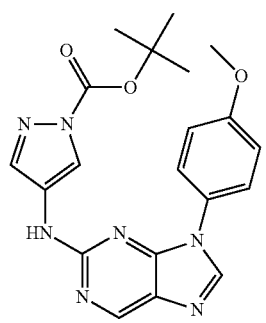

Procedure: 4-[5-amino-4-(4-methoxy-phenylamino)-pyrimidin-2-ylamino]-pyrazole-1-carboxylic acid tert-butyl ester (39.74 mg; 0.10 mmol; 1.00 eq.) was weighed into a reaction vial. Then, diethoxymethoxy-ethane (0.95 ml) is added. Finally, the reaction mixture was stirred at 100° C. for 16 h. The reaction mixture was concentrated and purified via chromatography using dichloromethane/methanol: 95/5; yield: 64 mg of white material (95%); HPLC/MS conditions A: 408.2 (M+H), RT 1.799 min.

Step 4

[9-(4-methoxy-phenyl)-9H-purin-2-yl]-(1H-pyrazol-4-yl)-amine

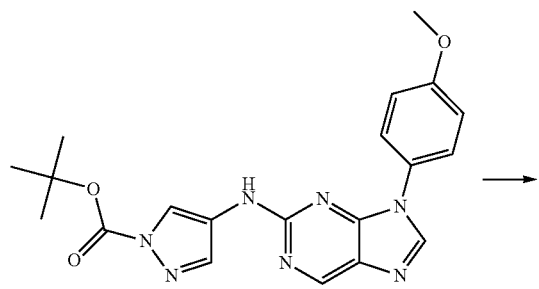

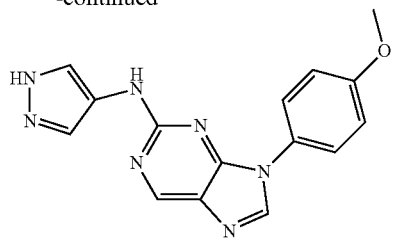

Procedure: 4-[9-(4-Methoxy-phenyl)-9H-purin-2-ylamino]-pyrazole-1-carboxylic acid tert-butyl ester (60.00 mg; 0.15 mmol; 1.00 eq.) was dissolved in 1,4-dioxane (3 mL). Then, HCl in dioxane (288.00 µl; 9.40 mmol; 63.83 eq.) was added. The reaction mixture was stirred at room temperature for two days. An extraction was performed with DCM and sodium hydroxide. The organic phase was dried with $Na_2SO_4$, concentrated and evaporated under vacuum; ield: 45 mg of yellow material (99%); HPLC/MS conditions A: 308.2 (M+H), RT 1.448 min; $^1$H NMR: (400 MHz, DMSO-$d_6$) δ [ppm] 9.50 (s, 1H), 8.84 (s, 1H), 8.45 (s, 1H), 7.78 (m, 4H), 7.17 (d, 2H), 3.86 (s, 3H).

EXAMPLE 19

Synthesis of [9-(4-methoxy-phenyl)-9H-purin-2-yl]-(1-methyl-1H-pyrazol-3-yl)-amine ("A19")

Step 1

N4-(4-methoxy-phenyl)-N2-(1-methyl-1H-pyrazol-3-yl)-5-nitro-pyrimidine-2,4-diamine

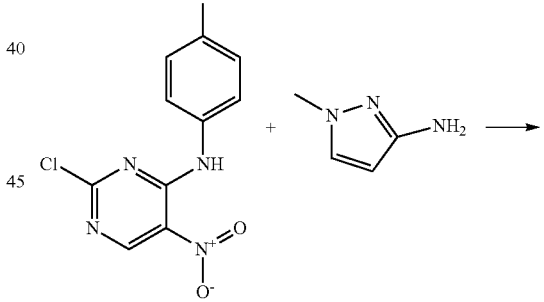

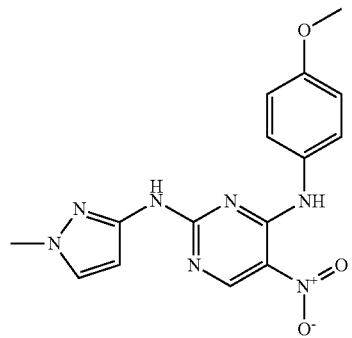

Procedure: (2-chloro-5-nitro-pyrimidin-4-yl)-(4-methoxy-phenyl)-amine (561.33 mg; 2.00 mmol; 1.00 eq.) was dissolved in 1,4-dioxane (4 mL). Then, 1-methyl-1H-pyrazol-3-ylamine (220.27 mg; 2.20 mmol; 1.10 eq.) and N-ethyldiisopropylamine (374.13 μl; 2.20 mmol; 1.10 eq.) were added. The reaction was stirred at room temperature for 14 h. Water was added to the reaction mixture. The precipitate was filtered off, washed with water and dried under vacuum to give N4-(4-methoxy-phenyl)-N2-(1-methyl-1H-pyrazol-3-yl)-5-nitro-pyrimidine-2,4-diamine; yield: 598 mg of yellow crystals (88%); HPLC/MS conditions B: 342.1 (M+H), RT 2.086 min.

Step 2

N4-(4-methoxy-phenyl)-N2-(1-methyl-1H-pyrazol-3-yl)-pyrimidine-2,4,5-triamine

Procedure: To a mixture of N4-(4-methoxy-phenyl)-N2-(1-methyl-1H-pyrazol-3-yl)-5-nitro-pyrimidine-2,4-diamine (0.6 g, 0.00018 mop in THF (10 mL) was added Pd/C (5%, 200 mg) and the mixture was hydrogenated under H₂ atmosphere for 19 h. After the completion of the reaction as evidenced by HPLC, the reaction mixture was filtered through celite bed, washed with CH₃OH (10 mL). The filtrate was concentrated to get desired compound N4-(4-methoxy-phenyl)-N2-(1-methyl-1H-pyrazol-3-yl)-pyrimidine-2,4,5-triamine; yield: 560 mg of brown material; HPLC/MS conditions A: 312.2 (M+H), RT 1.324 min.

Step 3

[9-(4-methoxy-phenyl)-9H-purin-2-yl]-(1-methyl-1H-pyrazol-3-yl)-amine

Procedure: N4-(4-methoxy-phenyl)-N2-(1-methyl-1H-pyrazol-3-yl)-pyrimidine-2,4,5-triamine (155.67 mg; 0.50 mmol; 1.00 eq.) was weighed into a reaction vial. Then, diethoxymethoxy-ethane (4.8 mL) was added. The reaction mixture was stirred at 100° C. overnight. The reaction mixture was concentrated and dried under vacuum; yield: 145 mg of beige material; HPLC/MS conditions A: LCMS: 322.2 (M+H), RT 1.559 min; ¹H NMR: (400 MHz, DMSO-d₆) δ [ppm] 9.76 (s, 1H), 8.86 (s, 1H), 8.52 (s, 1H), 7.84-7.74 (m, 2H), 7.52 (d, J=2.2 Hz, 1H), 7.20-7.10 (m, 2H), 6.58 (d, J=2.2 Hz, 1H), 3.85 (s, 3H), 3.74 (s, 3H).

EXAMPLE 20

Synthesis of [9-(4-methoxy-phenyl)-9H-purin-2-yl]-(1-phenyl-1H-pyrazol-4-yl)-amine ("A20")

Step 1

N4-(4-methoxy-phenyl)-5-nitro-N2-(1-phenyl-1H-pyrazol-4-yl)-Pyrimidine-2,4-diamine

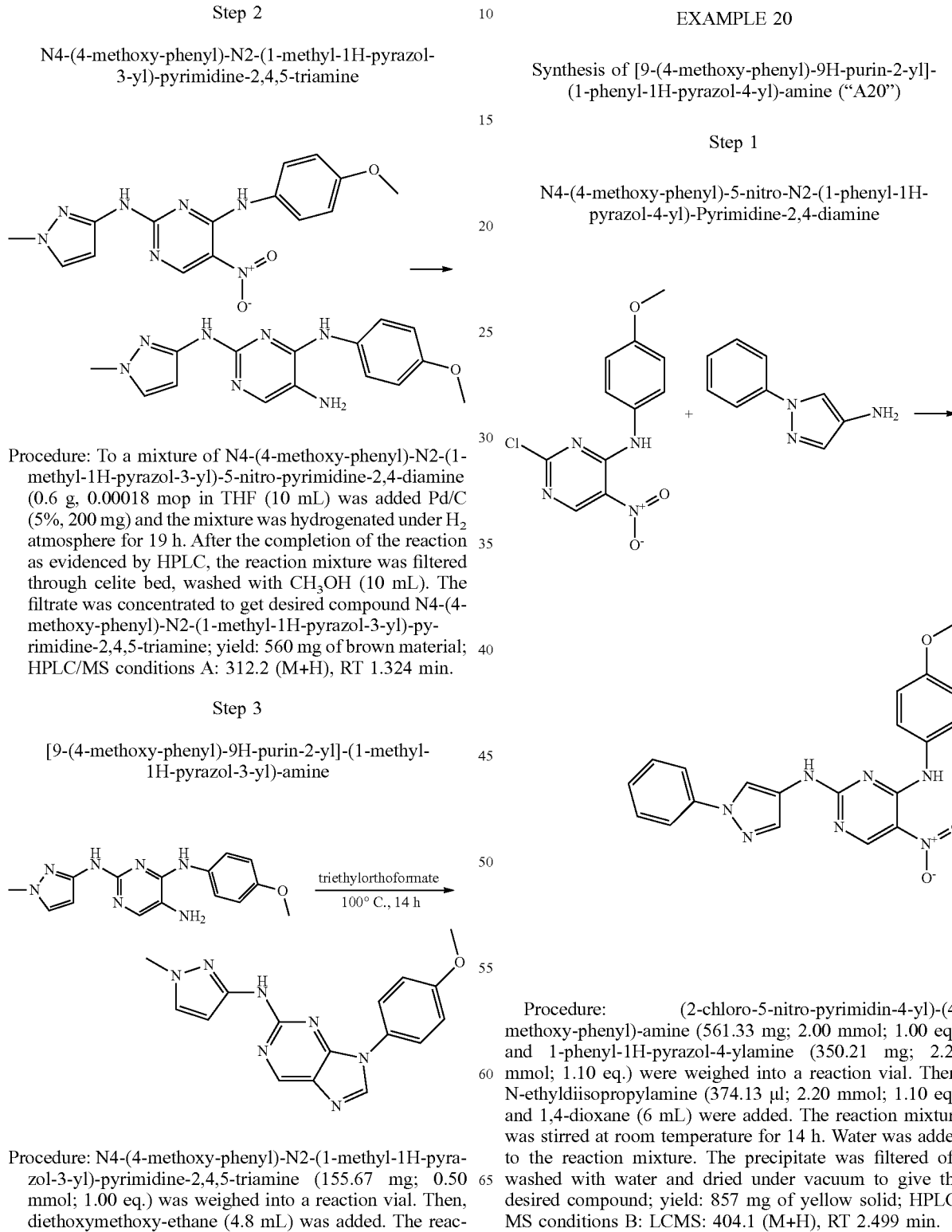

Procedure: (2-chloro-5-nitro-pyrimidin-4-yl)-(4-methoxy-phenyl)-amine (561.33 mg; 2.00 mmol; 1.00 eq.) and 1-phenyl-1H-pyrazol-4-ylamine (350.21 mg; 2.20 mmol; 1.10 eq.) were weighed into a reaction vial. Then, N-ethyldiisopropylamine (374.13 μl; 2.20 mmol; 1.10 eq.) and 1,4-dioxane (6 mL) were added. The reaction mixture was stirred at room temperature for 14 h. Water was added to the reaction mixture. The precipitate was filtered off, washed with water and dried under vacuum to give the desired compound; yield: 857 mg of yellow solid; HPLC/MS conditions B: LCMS: 404.1 (M+H), RT 2.499 min.

Step 2

N4-(4-methoxy-phenyl)-N2-(1-phenyl-1H-pyrazol-4-yl)-pyrimidine-2,4,5-triamine

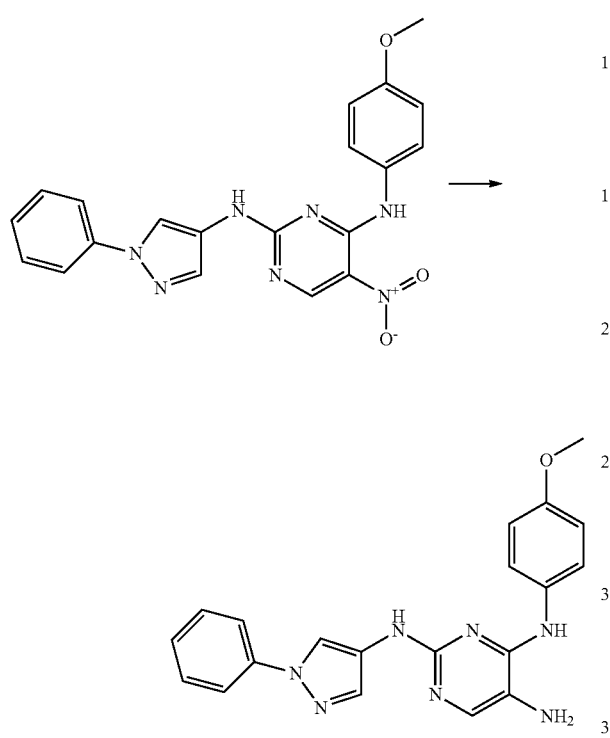

Procedure: To a mixture N4-(4-methoxy-phenyl)-5-nitro-N2-(1-phenyl-1H-pyrazol-4-yl)-pyrimidine-2,4-diamine (0.1 g, 0.00025 mol) in THF (10 mL) was added Pd/C (5%, 200 mg) and the mixture was hydrogenated under $H_2$ atmosphere for 15 h. After the completion of the reaction as evidenced by HPLC, the reaction mixture was filtered through celite bed, washed with $CH_3OH$ (10 mL). The filtrate was concentrated to get desired compound N4-(4-methoxy-phenyl)-N2-(1-phenyl-1H-pyrazol-4-yl)-pyrimidine-2,4,5-triamine; yield: 93 mg of green solid; HPLC/MS conditions A: 374.2 (M+H), RT. 1.447 min.

Step 3

[9-(4-methoxy-phenyl)-9H-purin-2-yl]-(1-phenyl-1H-pyrazol-4-yl)-amine

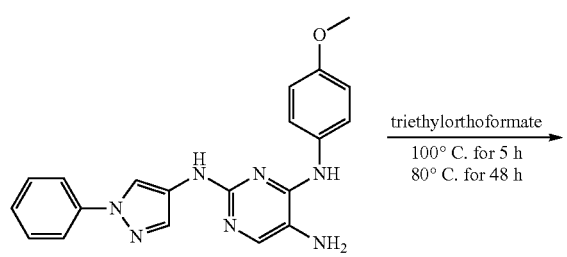

triethylorthoformate
100° C. for 5 h
80° C. for 48 h

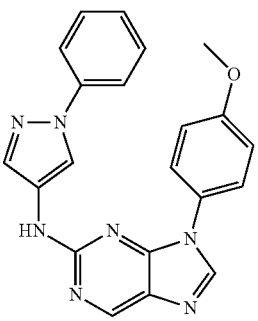

Procedure: N4-(4-methoxy-phenyl)-N2-(1-phenyl-1H-pyrazol-4-yl)-pyrimidine-2,4,5-triamine (302 mg; 0.81 mmol; 1.00 eq.) were weighed into a reaction vial. Then, diethoxymethoxy-ethane (7.70 ml) was added. The reaction mixture was stirred at 100° C. for 5 hours and 48 h at 80° C. The reaction mixture was concentrated and purified by chromatography using dichloromethan/methanol: 95/5; yield: 140 mg of white solid (45%); HPLC/MS conditions A: 384.2 (M+H), RT 1.896 min; $^1$H NMR: (400 MHz, DMSO-$d_6$) δ [ppm] 9.83 (s, 1H), 8.91 (s, 1H), 8.63 (s, 1H), 8.52 (s, 1H), 7.84 (d, J=8.7 Hz, 2H), 7.78 (s, 1H), 7.68 (d, J=8.1 Hz, 2H), 7.49 (m, 2H), 7.33-7.26 (m, 2H), 7.22 (d, J=8.7 Hz, 2H), 3.88 (s, 3H).

HPLC/MS conditions C for examples 21-31:

column: Chromolith PerformanceROD RP-18e, 100×3 mm gradient: A:B=99:1 to 0:100 in 3.5 min flow rate: 2.0 ml/min eluent A: water+0.05% formic acid Eluent B: acetonitrile+0.04% formic acid wavelength: 220 nm mass spectroscopy: positive mode

EXAMPLE 21

Synthesis of (1-methyl-1H-pyrazol-4-yl)-{9-[4-(1-methyl-1H-pyrazol-4-yl)-phenyl]-9H-purin-2-yl}-amine ("A21")

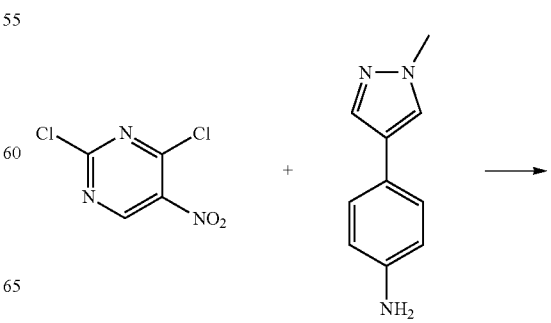

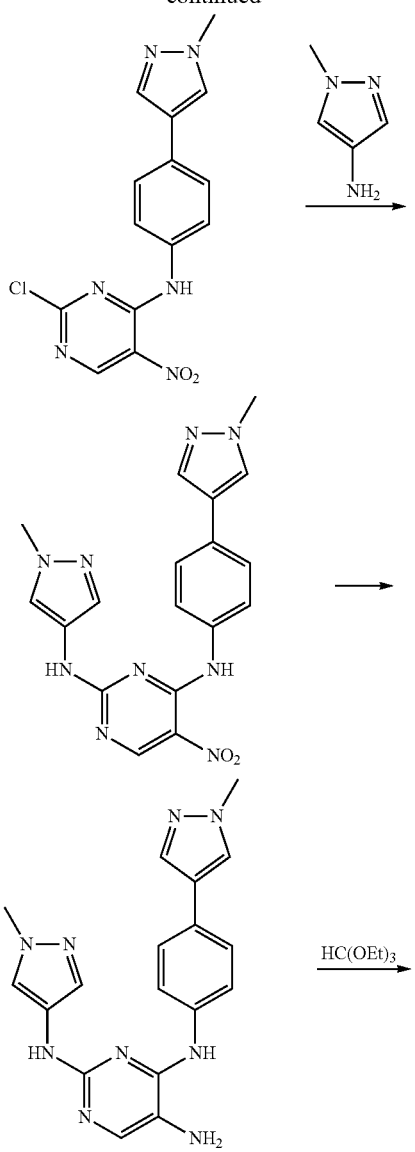
The synthesis is performed analogously to previous examples (1,2,3,4,5); LC/MS (method A) 2.66 min, [M+H] 372.
The compound N-(2,3-dihydroxy-propyl)-4-[2-(1-ethyl-1H-pyrazol-4-ylamino)-purin-9-yl]-benzamide ("A22")
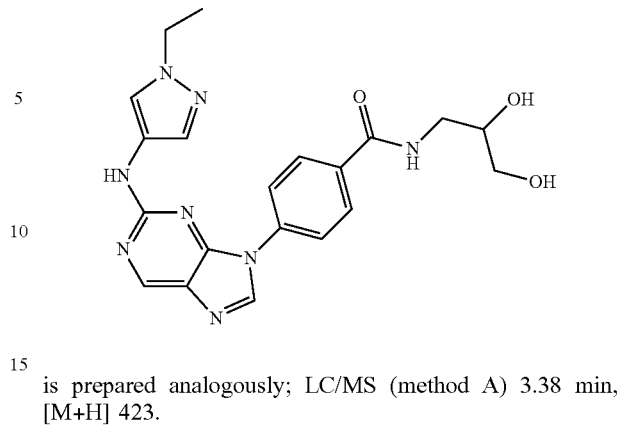
is prepared analogously; LC/MS (method A) 3.38 min, [M+H] 423.
EXAMPLE 22
Synthesis of (1-methyl-1H-pyrazol-4-yl)-{9-[4-(1-piperidin-4-yl-1H-pyrazol-4-yl)-phenyl]-9H-purin-2-yl}-amine ("A23")
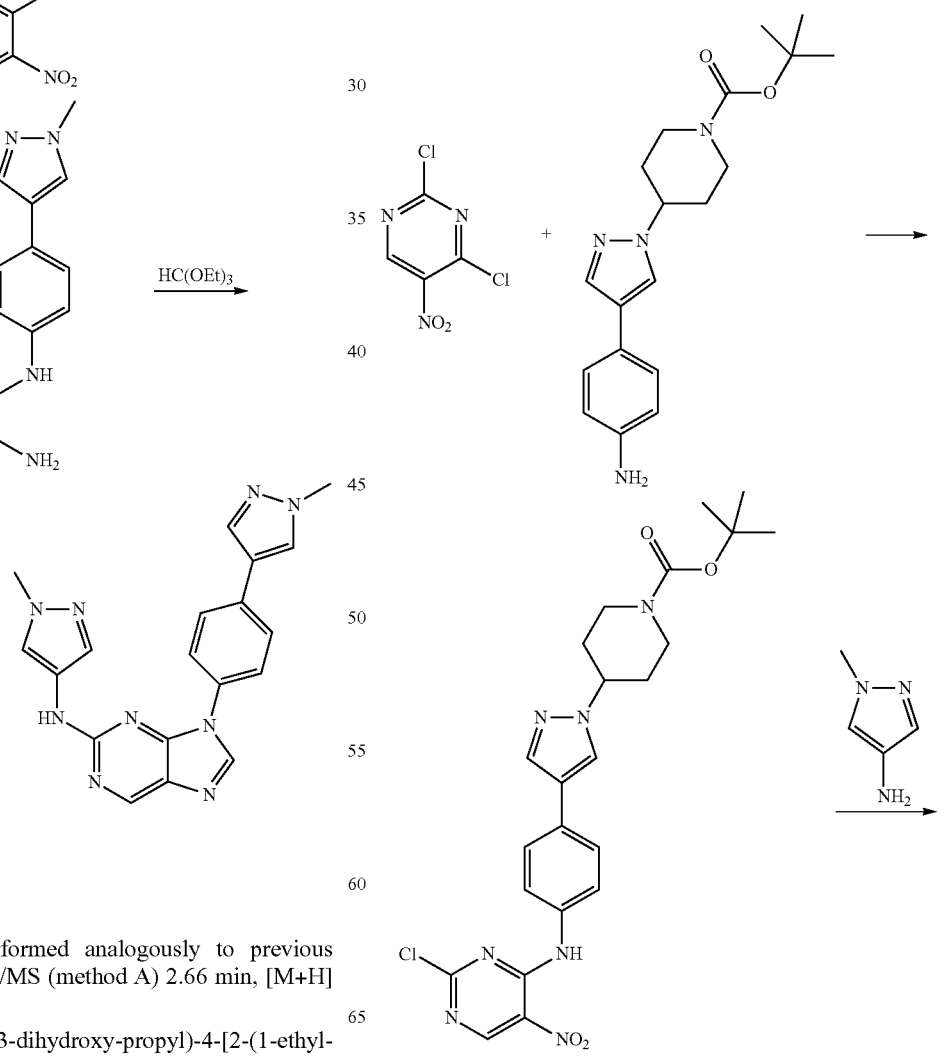

107
-continued

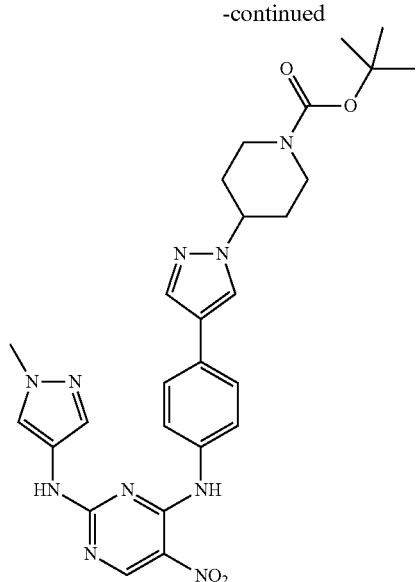

108
-continued

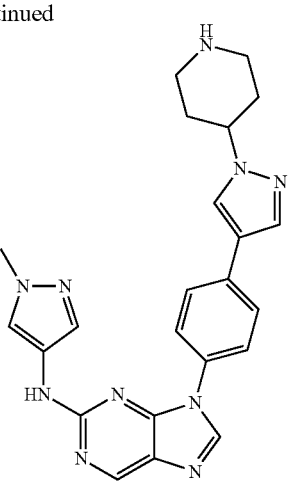

The synthesis is performed analogously to previous examples (1, 2, 3, 4, 5); "A23" trifluoracetate: LC/MS (method A) 2.25 min, [M+H] 441.

EXAMPLE 23

Synthesis of N2-(1-methyl-1H-pyrazol-4-yl)-9-[4-(1-methyl-1H-pyrazol-4-yl)-phenyl]-9H-purine-2,8-diamine ("A24")

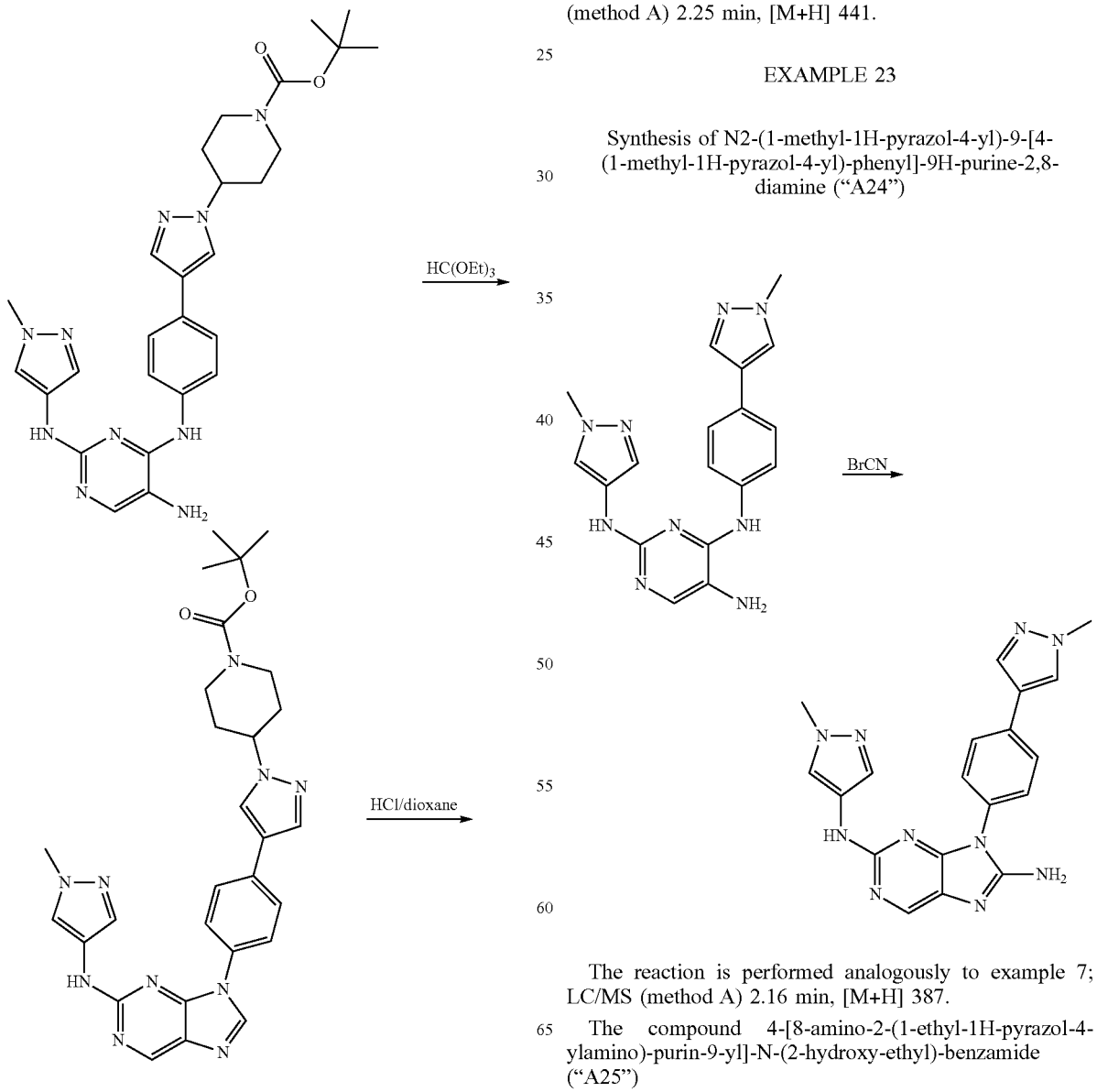

The reaction is performed analogously to example 7; LC/MS (method A) 2.16 min, [M+H] 387.

The compound 4-[8-amino-2-(1-ethyl-1H-pyrazol-4-ylamino)-purin-9-yl]-N-(2-hydroxy-ethyl)-benzamide ("A25")

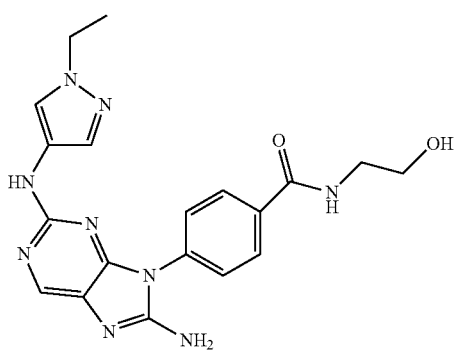 [SMILES: CCn1cc(Nc2ncc3nc(N)n(-c4ccc(C(=O)NCCO)cc4)c3n2)cn1]
is prepared analogously; LC/MS (method A) 2.87 min, [M+H] 458.
EXAMPLE 24
Synthesis of N2-(1-methyl-1H-pyrazol-4-yl)-9-[4-(1-piperidin-4-yl-1H-pyrazol-4-yl)-phenyl]-9H-purine-2,8-diamine ("A26")
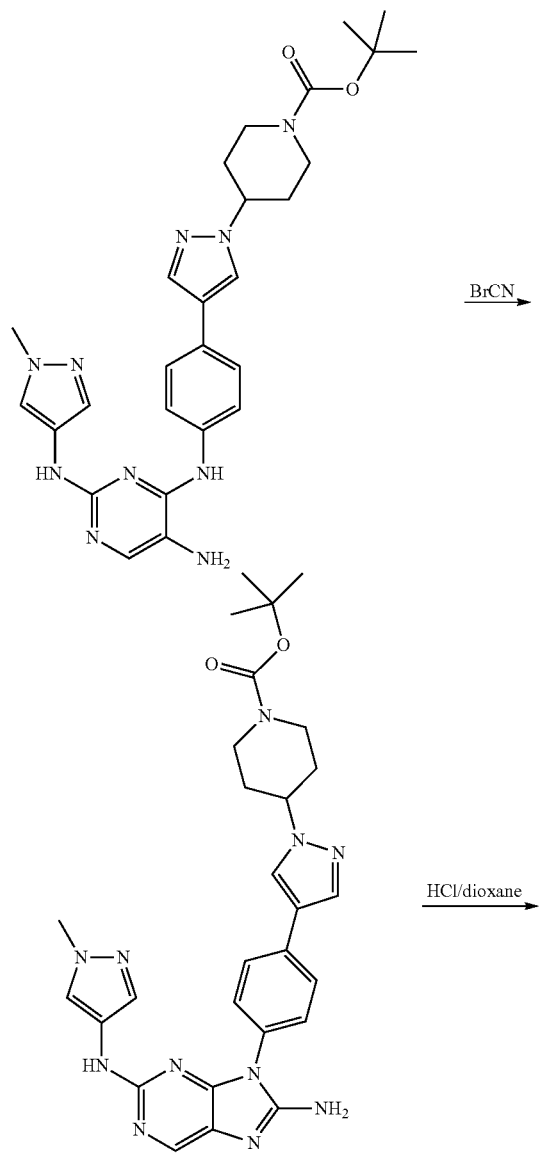
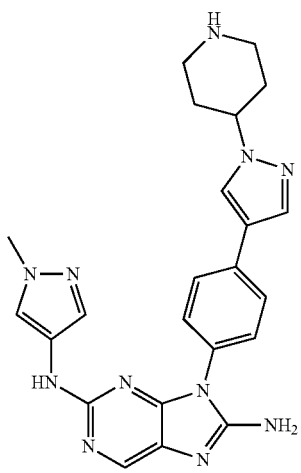
The reaction is performed analogously to example 7; LC/MS (method A) 1.83 min, [M+H] 456.
EXAMPLE 25
Synthesis of (trans)-3-[9-(3-fluoro-4-iodo-phenyl)-9H-purin-2-ylamino]-cyclopentanol ("A27")
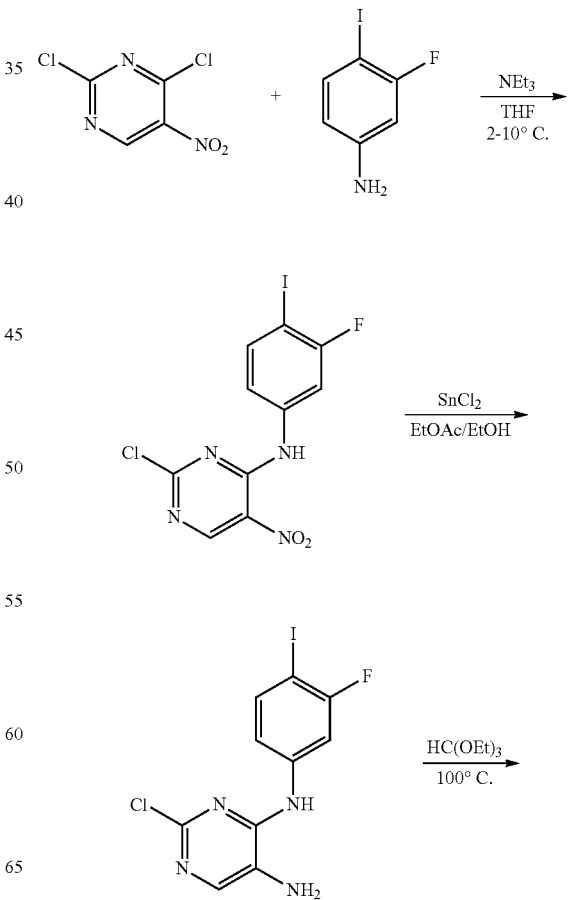

-continued

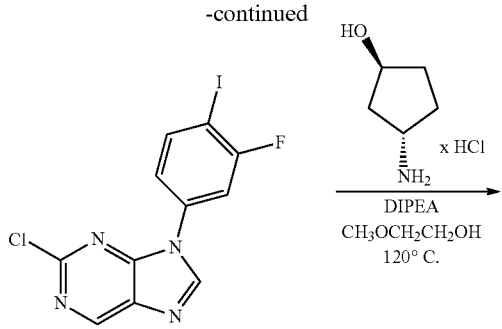

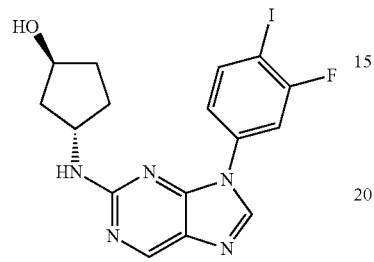

To a stirred solution of 2,4-dichloro-5-nitro-pyrimidine (7.56 g, 39.0 mmol) in THF (150 ml) is added a solution of 3-fluoro-4-iodo-aniline (9.24 g, 39.0 mmol) in THF (150 ml) dropwise and under external cooling with ice. Then, still under cooling, triethylamine (5.40 ml, 39.0 mmol) is added slowly. The reaction mixture is stirred for 30 minutes at 2-10° C. and then it is allowed to reach room temperature. The solids are filtered off and washed with THF. The filtrate is evaporated and triturated with water. The solids are filtered off, washed with water and dried under vacuum to afford (2-chloro-5-nitro-pyrimidin-4-yl)-(3-fluoro-4-iodo-phenyl)-amine; HPLC/MS 3.13 min (C), [M+H] 395.

To a solution of (2-chloro-5-nitro-pyrimidin-4-yl)-(3-fluoro-4-iodo-phenyl)-amine (15.33 g, 38.9 mmol) in a mixture of ethyl acetate (200 ml) and ethanol (50 ml) is added tin(II)chloride (11.1 g, 58.3 mmol) and the reaction mixture is stirred for 90 minutes at 70° C. The reaction mixture is cooled to room temperature, basified with saturated sodium carbonate solution, filtered over a pad of Celite and the residue is washed with ethyl acetate. The organic phase of the filtrate is separated, dried over sodium sulfate and evaporated. The residue is chromatographed on a silica gel column with cyclohexane/ethyl acetate as eluent to afford 2-chloro-N4-(3-fluoro-4-iodo-phenyl)-pyrimidine-4,5-diamine as orange solid; HPLC/MS 2.78 min (C), [M+H] 365.

A solution of 2-chloro-N4-(3-fluoro-4-iodo-phenyl)-pyrimidine-4,5-diamine (2.60 g, 7.13 mmol) in triethyl orthoformate (70 ml) is heated to 100° C. and stirred at this temperature for 18 hours. The reaction mixture is evaporated in vacuo and the residue is crystallized from ethyl acetate to afford 2-chloro-9-(3-fluoro-4-iodo-phenyl)-9H-purine as beige crystals; HPLC/MS 2.77 min (C), [M+H] 375. $^1$H NMR (500 MHz, DMSO-d6) δ 9.23 (s, 1H), 9.09 (s, 1H), 8.15 (dd, J=8.5, 7.1 Hz, 1H), 7.93 (dd, J=9.2, 2.4 Hz, 1H), 7.65 (ddd, J=8.5, 2.4, 0.6 Hz, 1H).

To a solution of 2-chloro-9-(3-fluoro-4-iodo-phenyl)-9H-purine (1.16 g, 3.08 mmol) in 2-methoxyethanol (40 ml) are added trans-3-amino-cyclopentanol hydrochloride (466 mg, 3.30 mmol) and N-ethyldiisopropylamine (1.05 ml, 6.17 mmol). The mixture is heated to 120° C. and stirred at this temperature for 30 hours. The reaction mixture is cooled to room temperature and evaporated. The residue is chromatographed on a silica gel column with ethyl acetate/methanol as eluent to afford trans-3-[9-(3-fluoro-4-iodo-phenyl)-9H-purin-2-ylamino]-cyclopentanol as beige solid; HPLC/MS 2.33 min (C), [M+H] 440; $^1$H NMR (400 MHz, DMSO-d$_6$) δ [ppm] 8.72 (s, 1H), 8.59 (s, 1H), 8.08 (dd, J=9.8, 2.4 Hz, 1H), 8.04 (dd, J=8.5, 7.2 Hz, 1H), 7.75 (d, J=8.3 Hz, 1H), 7.29 (bs, 1H), 4.45 (d, J=3.8 Hz, 1H), 4.36 (bs, 1H), 4.21 (dq, J=6.1, 3.1 Hz, 1H), 2.19-2.04 (m, 1H), 1.90 (m, 2H), 1.71 (dt, J=13.3, 6.6 Hz, 1H), 1.49 (m, 2H).

The compound (trans)-3-[9-(4-ethoxy-phenyl)-9H-purin-2-ylamino]-cyclopentanol ("A28")

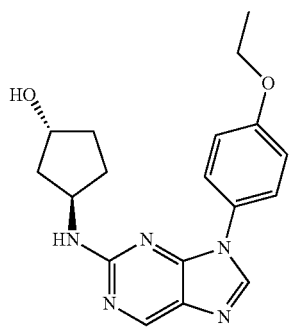 [SMILES: CCOc1ccc(-n2cnc3cnc(N[C@@H]4CC[C@@H](O)C4)nc32)cc1]

is prepared analogously; HPLC/MS 2.07 min (B), [M+H] 340.

EXAMPLE 26

Synthesis of (trans)-3-(9-{3-fluoro-4-[1-(2-methoxy-ethyl)-1H-pyrazol-4-yl]-phenyl}-9H-purin-2-ylamino)-cyclopentanol ("A29")

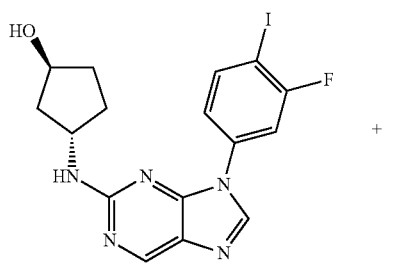

+

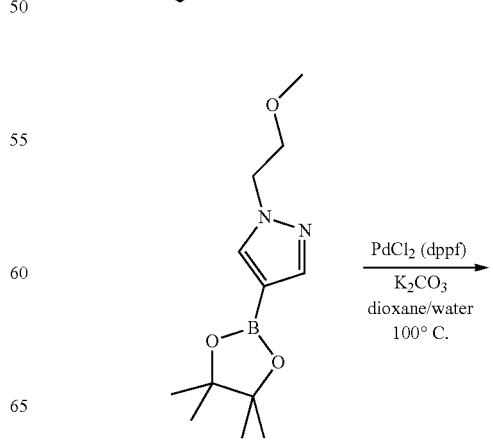

-continued

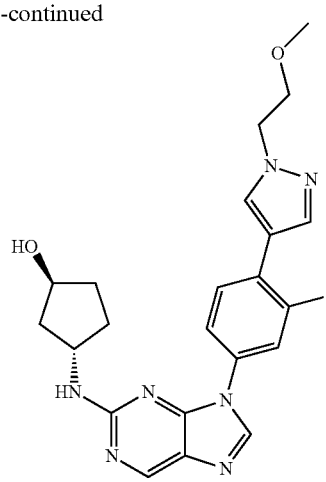

To a solution of trans-3-[9-(3-fluoro-4-iodo-phenyl)-9H-purin-2-ylamino]-cyclopentanol (176 mg, 0.40 mmol), 1-(2-methoxy-ethyl)-4-(4,4,5,5-tetramethyl-[1,3,2]dioxaborolan-2-yl)-1H-pyrazole (131 mg, 0.52 mmol) in dioxane (7 ml) are added water (0.7 ml) and potassium carbonate (166 mg, 1.20 mmol). The mixture is flushed with nitrogen and heated to 80° C. Dichloro[1,1'-bis(di-phenylphosphino)ferrocene]palladium(II) dichloromethane adduct (33 mg, 0.04 mmol) is added and the mixture is stirred in a closed reaction vial for two hours at 100° C. The reaction mixture is allowed to reach room temperature and evaporated. The residue is chromatographed on a silica gel column with dichloromethane/methanol as eluent to afford trans-3-(9-{3-fluoro-4-[1-(2-methoxy-ethyl)-1H-pyrazol-4-yl]-phenyl}-9H-purin-2-ylamino)-cyclopentanol as beige powder; HPLC/MS 2.06 min (C), [M+H] 438; $^1$H NMR (500 MHz, DMSO-$d_6$, TFA-$d_1$): δ [ppm] 9.12 (s, 1H), 9.06 (s, 1H), 8.26 (s, 1H), 8.05 (s, 1H), 8.01 (t, J=8.5 Hz, 1H), 7.95 (d, J=12.2 Hz, 1H), 7.83 (d, J=8.5 Hz, 1H), 4.43 (p, J=7.4 Hz, 1H), 4.37 (t, J=5.3 Hz, 2H), 4.30 (dp, J=5.9, 2.9 Hz, 1H), 3.77 (t, J=5.3 Hz, 2H), 3.29 (s, 3H), 2.33-2.20 (m, 1H), 2.04 (ddd, J=13.5, 7.6, 3.0 Hz, 1H), 2.01-1.92 (m, 1H), 1.83 (ddd, J=13.2, 7.2, 5.9 Hz, 1H), 1.68-1.51 (m, 2H).

The compound (trans)-3-{9-[4-(1-Methyl-1H-pyrazol-4-yl)-phenyl]-9H-purin-2-ylamino}-cyclopentanol ("A30")

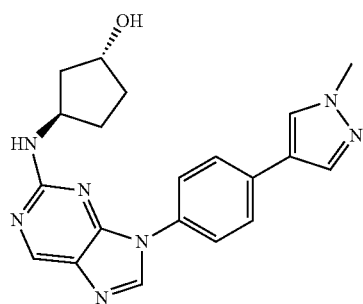 [SMILES: Cn1cc(-c2ccc(-n3cnc4cnc(N[C@@H]5CC[C@@H](O)C5)nc43)cc2)cn1]

is prepared analogously; HPLC/MS 1.66 min (A), [M+H] 376.

EXAMPLE 27

Synthesis of (1R,3R)-3-[9-(3-fluoro-4-iodo-phenyl)-9H-purin-2-ylamino]-cyclopentanecarboxylic acid amide ("A31")

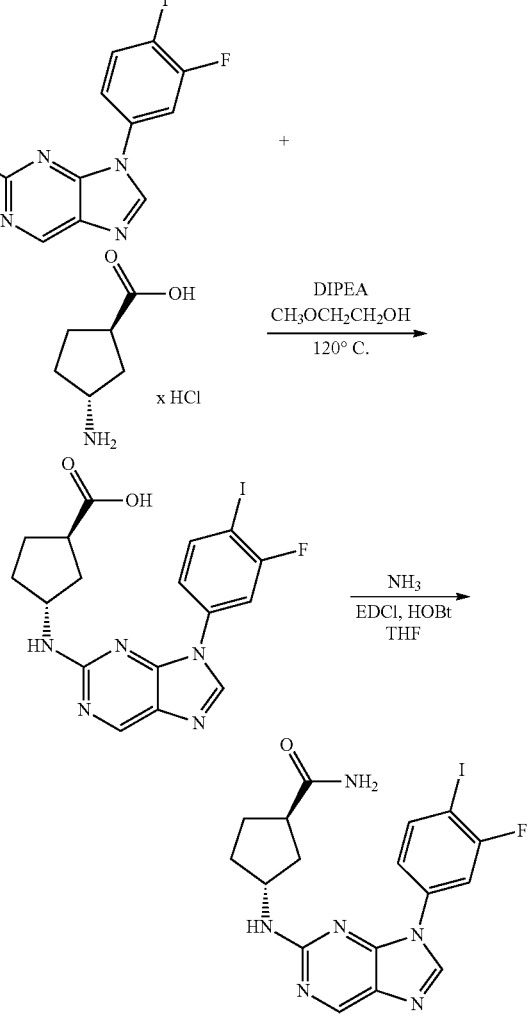

To a solution of 2-chloro-9-(3-fluoro-4-iodo-phenyl)-9H-purine (1.12 g, 3.00 mmol) in 2-methoxyethanol (40 ml) are added (1R,3R)-3-amino-cyclopentanecarboxylic acid hydrochloride (488 mg, 3.00 mmol) and N-ethyldiisopropylamine (1.07 ml, 6.3 mmol). The mixture is heated to 120° C. and stirred at this temperature for 40 hours. The reaction mixture is cooled to room temperature and evaporated. The residue is chromatographed on a silica gel column with ethyl acetate/methanol as eluent to afford (1R,3R)-3-[9-(3-fluoro-4-iodo-phenyl)-9H-purin-2-ylamino]-cyclopentanecarboxylic acid as dark brown solid; HPLC/MS 2.45 min (C), [M+H] 468.

To a solution of (1R,3R)-3-[9-(3-fluoro-4-iodo-phenyl)-9H-purin-2-ylamino]-cyclopentanecarboxylic acid (406 mg, 0.87 mmol) in THF (10 ml) are added N-(3-dimethylaminopropyl)-N'-ethylcarbodiimide hydrochloride (334 mg, 1.74 mmol), 1-hydroxybenzotriazole hydrate (235 mg, 1.74 mmol) and ammonia as a 0.5 M solution in dioxane (8.9 ml, 4.4 mmol). The reaction mixture is stirred for 16 hours at room temperature. It is then evaporated and partitioned between ethyl acetate and saturated sodium hydrogen carbonate solution. The organic phase is dried over sodium sulfate and evaporated. The residue is chromatographed on a silica gel column with dichloromethane/methanol as eluent to afford (1R,3R)-3-[9-(3-fluoro-4-iodo-phenyl)-9H-purin-2-ylamino]-cyclopentanecarboxylic acid amide as brown powder; HPLC/MS 2.25 min (C), [M+H] 467; ¹H NMR (400 MHz, DMSO-d$_6$) δ [ppm] 8.74 (s, 1H), 8.62 (s, 1H), 8.08 (dd, J=9.8, 2.4 Hz, 1H), 8.04 (dd, J=8.6, 7.2 Hz, 1H), 7.79 (d, J=5.6 Hz, 1H), 7.34 (s, 1H), 7.21 (s, 1H), 6.68 (s, 1H), 4.26 (s, 1H), 2.77 (p, J=8.0 Hz, 1H), 2.04 (m, 2H), 1.92 (td, J=8.3, 4.5 Hz, 1H), 1.78 (ddd, J=13.4, 8.7, 5.3 Hz, 1H), 1.73-1.53 (m, 2H).

The following compounds are prepared analogously:

(1R,3R)-3-[9-(4-ethoxy-phenyl)-9H-purin-2-ylamino]-cyclopentanecarboxylic acid amide ("A32")

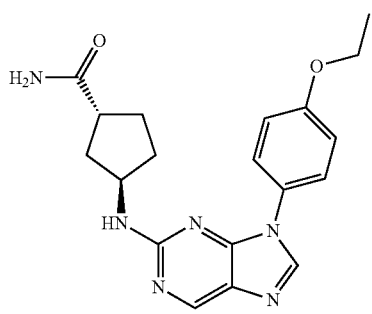 [SMILES: CCOc1ccc(-n2cnc3cnc(N[C@@H]4CC[C@@H](C(N)=O)C4)nc32)cc1]

HPLC/MS 1.55 min (A), [M+H] 385;

(1R,3R)-3-[9-(4-iodo-phenyl)-9H-purin-2-ylamino]-cyclopentanecarboxylic acid amide ("A33")

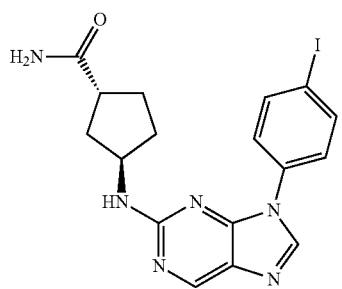 [SMILES: NC(=O)[C@@H]1CC[C@@H](Nc2ncc3ncn(-c4ccc(I)cc4)c3n2)C1]

HPLC/MS 1.62 min (A), [M+H] 449;

(1R,3R)-3-{9-[4-(2-methoxy-ethoxy)-phenyl]-9H-purin-2-ylamino}-cyclopentanecarboxylic acid amide ("A34")

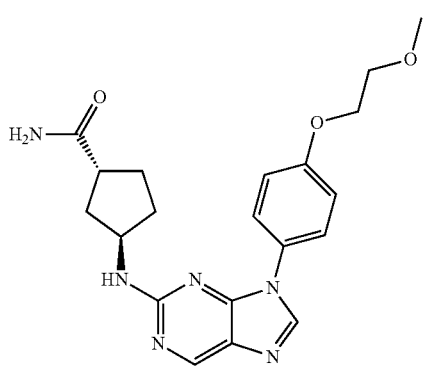 [SMILES: COCCOc1ccc(-n2cnc3cnc(N[C@@H]4CC[C@@H](C(N)=O)C4)nc32)cc1]

HPLC/MS 1.45 min (A), [M+H] 397.

EXAMPLE 28

Synthesis of (1R,3R)-3-(9-{3-fluoro-4-[1-(2-methoxy-ethyl)-1H-pyrazol-4-yl]-phenyl}-9H-purin-2-ylamino)-cyclopentanecarboxylic acid amide ("A35")

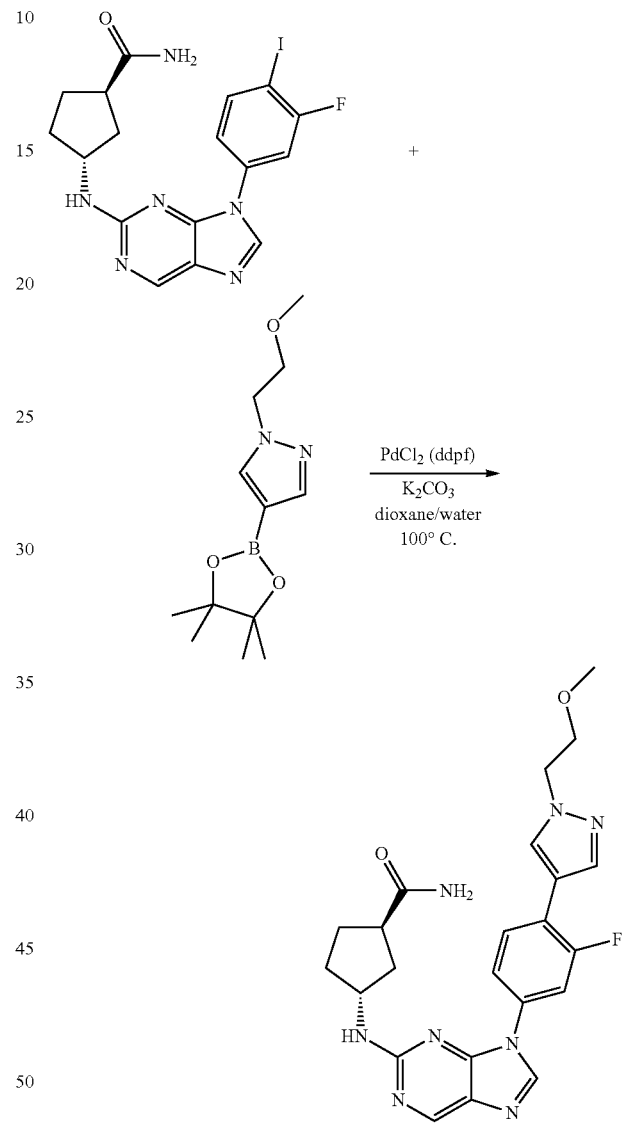

To a solution of (1R,3R)-3-[9-(3-fluoro-4-iodo-phenyl)-9H-purin-2-ylamino]-cyclopentanecarboxylic acid amide (117 mg, 0.25 mmol), 1-(2-methoxy-ethyl)-4-(4,4,5,5-tetramethyl-[1,3,2]dioxaborolan-2-yl)-1H-pyrazole (80.7 mg, 0.32 mmol) in dioxane (5 ml) are added water (0.5 ml) and potassium carbonate (103 mg, 0.74 mmol). The mixture is flushed with nitrogen and heated to 80° C. Dichloro[1,1'-bis(diphenylphosphino)ferrocene]palladium(II) dichloromethane adduct (20 mg, 0.02 mmol) is added and the mixture is stirred in a closed reaction vial for three hours at 100° C. The reaction mixture is allowed to reach room temperature and evaporated. The residue is chromatographed on a silica gel column with dichloromethane/methanol as eluent to afford (1R,3R)-3-(9-{3-fluoro-4-[1-(2- methoxy-ethyl)-1H-pyrazol-4-yl]-phenyl}-9H-purin-2-ylamino)-cyclopentanecarboxylic acid amide as brown powder; HPLC/MS 2.01 min (C), [M+H] 465; ¹H NMR (500 MHz, DMSO-d₆) δ [ppm] 8.74 (s, 1H), 8.62 (s, 1H), 8.22 (d, J=1.9 Hz, 1H), 8.05 (d, J=12.7 Hz, 1H), 8.00 (s, 1H), 7.91 (m, 2H), 7.31 (s, 1H), 7.21 (s, 1H), 6.66 (s, 1H), 4.33 (t, J=5.4 Hz, 2H), 4.28 (s, 1H), 3.74 (t, J=5.3 Hz, 2H), 3.26 (s, 3H), 2.78 (p, J=8.0 Hz, 1H), 2.04 (m, 2H), 1.93 (dtd, J=11.9, 7.8, 4.5 Hz, 1H), 1.87-1.77 (m, 1H), 1.73-1.56 (m, 2H).

The following compound is prepared analogously:
(1R,3R)-3-(9-{4-[1-(2-ethoxy-ethyl)-1H-pyrazol-4-yl]-phenyl}-9H-purin-2-ylamino)-cyclopentanecarboxylic acid amide ("A36")

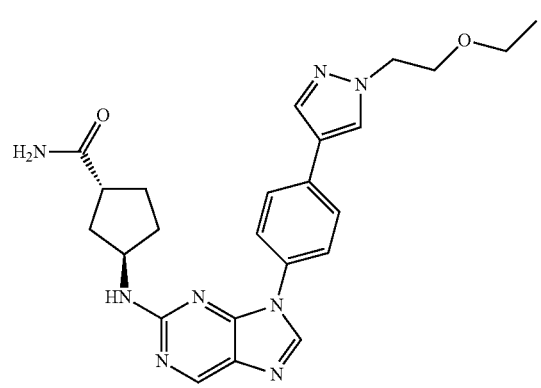 [SMILES: CCOCCn1cc(-c2ccc(-n3cnc4cnc(N[C@@H]5CC[C@@H](C(N)=O)C5)nc43)cc2)cn1]

HPLC/MS 1.55 min (A), [M+H] 461.

EXAMPLE 29

Synthesis of (1R,3R)-3-[9-(2-methyl-quinolin-6-yl)-9H-purin-2-ylamino]-cyclopentanecarboxylic acid amide ("A37")

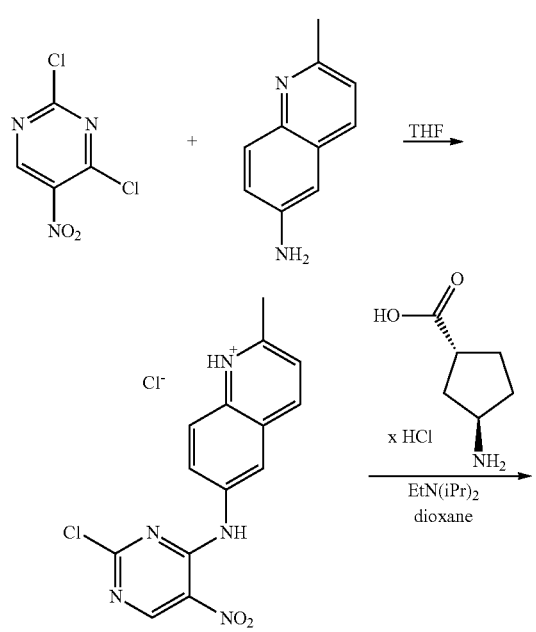

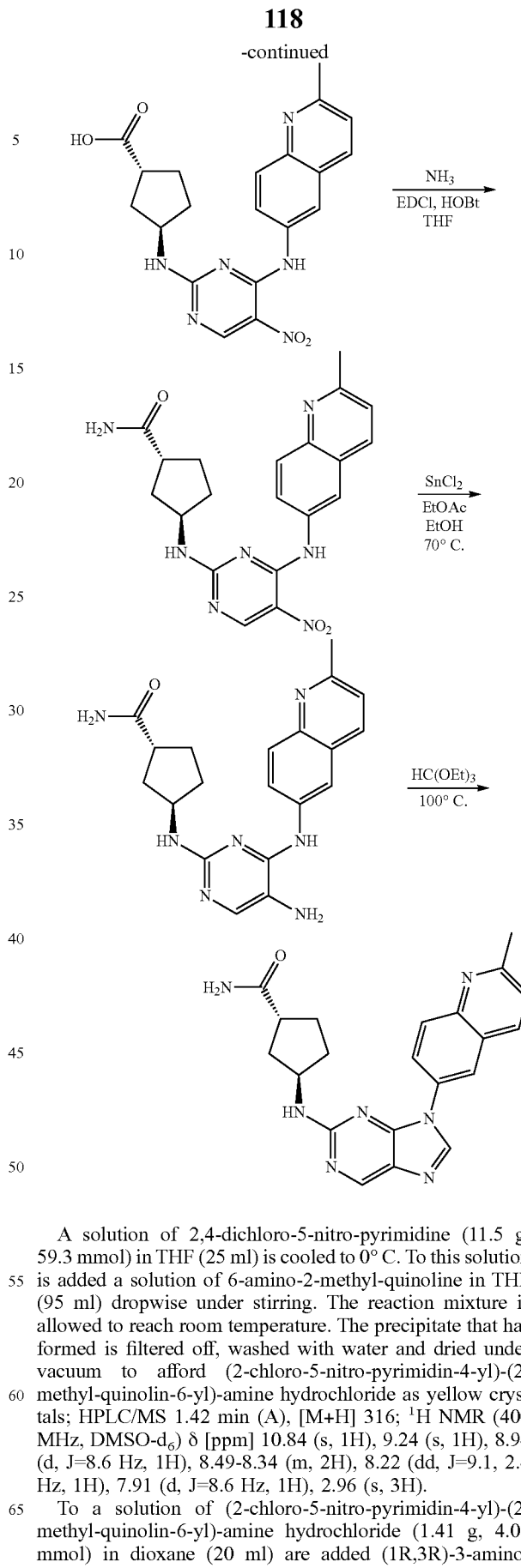

A solution of 2,4-dichloro-5-nitro-pyrimidine (11.5 g, 59.3 mmol) in THF (25 ml) is cooled to 0° C. To this solution is added a solution of 6-amino-2-methyl-quinoline in THF (95 ml) dropwise under stirring. The reaction mixture is allowed to reach room temperature. The precipitate that has formed is filtered off, washed with water and dried under vacuum to afford (2-chloro-5-nitro-pyrimidin-4-yl)-(2-methyl-quinolin-6-yl)-amine hydrochloride as yellow crystals; HPLC/MS 1.42 min (A), [M+H] 316; ¹H NMR (400 MHz, DMSO-d₆) δ [ppm] 10.84 (s, 1H), 9.24 (s, 1H), 8.94 (d, J=8.6 Hz, 1H), 8.49-8.34 (m, 2H), 8.22 (dd, J=9.1, 2.4 Hz, 1H), 7.91 (d, J=8.6 Hz, 1H), 2.96 (s, 3H).

To a solution of (2-chloro-5-nitro-pyrimidin-4-yl)-(2-methyl-quinolin-6-yl)-amine hydrochloride (1.41 g, 4.01 mmol) in dioxane (20 ml) are added (1R,3R)-3-aminocyclopentanecarboxylic acid hydrochloride (700 mg, 4.23 mmol) and N-ethyldiisopropylamine (2.0 ml, 11.8 mmol) and the mixture is stirred for 18 hours at ambient temperature. The reaction mixture is evaporated and the residue is chromatographed on a silica gel column with dichloromethane/methanol as eluent to afford (1R,3R)-3-[4-(2-methyl-quinolin-6-ylamino)-5-nitro-pyrimidin-2-ylamino]-cyclopentanecarboxylic acid as yellow solid; HPLC/MS 1.52 min (A), [M+H] 409; $^1$H NMR (400 MHz, DMSO-$d_6$) δ [ppm] 10.84 (s, 1H), 9.24 (s, 1H), 8.94 (d, J=8.6 Hz, 1H), 8.49-8.34 (m, 2H), 8.22 (dd, J=9.1, 2.4 Hz, 1H), 7.91 (d, J=8.6 Hz, 1H), 2.96 (s, 3H).

To a suspension of (1R,3R)-3-[4-(2-methyl-quinolin-6-ylamino)-5-nitro-pyrimidin-2-ylamino]-cyclopentanecarboxylic acid (355 mg, 0.87 mmol) in THF (9 ml) are added N-(3-dimethylaminopropyl)-N'-ethylcarbodiimide hydrochloride (332 mg, 1.73 mmol), 1-hydroxybenzotriazole hydrate (117 mg, 0.87 mmol) and ammonia as a 0.5M solution in dioxane (9.0 ml, 4.5 mmol). The reaction mixture is stirred for 16 hours at room temperature. It is then evaporated and the residue is chromatographed on a silica gel column with dichloromethane/methanol as eluent to afford (1R,3R)-3-[4-(2-methyl-quinolin-6-ylamino)-5-nitro-pyrimidin-2-ylamino]-cyclopentanecarboxylic acid amide as yellow solid; HPLC/MS 1.39 min (A), [M+H] 408.

To a suspension of (1R,3R)-3-[4-(2-methyl-quinolin-6-ylamino)-5-nitro-pyrimidin-2-ylamino]-cyclopentanecarboxylic acid amide (399 mg, 0.98 mmol) in a mixture of ethyl acetate (4.5 ml) and ethanol (1.5 ml) is added tin(II)-chloride (555 mg, 2.93 mmol) and the reaction mixture is stirred for 16 hours at 70° C. The reaction mixture is cooled to room temperature, basified with saturated sodium carbonate solution, filtered over a pad of Celite and the residue is washed with ethyl acetate and water. The organic phase of the filtrate is separated, dried over sodium sulfate and evaporated to afford (1R,3R)-3-[5-amino-4-(2-methyl-quinolin-6-ylamino)-pyrimidin-2-ylamino]-cyclopentanecarboxylic acid amide as orange brown solid; HPLC/MS 1.15 min (A), [M+H] 378.

A solution of (1R,3R)-3-[5-amino-4-(2-methyl-quinolin-6-ylamino)-pyrimidin-2-ylamino]-cyclopentanecarboxylic acid amide (109 mg, 0.29 mmol) in triethyl orthoformate (3 ml) is heated to 100° C. and stirred at this temperature for 16 hours. The reaction mixture is evaporated in vacuo and the residue is chromatographed on a silica gel column with dichloromethane/methanol as beige solid; HPLC/MS 1.29 min (A), [M+H] 388; $^1$H NMR (400 MHz, DMSO-$d_6$) δ [ppm] 8.77 (s, 1H), 8.66 (s, 1H), 8.56 (s, 1H), 8.34 (d, J=8.5 Hz, 1H), 8.30 (s, 1H), 8.11 (d, J=9.0 Hz, 1H), 7.53 (d, J=8.5 Hz, 1H), 7.25 (m, 2H), 6.68 (s, 1H), 4.30 (bs, 1H), 2.79 (p, J=8.2 Hz, 1H), 2.70 (s, 3H), 2.18-1.99 (m, 2H), 1.98-1.87 (m, 1H), 1.86-1.75 (m, 1H), 1.74-1.56 (m, 2H).

EXAMPLE 30

Synthesis of (9-{4-[1-(2-methoxy-ethyl)-1H-pyrazol-4-yl]-phenyl}-9H-purin-2-yl)-(R)-pyrrolidin-3-yl-amine ("A38") and 1-[(R)-3-(9-{4-[1-(2-methoxy-ethyl)-1H-pyrazol-4-yl]-phenyl}-9H-purin-2-ylamino)-pyrrolidin-1-yl]-3-(4-methyl-piperazin-1-yl)-propan-1-one ("A39")

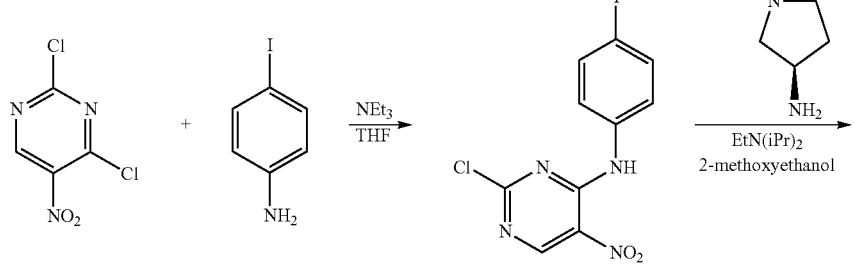

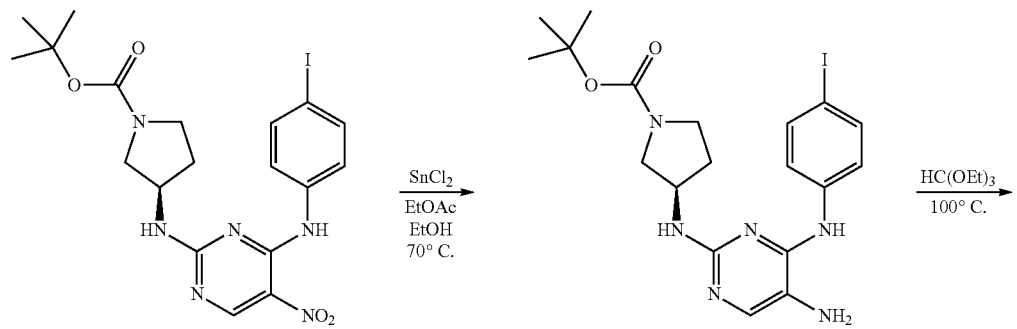

-continued
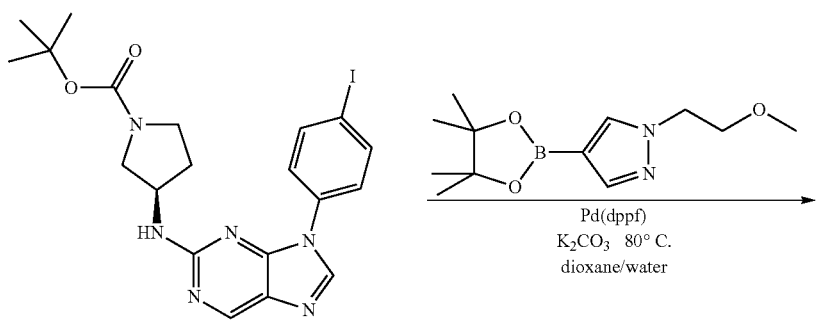
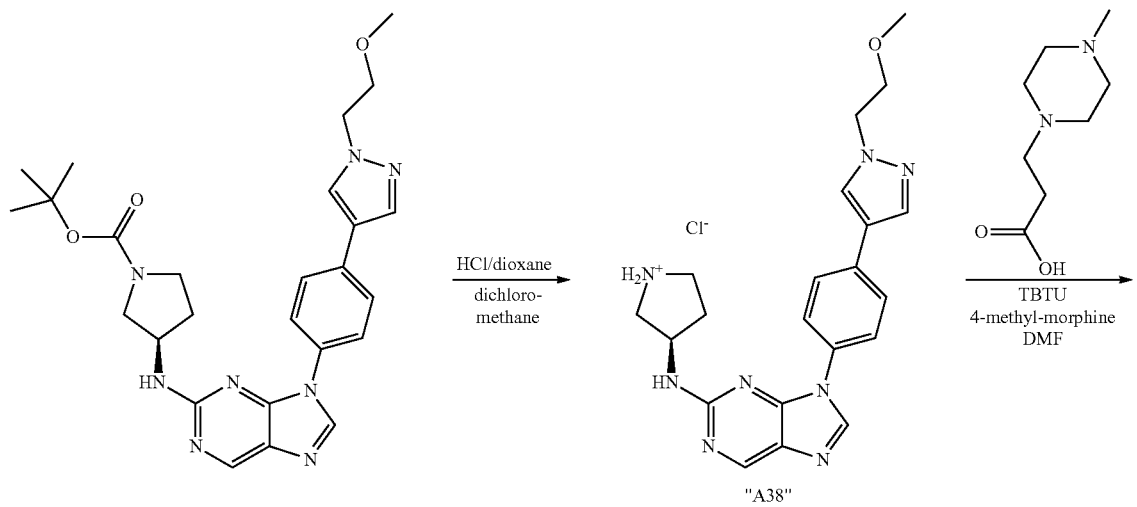
"A38"
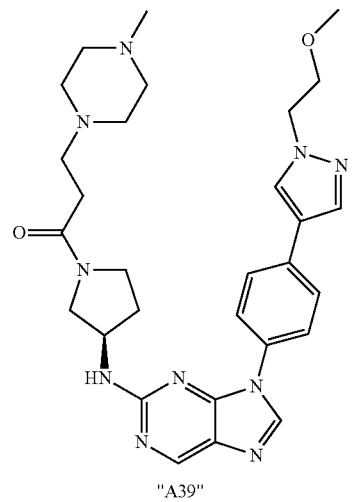 [SMILES: COCCn1cc(-c2ccc(-n3cnc4cnc(N[C@@H]5CCN(C(=O)CCN6CCN(C)CC6)C5)nc43)cc2)cn1]
"A39"

"A38": grey solid; HPLC/MS 1.33 min (A), [M+H] 405;
"A39": colourless amorphous solid; HPLC/MS 1.34 min (A), [M+H] 559.

EXAMPLE 31

Synthesis of (1R,3R)-3-[9-(4-ethoxy-phenyl)-8-methyl-9H-purin-2-ylamino]-cyclobentanecarboxylic acid amide ("A40")

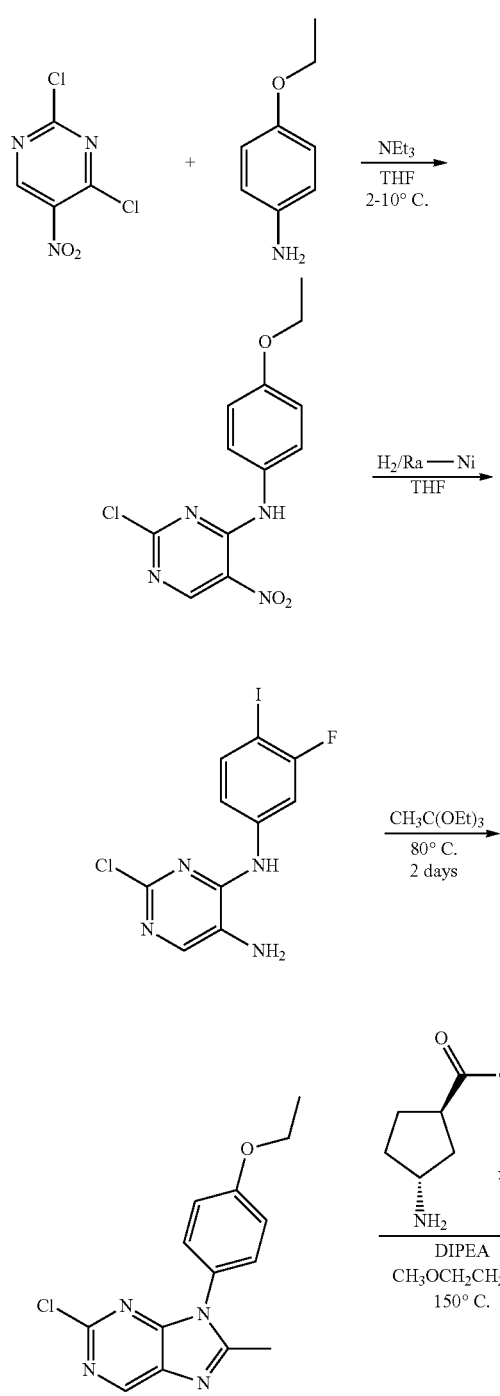

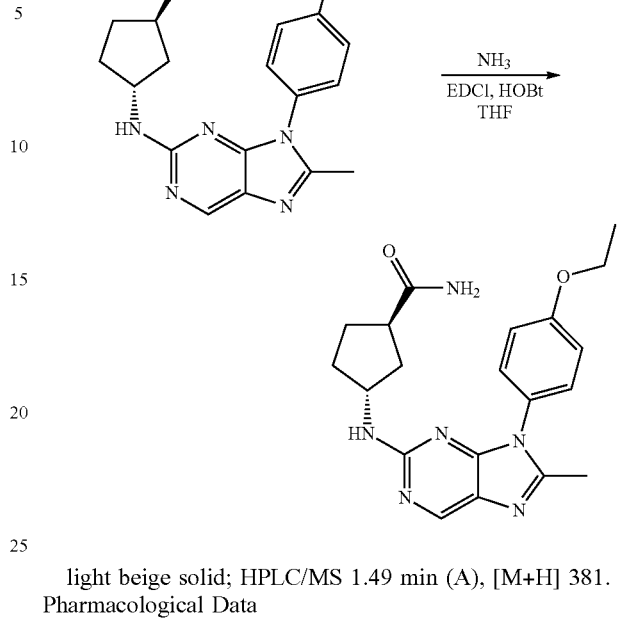

light beige solid; HPLC/MS 1.49 min (A), [M+H] 381.

Pharmacological Data

TABLE 2

GCN2 inhibition of some representative compounds of the formula I

| Compound No. | IC$_{50}$ GCN2 (enzyme assay) | IC$_{50}$ GCN2 (cellular assay) | Compound No. | IC$_{50}$ GCN2 (enzyme assay) | IC$_{50}$ GCN2 (cellular assay) |
| --- | --- | --- | --- | --- | --- |
| "A1" | A | | "A11" | A | |
| "A2" | A | | "A12" | A | |
| "A3" | A | | "A13" | A | |
| "A4" | A | | "A14" | C | |
| "A5" | A | | "A15" | B | |
| "A6" | B | | "A16" | A | |
| "A7" | A | | "A17" | A | |
| "A8" | C | | "A18" | A | |
| "A9" | A | | "A19" | B | |
| "A10" | A | | "A20" | C | |
| "A21" | A | | "A31" | B | |
| "A22" | B | | "A32" | B | |
| "A23" | A | | "A33" | B | |
| "A24" | B | | "A34" | B | |
| "A25" | C | | "A35" | A | |
| "A26" | B | | "A36" | A | |
| "A27" | C | | "A37" | A | |
| "A28" | | | "A38" | C | |
| "A29" | B | | "A39" | B | |
| "A30" | B | | "A40" | | |

IC$_{50}$:
<1 µM = A
1-5 µM = B
5-10 µM = C

The compounds shown in Table 2 are particularly preferred compounds according to the invention.

The following examples relate to medicaments:

EXAMPLE A

Injection vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of the formula I

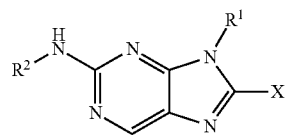

I in which
X denotes H, $CH_3$ or $NH_2$,
$R^1$ denotes Ar or Het,
$R^2$ denotes pyrazolyl, pyrrolidinyl or cyclopentyl, each of which is unsubstituted or monosubstituted by A, Hal, $[C(R^3)_2]_pOR^3$, $O[C(R^3)_2]_pOR^3$, $[C(R^3)_2]_pN(R^3)_2$, $[C(R^3)_2]_pAr$, $[C(R^3)_2]_pHet^1$, CN, $[C(R^3)_2]_pCOOR^3$, Cyc, $CO[C(R^3)_2]_pN(R^3)_2$, $CO[C(R^3)_2]_pHet^1$, $NR^3COA$, $NR^3SO_2A$, $SO_2N(R^3)_2$, $S(O)_nA$, $COHet^1$, $O[C(R^3)_2]_mN(R^3)_2$, $O[C(R^3)_2]_pHet^1$, NHCOOA, $NHCON(R^3)_2$, $NHCOO[C(R^3)_2]_mN(R^3)_2$, NHCOO[C$(R^3)_2]_pHet^1$, $NHCONH[C(R^3)_2]_mN(R^3)_2$, NHCONH[C$(R^3)_2]_pHet^1$, $OCONH[C(R^3)_2]_mN(R^3)_2$, OCONH[C$(R^3)_2]_pHet^1$ or $C(O)R^3$,
$R^3$ denotes H or unbranched alkyl with 1-4 C-atoms or branched alkyl with 3-4 C-atoms,
Ar denotes phenyl, which is unsubstituted or mono-, di- or trisubstituted by Hal, A, $[C(R^3)_2]_pOR^3$, $O[C(R^3)_2]_pOR^3$, $[C(R^3)_2]_pN(R^3)_2$, $O[C(R^3)_2]_pN(R^3)_2$, $[C(R^3)_2]_pHet^1$, $NO_2$, CN, $[C(R^3)_2]_pCOOR^3$, $O[C(R^3)_2]_pCOOR^3$, $CONH_2$, CONA, $CONA_2$, $NR^3COA$, $NR^3SO_2A$, $SO_2N(R^3)_2$, $S(O)_nA$, $COHet^1$, $O[C(R^3)_2]_pHet^1$, NHCOOA, $NHCON(R^3)_2$, NHCOO$[(R^3)_{2m}N(R^3)_2]$, $NHCOO[(R^3)_2]_pHet^1$, NHCONH[C$(R^3)_2]_mN(R^3)_2$, $NHCONH[C(R^3)_2]_pHet^1$, OCONH[C$(R^3)_2]_mN(R^3)_2$, $OCONH[C(R^3)_2]_p\text{-}Het^1$, $S(O)_nHet^1$, CHO and/or COA,
Het denotes furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, pyrazinyl, indolyl, isoindolyl, indolinyl, benz-imidazolyl, indazolyl, quinolyl, isoquinolyl, benzoxazolyl, 1,3-benzodioxolyl, benzothiophenyl, benzofuranyl, imidazopyridyl, dihydroindolyl, quinoxalinyl, benzo[1,2,5]thiadiazolyl or furo[3,2-b]pyridyl, each of which is unsubstituted or mono- or disubstituted by Hal, A, $[C(R^3)_2]_pOR^3$, $O[C(R^3)_2]_pOR^3$, $[C(R^3)_2]_pN(R^3)_2$, $O[C(R^3)_2]_pN(R^3)_2$, $[C(R^3)_2]_pHet^1$, $NO_2$, CN, $[C(R^3)_2]_pCOOR^3$, $O[C(R^3)_2]_pCOOR^3$, $CON(R^3)_2$, $NR^3COA$, $NR^3SO_2A$, $SO_2N(R^3)_2$, $S(O)_nA$, $COHet^1$, $O[C(R^3)_2]_pHet^1$, NHCOOA, $NHCON(R^3)_2$, NHCOO$[C(R^3)_2]_mN(R^3)_2$, $NHCOO[(R^3)_2]_pHet^1$, NHCONH[C$(R^3)_2]_mN(R^3)_2$, $NHCONH[C(R^3)_2]_pHet^1$, OCONH[C$(R^3)_2]_mN(R^3)_2$, $OCONH[C(R^3)_2]_pHet^1$, $S(O)_nHet^1$, CHO, COA, =S and/or =O,
$Het^1$ denotes pyrazolyl, pyridyl, pyrazinyl, indolyl, dihydropyrrolyl, pyrrolidinyl, azetidinyl, oxetanyl, tetrahydroimidazolyl, dihydropyrazolyl, tetrahydropyrazolyl, tetrahydrofuranyl, dihydro-pyridyl, tetrahydropyridyl, piperidinyl, morpholinyl, hexahydro-pyridazinyl, hexahydropyrimidinyl, [1,3]dioxolanyl, tetrahydropyranyl or piperazinyl, each of which is unsubstituted or

127 mono- or disubstituted by Hal, A, [C(R³)₂]ₚOR³, O[C(R³)₂]ₚOR³, [C(R³)₂]ₚ—N(R³)₂, [C(R³)₂]ₚHet², NO₂, CN, [C(R³)₂]ₚCOOR³, O[C(R³)₂]ₚCOOR³, CON(R³)₂, NR³COA, NR³SO₂A, SO₂N(R³)₂, S(O)ₙA, COHet², O[C(R³)₂]ₘN(R³)₂, O[C(R³)₂]ₚHet², NHCOOA, NHCON(R³)₂, NHCOO[C(R³)₂]ₘN(R³)₂, NHCOO[C(R³)₂]ₚHet², NHCONH[C(R³)₂]ₘN(R³)₂, NHCONH[C(R³)₂]ₚHet², OCONH[C(R³)₂]ₘN(R³)₂, OCONH[C(R³)₂]ₚHet², S(O)ₙHet², CHO, COA, =S and/or =O, Het² denotes pyrrolidinyl, azetidinyl, azoxetanyl, tetrahydroimidazolyl, tetrahydropyrazolyl, tetrahydrofuranyl, piperidinyl, morpholinyl, tetrahydropyranyl or piperazinyl, each of which is unsubstituted or mono- or disubstituted by Hal, A, OA, CN, COOA, CONH₂, S(O)ₙA, S(O)ₙAr, COA and/or =O, Cyc denotes cycloalkyl alkyl with 3-7 C-atoms, which is unsubstituted or monosubstituted by NH₂, A denotes unbranched alkyl with 1-6 C-atoms or branched alkyl with 3-6 C-atoms, wherein one or two non-adjacent CH- and/or CH₂-groups may be replaced by N-, O- and/or S-atoms and wherein 1-7 H-atoms may be replaced by F or Cl, Hal denotes F, Cl, Br or I, N denotes 0, 1 or 2, M denotes 1, 2 or 3, P denotes 0, 1, 2, 3 or 4, or a pharmaceutically acceptable alcoholate, hydrate, salt, tautomer or stereoisomer thereof, including mixtures thereof in all ratios.

2. A compound according to claim 1 in which

R² denotes pyrazolyl, pyrrolidinyl or cyclopentyl, each of which is unsubstituted or monosubstituted by A, [C(R³)₂]ₚAr, [C(R³)₂]ₚHet¹, Cyc, [C(R³)₂]ₚOR³, CO[C(R³)₂]ₚN(R³)₂ or CO[C(R³)₂]ₚHet¹, or a pharmaceutically acceptable alcoholate, hydrate, salt, tautomer or stereoisomer thereof, including mixtures thereof in all ratios.

3. A compound according to claim 1 in which

Ar denotes phenyl, which is unsubstituted or mono-, di- or trisubstituted by Hal, A, [C(R³)₂]ₚOR³, O[C(R³)₂]ₚOR³, [C(R³)₂]ₚHet¹, CONH₂, CONA and/or CONA₂, or a pharmaceutically acceptable alcoholate, hydrate, salt, tautomer or stereoisomer thereof, including mixtures thereof in all ratios.

4. A compound according to claim 1 in which

Het denotes pyrazolyl, pyridyl, indolyl, isoindolyl, indolinyl, quinolyl or isoquinolyl, each of which is unsubstituted or mono- or disubstituted by A and/or =O, or a pharmaceutically acceptable alcoholate, hydrate, salt, tautomer or stereoisomer thereof, including mixtures thereof in all ratios.

5. A compound according to claim 1 in which

Het¹ denotes pyrazolyl, pyridyl, pyrrolidinyl, piperidinyl, morpholinyl, tetrahydropyranyl or piperazinyl, each of which is unsubstituted or mono- or disubstituted by A and/or [C(R³)₂]ₚHet², or a pharmaceutically acceptable alcoholate, hydrate, salt, tautomer or stereoisomer thereof, including mixtures thereof in all ratios.

6. A compound according to claim 1 in which

X denotes H, CH₃ or NH₂,

R¹ denotes Ar or Het,

R² denotes pyrazolyl, pyrrolidinyl or cyclopentyl, each of which is unsubstituted or monosubstituted by A, [C(R³)₂]ₚAr, [C(R³)₂]ₚHet¹, Cyc, [C(R³)₂]ₚOR³, CO[C(R³)₂]ₚN(R³)₂ or CO[C(R³)₂]ₚHet¹,

128

R³ denotes H or unbranched alkyl with 1-4 C-atoms or branched alkyl with 3-4 C atoms, Ar denotes phenyl, which is unsubstituted or mono-, di- or trisubstituted by Hal, A, [C(R³)₂]ₚOR³, O[C(R³)₂]ₚOR³, [C(R³)₂]ₚHet¹, CONH₂, CONA and/or CONA₂, Het denotes pyrazolyl, pyridyl, indolyl, isoindolyl, indolinyl, quinolyl or isoquinolyl, each of which is unsubstituted or mono- or disubstituted by A and/or =O, Het¹ denotes pyrazolyl, pyridyl, pyrrolidinyl, piperidinyl, morpholinyl, tetrahydropyranyl or piperazinyl, each of which is unsubstituted or mono- or disubstituted by A and/or [C(R³)₂]ₚHet², Het² denotes pyrrolidinyl, piperidinyl, morpholinyl or piperazinyl, each of which is unsubstituted or monosubstituted by A, A denotes unbranched alkyl with 1-6 C-atoms or branched alkyl with 3-6 C atoms, wherein one or two non-adjacent CH- and/or CH₂-groups may be replaced by N-, O- and/or S-atoms and wherein 1-7 H-atoms may be replaced by F or Cl, Hal denotes F, Cl, Br or I, N denotes 0, 1 or 2, M denotes 1, 2 or 3, P denotes 0, 1, 2, 3 or 4, or a pharmaceutically acceptable alcoholate, hydrate, salt, tautomer or stereoisomer thereof, including mixtures thereof in all ratios.

7. A compound according to claim 1, selected from the group

| No. | Name |
|---|---|
| "A1" | 9-(4-ethoxyphenyl)-N-(1-(1-methylpiperidin-4-yl)-1H-pyrazol-4-yl)-9H-purin-2-amine |
| "A2" | 9-(4-(2-methoxyethoxy)phenyl)-N-(1-(1-methylpiperidin-4-yl)-1H-pyrazol-4-yl)-9H-purin-2-amine |
| "A3" | 4-(2-((1-(tetrahydro-2H-pyran-4-yl)-1H-pyrazol-4-yl)amino)-9H-purin-9-yl)benzamide |
| "A4" | N,9-bis-(1-ethyl-1H-pyrazol-4-yl)-9H-purin-2-amine |
| "A5" | 9-(1-ethyl-1H-pyrazol-4-yl)-N-(1-(tetrahydro-2H-pyran-4-yl)-1H-pyrazol-4-yl)-9H-purin-2-amine |
| "A6" | 9-(4-ethoxyphenyl)-8-methyl-N-(1-(1-methylpiperidin-4-yl)-1H-pyrazol-4-yl)-9H-purin-2-amine |
| "A7" | 9-(4-ethoxyphenyl)-N2-(1-(1-methylpiperidin-4-yl)-1H-pyrazol-4-yl)-9H-purine-2,8-diamine |
| "A8" | N²,9-bis (1-ethyl-1H-pyrazol-4-yl)-9H-purine-2,8-diamine |
| "A9" | 6-(2-((1-ethyl-1H-pyrazol-4-yl)amino)-9H-purin-9-yl)-3,3-dimethylindolin-2-one |
| "A10" | N-(1-(2-(1H-pyrazol-1-yl)ethyl)-1H-pyrazol-4-yl)-9-(4-ethoxyphenyl)-9H-purin-2-amine |
| "A11" | 9-(4-ethoxyphenyl)-N-(1-(3-(piperidin-4-yl)propyl)-1H-pyrazol-4-yl)-9H-purin-2-amine |
| "A12" | 9-(4-chloro-3-fluorophenyl)-N-(1-(tetrahydro-2H-pyran-4-yl)-1H-pyrazol-4-yl)-9H-purine-2-amine |
| "A13" | N-(1-(1-(2-methoxyethyl)piperidin-4-yl)-1H-pyrazol-4-yl)-9-(4-methoxyphenyl)-9H-purin-2-amine |
| "A14" | 9-(4-ethoxy-phenyl)-N²-[1-(2-pyrazol-1-yl-ethyl)-1H-pyrazol-4-yl]-9H-purine-2,8-diamine |
| "A15" | N-(1-(1-methylpiperidin-4-yl)-1H-pyrazol-4-yl)-9-(quinolin-6-yl)-9H-purin-2-amine |
| "A16" | 9-(4-methoxyphenyl)-N-(1-(1-methylpiperidin-4-yl)-1H-pyrazol-4-yl)-9H-purin-2-amine |
| "A17" | N-(1-(4-aminocyclohexyl)-1H-pyrazol-4-yl)-9-(4-ethoxyphenyl)-9H-purin-2-amine |
| "A18" | [9-(4-methoxy-phenyl)-9H-purin-2-yl]-(1H-pyrazol-4-yl)-amine |
| "A19" | [9-(4-methoxy-phenyl)-9H-purin-2-yl]-(1-methyl-1H-pyrazol-3-yl)-amine |
| "A20" | [9-(4-methoxy-phenyl)-9H-purin-2-yl]-(1-phenyl-1H-pyrazol-4-yl)-amine |
| "A21" | (1-methyl-1H-pyrazol-4-yl)-{9-[4-(1-methyl-1H-pyrazol-4-yl)-phenyl]-9H-purin-2-yl}-amine |
| "A22" | N-(2,3-dihydroxy-propyl)-4-[2-(1-ethyl-1H-pyrazol-4-ylamino)-purin-9-yl]-benzamide |

| No. | Name |
|---|---|
| "A23" | (1-methyl-1H-pyrazol-4-yl)-{9-[4-(1-piperidin-4-yl-1H-pyrazol-4-yl)-phenyl]-9H-purin-2-yl}-amine |
| "A24" | N2-(1-methyl-1H-pyrazol-4-yl)-9-[4-(1-methyl-1H-pyrazol-4-yl)-phenyl]-9H-purine-2,8-diamine |
| "A25" | 4-[8-amino-2-(1-ethyl-1H-pyrazol-4-ylamino)-purin-9-yl]-N-(2-hydroxy-ethyl)-benzamide |
| "A26" | N2-(1-methyl-1H-pyrazol-4-yl)-9-[4-(1-piperidin-4-yl-1H-pyrazol-4-yl)-phenyl]-9H-purine-2,8-diamine |
| "A27" | (trans)-3-[9-(3-fluoro-4-iodo-phenyl)-9H-purin-2-ylamino]-cyclopentanol |
| "A28" | (trans)-3-[9-(4-ethoxy-phenyl)-9H-purin-2-ylamino]-cyclopentanol |
| "A29" | (trans)-3-(9-{3-fluoro-4-[1-(2-methoxy-ethyl)-1H-pyrazol-4-yl]-phenyl}-9H-purin-2-ylamino)-cyclopentanol |
| "A30" | (trans)-3-{9-[4-(1-methyl-1H-pyrazol-4-yl)-phenyl]-9H-purin-2-ylamino}-cyclopentanol |
| "A31" | (1R,3R)-3-[9-(3-fluoro-4-iodo-phenyl)-9H-purin-2-ylamino]-cyclopentanecarboxylic acid amide |
| "A32" | (1R,3R)-3-[9-(4-ethoxy-phenyl)-9H-purin-2-ylamino]-cyclopentanecarboxylic acid amide |
| "A33" | (1R,3R)-3-[9-(4-iodo-phenyl)-9H-purin-2-ylamino]-cyclopentanecarboxylic acid amide |
| "A34" | (1R,3R)-3-{9-[4-(2-methoxy-ethoxy)-phenyl]-9H-purin-2-ylamino}-cyclopentanecarboxylic acid amide |
| "A35" | (1R,3R)-3-(9-{3-fluoro-4-[1-(2-methoxy-ethyl)-1H-pyrazol-4-yl]-phenyl}-9H-purin-2-ylamino)-cyclopentanecarboxylic acid amide |
| "A36" | (1R,3R)-3-(9-{4-[1-(2-ethoxy-ethyl)-1H-pyrazol-4-yl]-phenyl}-9H-purin-2-ylamino)-cyclopentanecarboxylic acid amide |
| "A37" | (1R,3R)-3-[9-(2-methyl-quinolin-6-yl)-9H-purin-2-ylamino]-cyclopentanecarboxylic acid amide |
| "A38" | |
| "A39" | |
| "A40" | | or a pharmaceutically acceptable alcoholate, hydrate, salt, tautomer or stereoisomer thereof, including mixtures thereof in all ratios.

8. A process for the preparation of a compound of the formula I according to claim 1 or a pharmaceutically acceptable alcoholate, hydrate, salt, tautomer or stereoisomer thereof, comprising:

a) wherein in formula I, if X denotes H, reacting a compound of the formula II

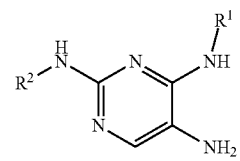

II in which $R^1$ and $R^2$ have the meanings indicated in claim 1,
with trimethyl- or triethylorthoformate
or
b) wherein in formula I, if X denotes $NH_2$ reacting a compound of the formula II with CN—Br
and/or
converting a base or acid of the formula I into one of its salts.

9. A composition comprising at least one compound of the formula I of claim 1 or a pharmaceutically acceptable alcoholate, hydrate, salt, tautomer or stereoisomer thereof, including mixtures thereof in all ratios, and optionally an pharmaceutically acceptable carrier, excipient or vehicle.

10. A composition comprising at least one compound of the formula I of claim 1 or a pharmaceutically acceptable alcoholate, hydrate, salt, tautomer or stereoisomer thereof, including mixtures thereof in all ratios, and at least one further medicament active ingredient.

11. A kit consisting of separate packs of
(a) an effective amount of a compound of the formula I of claim 1 or a pharmaceutically acceptable alcoholate, hydrate, salt, tautomer or stereoisomer thereof, including mixtures thereof in all ratios, and
(b) an effective amount of a further medicament active ingredient.

* * * * *